(12) United States Patent
Clarke et al.

(10) Patent No.: US 10,774,378 B2
(45) Date of Patent: Sep. 15, 2020

(54) METHOD OF TARGET MOLECULE CHARACTERISATION USING A MOLECULAR PORE

(71) Applicant: Oxford Nanopore Technologies Ltd., Oxford (GB)

(72) Inventors: James Anthony Clarke, Oxford (GB); Marion Louise Crawford, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 548 days.

(21) Appl. No.: 15/301,491

(22) PCT Filed: Mar. 31, 2015

(86) PCT No.: PCT/GB2015/050992
§ 371 (c)(1),
(2) Date: Oct. 3, 2016

(87) PCT Pub. No.: WO2015/150787
PCT Pub. Date: Oct. 8, 2015

(65) Prior Publication Data
US 2017/0022557 A1    Jan. 26, 2017
US 2018/0087101 A9    Mar. 29, 2018

Related U.S. Application Data

(63) Continuation-in-part of application No. PCT/GB2014/052737, filed on Sep. 10, 2014.

(30) Foreign Application Priority Data

Apr. 4, 2014    (GB) .................................. 1406155.0

(51) Int. Cl.
*C12Q 1/6869* (2018.01)

(52) U.S. Cl.
CPC .................................. *C12Q 1/6869* (2013.01)

(58) Field of Classification Search
None
See application file for complete search history.

(56) References Cited

U.S. PATENT DOCUMENTS 5,576,204 A    11/1996    Blanco et al.
5,712,126 A    1/1998    Weissman et al.
(Continued)

FOREIGN PATENT DOCUMENTS

AU    2006/336262 A1    7/2007
CN    103695530    4/2014
(Continued)

OTHER PUBLICATIONS

Ohvo et al., Cyclodextrin-Mediated Removal of Sterols from Monolayers: Effects of Sterol Structure and Phospholipids on Desorption Rate, Biochemistry, 35, pp. 8018-8024, 1996. (Year: 1996).*

(Continued)

*Primary Examiner* — Rebecca M Giere
(74) *Attorney, Agent, or Firm* — Wolf, Greenfield & Sacks, P.C.

(57) ABSTRACT

The invention relates to a new method of determining the presence, absence or one or more characteristics of multiple analytes. The invention concerns coupling a first analyte to a membrane containing a detector and investigating the first analyte using the detector. The invention also concerns coupling a second analyte to the membrane and investigating the second analyte. The first analyte is uncoupled from the membrane prior to investigating the second analyte. The invention also relates to polynucleotide sequencing.

15 Claims, 9 Drawing Sheets

Specification includes a Sequence Listing.

(56) References Cited

U.S. PATENT DOCUMENTS

| | | |
|---|---|---|
| 8,828,208 B2 | 9/2014 | Canas et al. |
| 9,057,102 B2 | 6/2015 | Turner et al. |
| 9,222,082 B2 | 12/2015 | Jayasinghe et al. |
| 9,447,152 B2 | 9/2016 | Clarke et al. |
| 9,546,400 B2 | 1/2017 | Turner et al. |
| 9,556,480 B2 | 1/2017 | Turner et al. |
| 9,678,056 B2 | 6/2017 | Turner et al. |
| 9,738,929 B2 | 8/2017 | Turner et al. |
| 10,246,741 B2 | 4/2019 | Clarke et al. |
| 10,337,060 B2 | 7/2019 | Crawford et al. |
| 2002/0192769 A1 | 12/2002 | Park et al. |
| 2010/0331194 A1 | 12/2010 | Turner et al. |
| 2011/0229877 A1 | 9/2011 | Jayasinghe et al. |
| 2012/0100530 A1 | 4/2012 | Moysey et al. |
| 2013/0146456 A1 | 6/2013 | Gundlach et al. |
| 2014/0134618 A1 | 5/2014 | Kokoris et al. |
| 2014/0186823 A1 | 7/2014 | Clarke et al. |
| 2014/0235462 A1 | 8/2014 | Kosteroglou et al. |
| 2014/0262784 A1 | 9/2014 | Clarke et al. |
| 2017/0204457 A1 | 7/2017 | Crawford et al. |
| 2017/0253910 A1 | 9/2017 | Brown et al. |
| 2019/0241949 A1 | 8/2019 | Clarke et al. |
| 2019/0382834 A1 | 12/2019 | Clarke et al. |
| 2020/0102608 A1 | 4/2020 | Crawford et al. |

FOREIGN PATENT DOCUMENTS

| | | |
|---|---|---|
| EP | 2682460 A1 | 1/2014 |
| JP | 2009-519705 A1 | 5/2009 |
| JP | 2012-516146 A | 7/2012 |
| JP | 2014-519823 A | 8/2014 |
| WO | WO 2000/028312 A1 | 5/2000 |
| WO | WO 2000/078668 A1 | 12/2000 |
| WO | WO 2000/079257 A1 | 12/2000 |
| WO | WO 2005/124888 A1 | 12/2005 |
| WO | WO 2006/100484 A2 | 9/2006 |
| WO | WO 2007/057668 A1 | 5/2007 |
| WO | WO 2008/092760 A1 | 8/2008 |
| WO | WO 2008/102120 A1 | 8/2008 |
| WO | WO 2008/102121 A1 | 8/2008 |
| WO | WO 2008/124107 A1 | 10/2008 |
| WO | WO 2009/020682 A2 | 2/2009 |
| WO | WO 2009/035647 A1 | 3/2009 |
| WO | WO 2009/077734 A2 | 6/2009 |
| WO | WO 2009/132124 A2 | 10/2009 |
| WO | WO 2009/151788 A2 | 12/2009 |
| WO | WO 2010/004265 A1 | 1/2010 |
| WO | WO 2010/004273 A1 | 1/2010 |
| WO | WO 2010/034018 | 3/2010 |
| WO | WO 2010/086602 A1 | 8/2010 |
| WO | WO 2010/086603 A1 | 8/2010 |
| WO | WO 2010/086622 A2 | 8/2010 |
| WO | WO 2010/122293 A1 | 10/2010 |
| WO | WO 2011/067559 A1 | 6/2011 |
| WO | WO 2012/033524 A2 | 3/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO2013/057495 * | 4/2013 |
| WO | WO 2013/098561 A1 | 7/2013 |
| WO | WO 2013/098562 A2 | 7/2013 |
| WO | WO 2013/119784 A1 | 8/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A2 | 5/2014 |
| WO | WO 2014/135838 A1 | 9/2014 |
| WO | WO 2015/022544 A1 | 2/2015 |
| WO | WO 2015/055981 A2 | 4/2015 |
| WO | WO 2015/061509 A1 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |

OTHER PUBLICATIONS

Albrecht, Nanobiotechnology: A new look for nanopore sensing. Nat Nanotechnol. Apr. 2011;6(4):195-6. doi: 10.1038/nnano.2011.52.

Ali et al., Sequence-specific recognition of DNA oligomer using peptide nucleic acid (PNA)-modified synthetic ion channels: PNA/DNA hybridization in nanoconfined environment. ACS Nano. Dec. 28, 2010;4(12):7267-74. doi: 10.1021/nn102119q. Epub Nov. 17, 2010.

Andersson et al., Detection of single ion channel activity on a chip using tethered bilayer membranes. Langmuir. Mar. 13, 2007;23(6):2924-7. Epub Feb. 8, 2007.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Chandler et al., Membrane surface dynamics of DNA-threaded nanopores revealed by simultaneous single-molecule optical and ensemble electrical recording. Langmuir. Feb. 3, 2004;20(3):898-905.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Dekker, Solid-state nanopores. Nat Nanotechnol. Apr. 2007;2(4):209-15. doi:10.1038/nnano.2007.27. Epub Mar. 4, 2007.

Feng et al., Nanopore-based fourth-generation DNA sequencing technology. Genomics Proteomics Bioinformatics. Feb. 2015;13(1):4-16. doi: 10.1016/j.gpb.2015.01.009. Epub Mar. 2, 2015. Review. Erratum in: Genomics Proteomics Bioinformatics. Dec. 2015;13(6):383. Genomics Proteomics Bioinformatics. Jun. 2015;13(3):200-201.

Gu et al., Interaction of the noncovalent molecular adapter, beta-cyclodextrin, with the staphylococcal alpha-hemolysin pore. Biophys J. Oct. 2000;79(4):1967-75.

Holden et al., Direct introduction of single protein channels and pores into lipid bilayers. J Am Chem Soc. May 11, 2005;127(18):6502-3.

Howorka et al., Nanopore analytics: sensing of single molecules. Chem Soc Rev. Aug. 2009;38(8):2360-84. doi: 10.1039/b813796j. Epub Jun. 15, 2009.

Howorka et al., Sequence-specific detection of individual DNA strands using engineered nanopores. Nat Biotechnol. Jul. 2001;19(7):636-9.

Ivanov et al., DNA tunneling detector embedded in a nanopore. Nano Lett. Jan. 12, 2011;11(1):279-85. doi: 10.1021/nl103873a. Epub Dec. 6, 2010.

Kasianowicz et al., Characterization of individual polynucleotide molecules using a membrane channel. Proc Natl Acad Sci U S A. Nov. 26, 1996;93(24):13770-3.

Keyser, Controlling molecular transport through nanopores. J R Soc Interface. Oct. 7, 2011;8(63):1369-78. doi: 10.1098/rsif.2011.0222.

Langecker et al., Synthetic lipid membrane channels formed by designed DNA nanostructures. Science. Nov. 16, 2012;338(6109):932-6. doi: 10.1126/science.1225624.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Nikolov et al., Behavior of giant vesicles with anchored DNA molecules. Biophys J. Jun. 15, 2007;92(12):4356-68. Epub Mar. 23, 2007.

(56) References Cited

OTHER PUBLICATIONS

Pfeiffer et al., Bivalent cholesterol-based coupling of oligonucletides to lipid membrane assemblies. J Am Chem Soc. Aug. 25, 2004;126(33):10224-5.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wilson et al., Electronic control of DNA polymerase binding and unbinding to single DNA molecules. ACS Nano. Apr. 28, 2009;3(4):995-1003. doi: 10.1021/nn9000897.

Yoshina-Ishii et al., Arrays of mobile tethered vesicles on supported lipid bilayers. J Am Chem Soc. Apr. 2, 2003;125(13):3696-7.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-LPS Document 13. First Amended Complaint for Patent Infringement. Nov. 30, 2017.

Case 1:17-cv-01353-RGA Document 10. Oxford's opening brief in support of its motion to partially dismiss Pacbio's complaint for patent infringement. Nov. 16, 2017.

United States District Court for the District of Delaware Order. *Pacific Biosciences of California, Inc.* v. *Oxford Nanopore Technolgoies, Inc.* Civil Action No. 17-275-RGA. Nov. 9, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-LPS Document 18. Notice of subsequent events relating to Oxford's motion to dismiss (D.I. 9). Oct. 18, 2017.

Case 1:17-cv-00275-RGA Document 16. Oxford's reply brief in support of its motion to dismiss PacBio's complaint for patent infringement. Jun. 26, 2017.

Case 1:17-cv-00275-RGA Document 14. PacBio's response to Oxford's motion to dismiss. Jun. 5, 2017.

Case 1:17-cv-00275-RGA Document 10. Oxford's opening brief in support of its motion to dismiss PacBio's complaint for patent infringement. May 8, 2017.

U.S. Appl. No. 16/243,118, filed Jan. 9, 2019, Clarke et al.

U.S. Appl. No. 16/428,845, filed May 31, 2019, Clarke et al.

U.S. Appl. No. 16/417,742, filed May 21, 2019, Crawford et al.

Heredia et al., In vitro double transposition for DNA identification. Anal Biochem. Apr. 1, 2010;399(1):78-83. doi:10.1016/j.ab.2009. 11.030. Epub Nov. 26, 2009.

Peng et al., Reverse DNA translocation through a solid-state nanopore by magnetic tweezers. Nanotechnology. May 6, 2009;20(18):185101. doi: 10.1088/0957-4484/20/18/185101. Epub Apr. 14, 2009.

\* cited by examiner

METHOD OF TARGET MOLECULE CHARACTERISATION USING A MOLECULAR PORE

This Application is a national stage filing under 35 U.S.C. § 371 of PCT International Application No. PCT/GB2015/050992, which has an international filing date of Mar. 31, 2015; is a continuation-in-part of PCT International Application No. PCT/GB2014/052737, which has an international filing date of Sep. 10, 2014; and claims foreign priority benefits under 35 U.S.C. § 119(a)-(d) or 35 U.S.C. § 365(b) of British application number 1406155.0, filed Apr. 4, 2014, the contents of each of which are herein incorporated by reference in their entireties.

FIELD OF THE INVENTION

The invention relates to a new method of determining the presence, absence or one or more characteristics of multiple analytes. The invention concerns coupling a first analyte to a membrane containing a detector and investigating the first analyte using the detector. The invention also concerns coupling a second analyte to the membrane and investigating the second analyte. The first analyte is uncoupled from the membrane prior to investigating the second analyte. The invention also relates to polynucleotide sequencing.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

It has previously been demonstrated that ultra low concentration analyte delivery can be achieved by coupling the analyte to a membrane in which the relevant detector is present. This lowers by several orders of magnitude the amount of analyte required in order to be detected (WO 2012/164270).

SUMMARY OF THE INVENTION

The inventors have surprisingly demonstrated that it is possible to investigate multiple analytes in multiple samples by successively coupling the analytes to a membrane in which a detector is present. The first analyte is uncoupled from the membrane prior to investigating the second analyte.

Accordingly, the invention provides a method for determining the presence, absence or one or more characteristics of two or more analytes in two or more samples, comprising:
(a) coupling a first analyte in a first sample to a membrane using one or more anchors;
(b) allowing the first analyte to interact with a detector present in the membrane and thereby determining the presence, absence or one or more characteristics of the first analyte;
(c) uncoupling the first analyte from the membrane;
(d) coupling a second analyte in a second sample to the membrane using one or more anchors; and
(e) allowing the second analyte to interact with a detector in the membrane and thereby determining the presence, absence or one or more characteristics of the second analyte.

The invention also provides:
a method for uncoupling from a membrane an analyte coupled to the membrane using cholesterol, comprising contacting the analyte with a cyclodextrin or a derivative thereof and thereby uncoupling the analyte from the membrane; and
a kit for determining the presence, absence or one or more characteristics of two or more analytes in two or more samples comprising (a) a membrane, (b) two or more anchors which are capable of coupling the two or more analytes to the membrane and (c) one or more agents which are capable of uncoupling at least one of the two or more analytes from the membrane.

DESCRIPTION OF THE SEQUENCE LISTING

Figure 1:
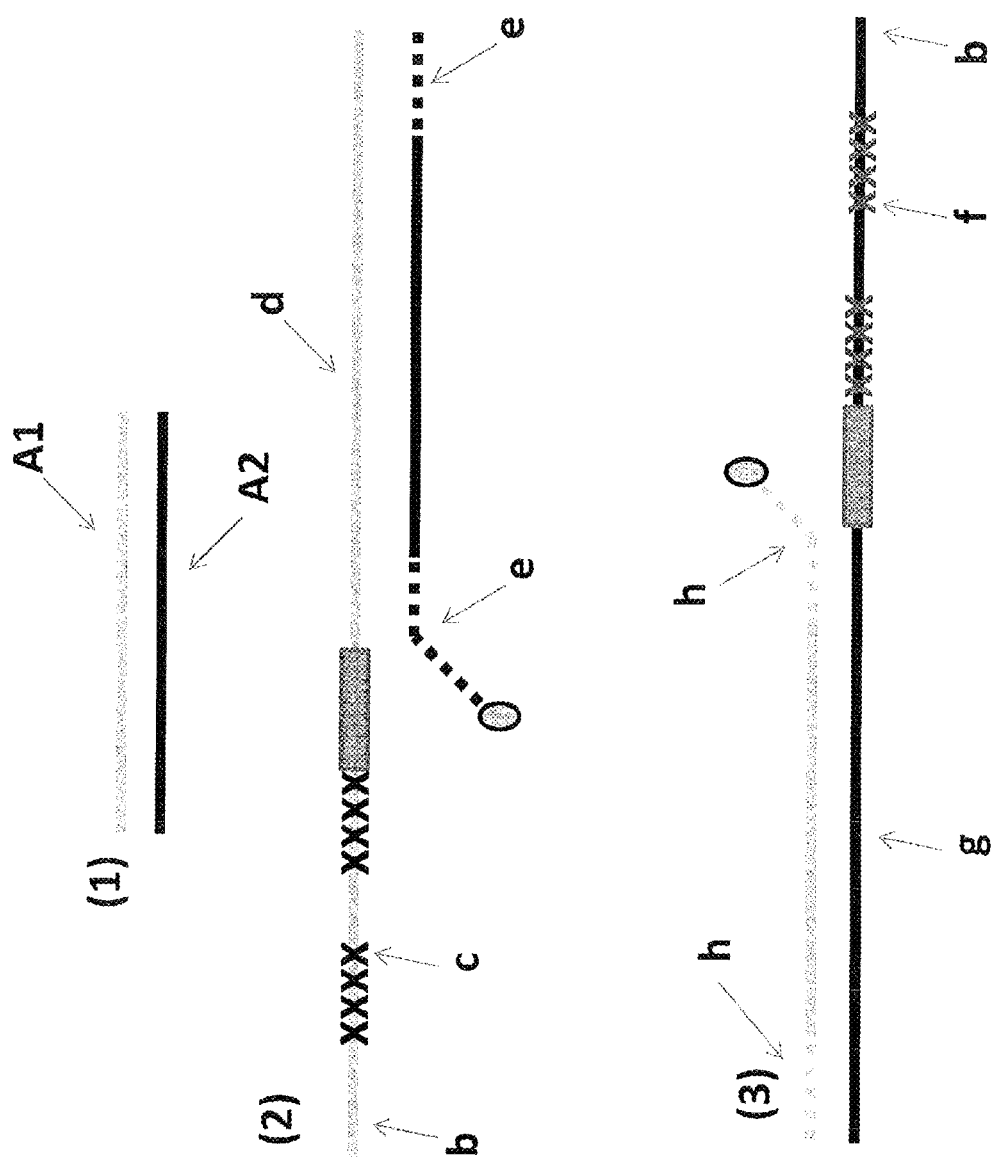
FIG. 1 shows in section (1) the DNA template (SEQ ID NO: 31, labelled A1 and SEQ ID NO: 47 labelled A2) used to prepare the DNA used in Examples 2-4. Section (2) shows a cartoon representation of construct X (described in full in Example 2 materials and methods)—iSpC3 spacers are shown as crosses and four 5-nitroindoles as a grey box and the cholesterol tether as a grey oval; label b=SEQ ID NO: 34, label c=SEQ ID NO: 35, label d=SEQ ID NO: 39, label e=SEQ ID NO: 41. Section (3) shows a cartoon representation of construct Y (described in full in Example 2 materials and methods)—iSpC3 spacers are shown as crosses and four 5-nitroindoles as a grey box and the cholesterol tether as a grey oval; label b=SEQ ID NO: 34, label f=SEQ ID NO: 37, label g=SEQ ID NO: 40, label h=SEQ ID NO: 30.
Figure 2:
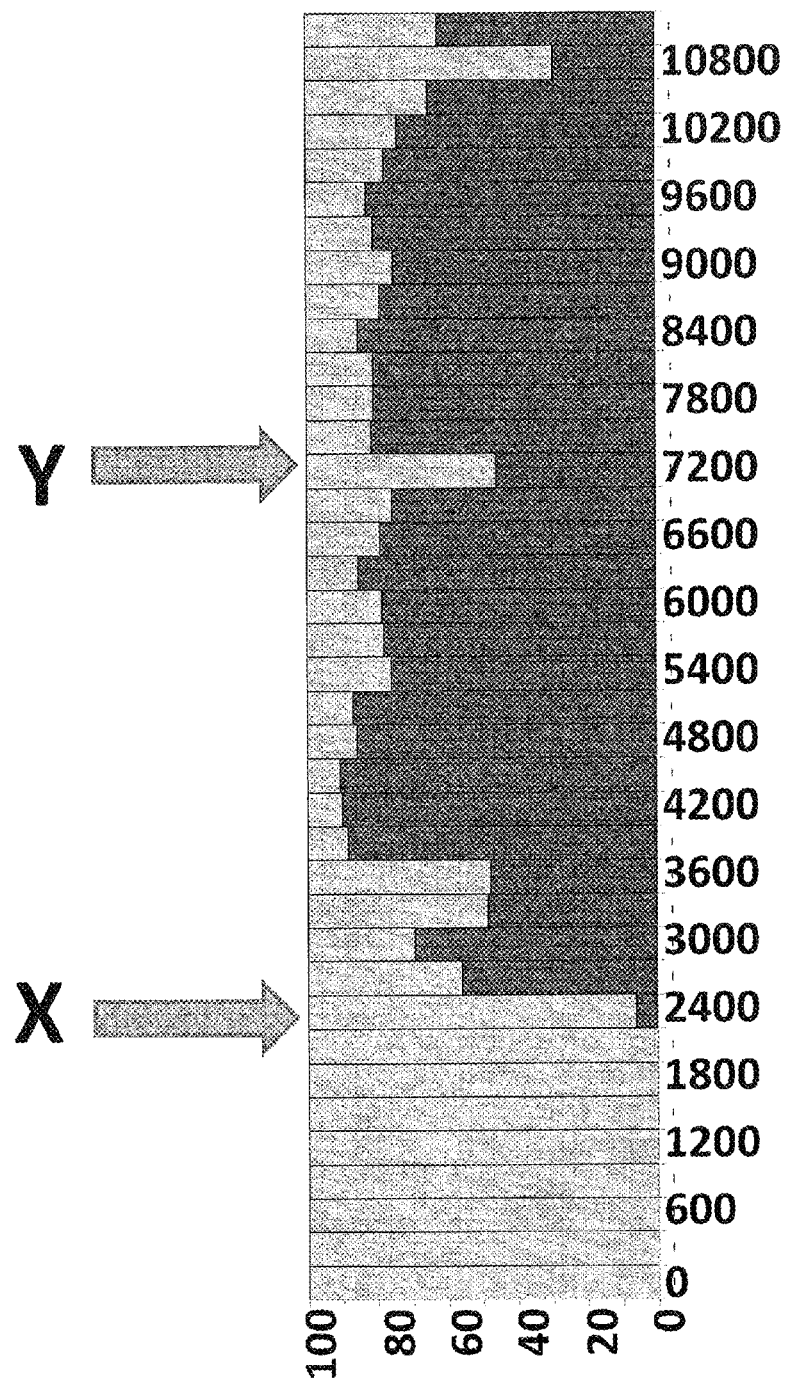
FIG. 2 shows the experimental time course (x-axis label=time (s), y-axis label=percentage (%)) with the percentage of time the nanopores are present in their unblocked state (shown as light grey) compared to when a helicase DNA movement was occurring and the nanopores were partially blocked by the DNA strand (shown as black). DNA construct X was added at 2400 seconds as indicated by the arrow labelled X. DNA construct Y was added at 7200 seconds as indicated by the arrow labelled Y.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows a polynucleotide sequence used in Example 1.

SEQ ID NO: 27 shows a polynucleotide sequence used in Example 1. SEQ ID NO: 27 is attached at the 3' end to four iSp18 spacers which are attached at the opposite end to the 5' end of SEQ ID NO: 28.

SEQ ID NO: 28 shows a polynucleotide sequence used in Example 1. SEQ ID NO: 28 is attached at its 5' end to four iSp18 spacers which are attached at the opposite end to the 3' end of SEQ ID NO: 27.

SEQ ID NO: 29 shows a polynucleotide sequence used in Example 1.

SEQ ID NOs: 30 to 41 shows polynucleotide sequences used in Example 2.

SEQ ID NO: 42 to 46 shows polynucleotide sequences used in Example 5.

SEQ ID NO: 47 shows a polynucleotide sequence used in Example 2.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an analyte" includes two or more analytes, reference to "a polynucleotide" includes two or more polynucleotides, reference to "an anchor" refers to two or more anchors, reference to "a helicase" includes two or more helicases, reference to "a transmembrane pore" includes two or more pores and the like.

All publications, patents and patent applications cited herein, whether supra or infra, are hereby incorporated by reference in their entirety.

Method of the Invention

The invention provides a method for determining the presence, absence or one or more characteristics of two or more analytes. The method comprises coupling a first analyte in a first sample to a membrane using one or more anchors and allowing the analyte to interact with a detector present in the membrane. The presence, absence or one or more characteristics of the first analyte is thereby determined. The method also comprises coupling a second analyte in a second sample to the membrane using one or more anchors and allowing the second analyte to interact with a detector present in the membrane. The presence, absence or one or more characteristics of the second analyte is thereby determined. The first analyte may be uncoupled from the membrane before, after or at the same time as the second analyte is coupled to the membrane.

The inventors have surprisingly demonstrated that ultra low concentration analyte delivery to a detector can be achieved by coupling analytes to a membrane in which detector is present. This lowers by several orders of magnitude the amount of analyte required in order to be detected. The extent to which the amount of analyte needed is reduced could not have been predicted.

In particular, the inventors surprisingly report an increase in the capture of single stranded polynucleotide by ~4 orders of magnitude over that previously reported. As both the detector and analyte are now on the same plane, then ~$10^3$ $M\ s^{-1}$ more interactions occur per second, as diffusion of both molecules is in two dimensions rather than three dimensions. This has dramatic implications on the sample preparation requirements that are of key concern for diagnostic devices such as next-generation sequencing systems.

In addition, coupling the analyte to a membrane has added advantages for various nanopore-enzyme sequencing applications. In strand sequencing, when the polynucleotide analyte is introduced the pore may become blocked permanently or temporarily, preventing the sequencing of the polynucleotide. When one end of the polynucleotide analyte is localised away from the pore, for example by coupling or tethering to the membrane, surprisingly it was found that this temporary or permanent blocking is no longer observed. By occupying one end of the polynucleotide by coupling it to the membrane it also acts to effectively increase the analyte concentration over the detector and so increase the sequencing systems duty cycle.

The method is of course advantageous for detecting multiple analytes that are present at low concentrations. The method preferably allows the presence or one or more characteristics of the two or more analytes to be determined when each analyte is present at a concentration of from about 0.001 pM to about 1 nM, such as less than 0.01 pM, less than 0.1 pM, less than 1 pM, less than 10 pM or less than 100 pM.

The method of the invention is particularly advantageous for polynucleotide sequencing because only small amounts of purified polynucleotide can be obtained from human blood. The method preferably allows estimating the sequence of, or allows sequencing of, a polynucleotide that is present at a concentration of from about 0.001 pM to about 1 nM, such as less than 0.01 pM, less than 0.1 pM, less than 1 pM, less than 10 pM or less than 100 pM. As discussed in more detail below, the two or more analytes may be two or more instances of the same analyte. This is advantageous in polynucleotide sequencing because it allows the sequence of a polynucleotide to be investigated more than once. This leads to increased sequencing efficiency and accuracy.

Coupling one end of a polynucleotide to the membrane (even temporarily) also means that the end will be prevented from interfering with the nanopore-based sequencing process.

The method of the invention also has other advantages. The method provides an alternative to the simultaneous measurement of two or more analytes which removes the need to decouple the measurement signals obtained from each analyte. The method enables the sequential determination of two or more analytes wherein, for example, the conditions required to determine each analyte differ, thus making simultaneous measurement impractical. The method also conveniently enables the measurement of two or more analytes using the same membrane thus providing the possibility for multiple use and extending the lifetime of the membrane.

Analytes

The method of the invention concerns determining the presence, absence or one or more characteristics of two or more analytes. Any number of analytes can be investigated. For instance, the method of the invention may concern determining the presence, absence or one or more characteristics of 3, 4, 5, 6, 7, 8, 9, 10, 20, 30, 50, 100 or more analytes. If three or more analytes are investigated using the method of the invention, the second analyte is also uncoupled from the membrane and the requisite number of steps are added for the third analyte. The same is true for four or more analytes.

The method of the invention may comprise determining or measuring one or more characteristics of each analyte. The method may involve determining or measuring two, three, four or five or more characteristics of each analyte. The one or more characteristics are preferably selected from (i) the size of the analyte, (ii) the identity of the analyte, (iii) the secondary structure of the analyte and (iv) whether or not the analyte is modified. Any combination of (i) to (iv) may be measured in accordance with the invention, such as {i}, {ii}, {iii}, {iv}, {i,ii}, {i,iii}, {i,iv}, {ii,iii}, {ii,iv}, {iii,iv}, {i,ii,iii}, {i,ii,iv}, {i,iii,iv}{ii,iii,iv} or {i,ii,iii,iv}. Different combinations of (i) to (iv) may be measured for the first analyte compared with the second analyte, including any of those combinations listed above. The method preferably comprises estimating the sequence of or sequencing a first polynucleotide and/or a second polynucleotide.

Each analyte can be any substance. Suitable analytes include, but are not limited to, metal ions, inorganic salts, polymers, such as a polymeric acids or bases, dyes, bleaches, pharmaceuticals, diagnostic agents, recreational drugs, explosives and environmental pollutants.

The first analyte and/or second analyte can be an analyte that is secreted from cells. Alternatively, the first analyte and/or second analyte can be an analyte that is present inside cells such that the analyte(s) must be extracted from the cells before the invention can be carried out.

The first analyte and/or second analyte is preferably an amino acid, peptide, polypeptide, a protein or a polynucleotide. The amino acid, peptide, polypeptide or protein can be naturally-occurring or non-naturally-occurring. The polypeptide or protein can include within it synthetic or modified amino acids. A number of different types of modification to amino acids are known in the art. For the purposes of the invention, it is to be understood that the first analyte and/or second analyte can be modified by any method available in the art.

The protein can be an enzyme, antibody, hormone, growth factor or growth regulatory protein, such as a cytokine. The cytokine may be selected from an interleukin, preferably IFN-1, IL-2, IL-4, IL-5, IL-6, IL-10, IL-12 or IL-13, an interferon, preferably IL-$\gamma$ or other cytokines such as TNF-$\alpha$. The protein may be a bacterial protein, fungal protein, virus protein or parasite-derived protein. Before it is contacted with the detector, the protein may be unfolded to form a polypeptide chain.

The first analyte and/or second analyte is most preferably a polynucleotide, such as a nucleic acid. Polynucleotides are discussed in more detail below. A polynucleotide may be coupled to the membrane at its 5' end or 3' end or at one or more intermediate points along the strand. The polynucleotide can be single stranded or double stranded as discussed below. The polynucleotide may be circular. The polynucleotide may be an aptamer, a probe which hybridises to microRNA or microRNA itself (Wang, Y. et al, Nature Nanotechnology, 2011, 6, 668-674). The two polynucleotide analytes may be polynucleotides which bind two proteins and may be used to characterise the proteins, for instance to determine their concentration.

When the analyte is a probe which hybridises to microRNA, the probe may be coupled permanently or transiently to the membrane. This is discussed in more detail below. The probe itself may be adapted to couple directly to the membrane or may hybridise to a complementary polynucleotide which has been adapted to couple to the membrane. The analyte may be a complex of microRNA hybridised to a probe where the probe has distinctive sequences or barcodes enabling it to be identified unambiguously.

When the first analyte and/or second analyte is an aptamer, the aptamer may be coupled permanently or transiently to the membrane. The aptamer itself may be adapted to couple directly to the membrane or may hybridise to a complementary polynucleotide which has been adapted to couple to the membrane. The aptamer may be bound or unbound to a protein analyte and the ultimate purpose of detecting the aptamer may be to detect the presence, absence or one or more characteristics of a protein analyte to which it binds.

The first analyte and second analyte may be different from one another. For instance, the first analyte may be a protein and the second analyte may be a polynucleotide. Alternatively, the first and second analytes may be different polynucleotides. In such instances, there may be no need to remove at least part of the first sample before adding the second sample. This is discussed in more detail below. If the method concerns investigating three or more analytes, they may all be different from one another or some of them may be different from one another.

The first analyte and the second analyte may be two instances of the same analyte. The first analyte may be identical to the second analyte. This allows proofreading, particularly if the analytes are polynucleotides. If the method concerns investigating three or more analytes, they may all be three or more instances of the same analyte or some of them may be separate instances of the same analyte.

Polynucleotide

The first and/or second analyte is preferably a polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA), bridged nucleic acid (BNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Sample

Each analyte is typically present in any suitable sample. The invention is typically carried out on two or more samples that are known to contain or suspected to contain the analytes. Alternatively, the invention may be carried out on two or more samples to confirm the identity of two or more analytes whose presence in the samples is known or expected.

The first sample and/or second sample may be a biological sample. The invention may be carried out in vitro using at least one sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on at least one sample obtained from or extracted from any virus. The first sample and/or second sample is preferably a fluid sample. The first sample and/or second sample typically comprises a body fluid of the patient. The first sample and/or second sample may be urine, lymph, saliva, mucus or amniotic fluid but is preferably blood, plasma or serum. Typically, the first sample and/or second sample is human in origin, but alternatively it may be from another mammal animal such as from commercially farmed animals such as horses, cattle, sheep, fish, chickens or pigs or may alternatively be pets such as cats or dogs. Alternatively, the first sample and/or second sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The first sample and/or second sample may be a non-biological sample. The non-biological sample is preferably a fluid sample. Examples of non-biological samples include surgical fluids, water such as drinking water, sea water or river water, and reagents for laboratory tests.

The first sample and/or second sample is typically processed prior to being used in the invention, for example by centrifugation or by passage through a membrane that filters out unwanted molecules or cells, such as red blood cells. The first sample and/or second sample may be measured immediately upon being taken. The first sample and/or second sample may also be typically stored prior to assay, preferably below −70° C.

The first sample and second sample may be different from one another. For instance, the first sample may be derived from a human and the second sample may be derived from a virus. If the first and second samples are different from one another, they may contain or be suspected of containing the same first and second analytes. If the method concerns investigating three or more samples, they may all be different from one another or some of them may be different from one another.

The first sample and the second sample are preferably two instances of the same sample. The first sample is preferably identical to the second sample. This allows proofreading, particularly if the analytes are polynucleotides. If the method concerns investigating three or more samples, they may all be three or more instances of the same sample or some of them may be separate instances of the same sample.

Membrane

Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompasses a range of phase behaviours from vesicles through to laminar membranes. Membranes formed from these triblock copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

In a preferred embodiment, the invention provides a method for determining the presence, absence or one or more characteristics of two or more analytes in two or more samples, comprising (a) coupling a first analyte in a first sample to a membrane using one or more anchors comprising a triblock copolymer, optionally wherein the membrane is modified to facilitate the coupling; (b) allowing the first analyte to interact with a detector present in the membrane and thereby determining the presence, absence or one or more characteristics of the first analyte; (c) uncoupling the first analyte from the membrane; (d) coupling a second analyte in a second sample to the membrane using one or more anchors; and (e) allowing the second analyte to interact with a detector in the membrane and thereby determining the presence, absence or one or more characteristics of the second analyte.

The membrane is most preferably one of the membranes disclosed in International Application No. PCT/GB2013/052766 or PCT/GB2013/052767.

The amphiphilic molecules may be chemically-modified or functionalised to facilitate coupling of the analyte.

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s–1. This means that the detector and coupled analyte can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the analyte.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lyso-phospholipids, such as 1-Acyl-2-Hydroxy-sn-Glycero-3-Phosphocholine; and ceramides.

In another preferred embodiment, the membrane is a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Coupling

Each analyte may be coupled to the membrane using any known method. Each analyte is coupled to the membrane using one or more anchors.

Coupling means that the analyte is intentionally linked with the membrane using the one or more anchors. The method preferably comprises specifically coupling the first analyte to the membrane using the one or more anchors. The method preferably comprises specifically coupling the second analyte to the membrane using the one or more anchors. The first analyte and/or the second analyte is preferably not coupled with the membrane via non-specific interactions.

Each anchor comprises a group which couples (or binds) to the adaptor and a group which couples (or binds) to the membrane. Each anchor may covalently couple (or bind) to the adaptor and/or the membrane.

Each analyte may be coupled to the membrane using any number of anchors, such as 2, 3, 4 or more anchors. For instance, one analyte may be coupled to the membrane using two anchors each of which separately couples (or binds) to both the analyte and membrane.

The one or more anchors may comprise one or more polynucleotide binding proteins. Each anchor may comprise one or more polynucleotide binding proteins. The polynucleotide binding protein(s) may be any of those discussed below.

In some embodiments, the second analyte is coupled to the membrane using the one or more anchors that were left behind in the membrane following the uncoupling of the first analyte. Alternatively, the second analyte is coupled to the membrane using other (or separate) one or more anchors. The one or more anchors used to couple the second analyte may be the same type of anchor used to couple the first analyte or may be a different type of anchor. This is discussed in more detail below.

If the membrane is an amphiphilic layer, such as a triblock copolymer membrane, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the detector.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalized, for example at least 0.01%, at least 0.1%, at least 1%, at least 10%, at least 25%, at least 50% or 100%.

The first and/or second analyte may be coupled directly to the membrane. The one or more anchors used to couple the first analyte and/or the second analyte to the membrane preferably comprise a linker. The one or more anchors may comprise one or more, such as 2, 3, 4 or more, linkers. One linker may be used couple more than one, such as 2, 3 or more, analytes to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. If the analyte is itself a polynucleotide, it may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane, may be the analyte itself or may be used to couple (or bind) to the analyte. This is discussed in more detail below.

Crosslinkage of analytes can be avoided using a "lock and key" arrangement. Only one end of each linker may react together to form a longer linker and the other ends of the linker each react with the analyte or membrane respectively. Such linkers are described in International Application No. PCT/GB10/000132 (published as WO 2010/086602).

The use of a linker is preferred in the sequencing embodiments discussed below. If a polynucleotide analyte is permanently coupled directly to the membrane in the sense that it does not uncouple when interacting with the detector (i.e. does not uncouple in step (b) or (e)), then some sequence data will be lost as the sequencing run cannot continue to the end of the polynucleotide due to the distance between the membrane and the detector. If a linker is used, then the polynucleotide analyte can be processed to completion.

The coupling may be permanent or stable. In other words, the coupling may be such that the analyte remains coupled to the membrane when interacting with the detector (i.e. does not uncouple in step (b) or (e)).

The coupling may be transient. In other words, the coupling may be such that the analyte may decouple from the membrane when interacting with the detector (i.e. may uncouple in step (b) or (e)). Typically, some instances of the first analyte remain coupled to the membrane, for instance, because they do not interact with the detector and so need to be uncoupled in step (c). For certain applications, such as aptamer detection and polynucleotide sequencing, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The analyte may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide analyte, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 1 below.

TABLE 1

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotide analytes and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the analyte to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the analyte. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other analyte. The Examples below describes how a polynucleotide can be coupled to a membrane using streptavidin/biotin and streptavidin/desthiobiotin. It may also be possible that anchors may be directly added to polynucleotides using terminal transferase with suitably modified nucleotides (e.g. cholesterol or palmitate).

The one or more anchors preferably couple the first analyte and/or the second analyte to the membrane via hybridisation. The hybridisation may be present in any part of the one or more anchors, such as between the one or more anchors and the analyte, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. If the first analyte and/or second analyte are themselves polynucleotides, the one or more anchors may hybridise to the first polynucleotide analyte and/or the second polynucleotide analyte. The one or more anchors may hybridise directly to the polynucleotide analyte, directly to a Y adaptor and/or leader sequence attached to the polynucleotide analyte or directly to a hairpin loop adaptor attached to the polynucleotide analyte (as discussed in more detail below). Alternatively, the one or more anchors may be hybridised to one or more, such as 2 or 3, intermediate polynucleotides (or "splints") which are hybridised to the polynucleotide analyte, to a Y adaptor and/or leader sequence attached to the polynucleotide analyte or to a hairpin loop adaptor attached to the polynucleotide analyte (as discussed in more detail below).

The one or more anchors may comprise a single stranded or double stranded polynucleotide. One part of the anchor may be ligated to a single stranded or double stranded polynucleotide analyte. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively, either a single stranded or double stranded polynucleotide can be ligated to a double stranded polynucleotide analyte and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the a double stranded polynucleotide, this can be achieved using T4 RNA ligase I as for ligation to other regions of single stranded polynucleotides. For addition of double stranded polynucleotides to a double stranded polynucleotide analyte then ligation can be "blunt-ended", with complementary 3' dA/dT tails on the analyte and added polynucleotide respectively (as is routinely done for many sample prep applications to prevent concatemer or dimer formation) or using "sticky-ends" generated by restriction digestion of the analyte and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide analyte is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then anchors, such as cholesterol, thiol, amine, azide, biotin or lipid, can be incorporated into double stranded polynucleotides. Therefore, each copy of the amplified polynucleotide will contain an anchor.

Ideally, the analyte is coupled to the membrane without having to functionalise the analyte. This can be achieved by coupling the one or more anchors, such as a polynucleotide binding protein or a chemical group, to the membrane and allowing the one or more anchors to interact with the analyte or by functionalizing the membrane. The one or more anchors may be coupled to the membrane by any of the methods described herein. In particular, the one or more anchors may comprise one or more linkers, such as maleimide functionalised linkers.

In this embodiment, the analyte is typically RNA, DNA, PNA, TNA or LNA and may be double or single stranded. This embodiment is particularly suited to genomic DNA analytes.

The one or more anchors can comprise any group that couples to, binds to or interacts with single or double stranded polynucleotides, specific nucleotide sequences within the analyte or patterns of modified nucleotides within the analyte, or any other ligand that is present on the polynucleotide.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide analyte. The group may intercalate or interact with the polynucleotide analyte via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide analyte) and osmium complexes (which can react to methylated bases). A polynucleotide analyte may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2,6-diaminopurine monophosphate).

The one or more anchors may couple to (or bind to) the polynucleotide analyte via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide analyte. These types of hydrogen bonds allow a third polynucleotide strand to wind around a double stranded helix and form a triplex. The one or more anchors may couple to (or bind to) a double stranded polynucleotide analyte by forming a triplex with the double stranded duplex.

In this embodiment at least 1%, at least 10%, at least 25%, at least 50% or 100% of the membrane components may be functionalized.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the analyte before contacting with the membrane, but the one or more anchors may be contacted with the membrane and subsequently contacted with the analyte.

In another aspect the analyte may be functionalised, using methods described above, so that it can be recognised by a specific binding group. Specifically the analyte may be functionalised with a ligand such as biotin (for binding to streptavidin), amylose (for binding to maltose binding protein or a fusion protein), Ni-NTA (for binding to poly-histidine or poly-histidine tagged proteins) or peptides (such as an antigen).

According to a preferred embodiment, the one or more anchors may be used to couple a polynucleotide analyte to the membrane when the analyte is attached to a leader sequence which preferentially threads into the pore. Leader sequences are discussed in more detail below. Preferably, the polynucleotide analyte is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

Any of the methods discussed above for coupling polynucleotides to membranes, such as amphiphilic layers, can of course be applied to other analyte and membrane combinations. In some embodiments, an amino acid, peptide, polypeptide or protein is coupled to an amphiphilic layer, such as a triblock copolymer layer or lipid bilayer. Various methodologies for the chemical attachment of such analytes are available. An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Detector

Steps (b) and (e) comprise allowing the first analyte and second analyte respectively to interact with a detector present in the membrane and thereby determining the presence, absence or one or more characteristics of the first analyte and second analyte respectively. The detector in each step may be different. The detector in each step is typically the same. For instance, both the first and second analytes are preferably allowed to interact with a transmembrane pore, preferably the same transmembrane pore.

The coupling of the first analyte and/or the second analyte is not essential for the analyte to interact with the detector. The coupling allows ultra low concentration analyte delivery to the detector.

The detector can be any structure that provides a readable signal in response to the presence, the absence or the one or more characteristics of the first and/or second analyte. The detector can be any structure that provides a readable signal in response to the presence or the absence of the first and/or second analyte. Suitable detectors are known in the art. They include, but are not limited to transmembrane pores, tunnelling electrodes, classis electrodes, nanotubes, FETs (field-effect transistors) and optical detectors, such as atomic force microscopes (AFMs) and scanning tunneling microscopes (STMs).

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the detector (or pore) as a polynucleotide analyte moves with respect to the pore is used to estimate or determine the sequence of the polynucleotide. This is strand sequencing.

In other preferred embodiments, the detector does not detect the analyte using fluorescent means.

The detector preferably comprises a transmembrane pore. A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

If the detector is a pore, step (b) preferably comprises (i) allowing the first analyte to interact with the detector and (ii) measuring the current passing through the detector during the interaction and thereby determining the presence, absence or one or more characteristics of the first analyte and/or step (e) comprises (i) allowing the second analyte to interact with the detector and (ii) measuring the current passing through the detector during the interaction and thereby determining the presence, absence or one or more characteristics of the second analyte.

The first or second analyte is present if the current flows through the pore in a manner specific for the analyte (i.e. if a distinctive current associated with the analyte is detected flowing through the pore). The first or second analyte is absent if the current does not flow through the pore in a manner specific for the analyte. Similarly, the characteristics of the analyte can be determined using the current flowing through the pore during the interaction.

The invention therefore involves nanopore sensing of an analyte. The invention can be used to differentiate analytes of similar structure on the basis of the different effects they have on the current passing through the pore. The invention can also be used to measure the concentration of a particular analyte in a sample.

The invention may also be used in a sensor that uses many or thousands of pores in bulk sensing applications.

During the interaction between the first or second analyte and the pore, the analyte affects the current flowing through the pore in a manner specific for that analyte. For example, a particular analyte will reduce the current flowing through the pore for a particular mean time period and to a particular extent. In other words, the current flowing through the pore is distinctive for a particular analyte. Control experiments may be carried out to determine the effect a particular analyte has on the current flowing through the pore. Results from carrying out the method of the invention on a test sample can then be compared with those derived from such a control experiment in order to identify a particular analyte in the sample, determine whether a particular analyte is present in the sample or determine the characteristics of each analyte. The frequency at which the current flowing through the pore is affected in a manner indicative of a particular analyte can be used to determine the concentration of that analyte in the sample.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 3, at least 4, at least 5, at least 6, at least 7, at least 8, at least 9, at least 10, at least 11, at least 12, at least 13 or at least 14 subunits, such as 3, 4, 5, 6, 7, 8, 9, 10, 11, 12, 13 or 14 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, lysenin, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α, outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Uncoupling

The method of the invention involves uncoupling the first analyte from the membrane. The method of the invention may involve uncoupling the second analyte from the membrane, for instance if three or more analytes are being investigated.

Step (c) (i.e. uncoupling of the first analyte) may be performed before step (d) (i.e. before coupling the second analyte to the membrane). Step (d) may be performed before step (c). If the second analyte is coupled to the membrane before the first analyte is uncoupled, step (c) preferably comprises selectively uncoupling the first analyte from the membrane (i.e. uncoupling the first analyte but not the second analyte from the membrane). A skilled person can design a system in which selective uncoupling is achieved. Steps (c) and (d) may be performed at the same time. This is discussed in more detail below.

In step (c), at least 10% of the first analyte is preferably uncoupled from the membrane. For instance, at least 20%, at least 30%, at least 40%, at least 50%, at least 60%, at least 70%, at least 80% at least 90% or at least 95% of the first analyte may be uncoupled from the membrane. Preferably, all of the first analyte is uncoupled from the membrane. The amount of the first analyte uncoupled from the membrane can be determined using the detector. This is disclosed in the Examples.

The first analyte can be uncoupled from the membrane using any known method. The first analyte is preferably not uncoupled from the membrane in step (c) using the detector, such as a transmembrane pore. The first analyte is preferably not uncoupled from the membrane using a voltage or an applied potential.

Step (c) preferably comprises uncoupling the first analyte from the membrane by removing the one or more anchors from the membrane. In such embodiments, the second analyte is coupled to the membrane using other (or separate) one or more anchors. The one or more anchors used to couple the second analyte may be the same type of anchor used to couple the first analyte or a different type of anchor.

Step (c) more preferably comprises contacting the one or more anchors with an agent which has a higher affinity for the one or more anchors than the one or more anchors have for the membrane. A variety of protocols for competitive binding or immunoradiometric assays to determine the specific binding capability of molecules are well known in the art (see for example Maddox et al, J. Exp. Med. 158, 1211-1226, 1993). The agent removes the one or more anchors from the membrane and thereby uncouples the first analyte. The agent is preferably a sugar. Any sugar which binds to the one or more anchors with a higher affinity than the one or more anchors have for the membrane may be used. The sugar may be a cyclodextrin or derivative thereof as discussed below.

The one or more anchors preferably comprise a hydrophobic anchor, such as cholesterol, and the agent is preferably a cyclodextrin or a derivative thereof or a lipid. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin (am$_7$-βCD), 6-monodeoxy-6-monoamino-β-cyclodextrin (am$_1$-βCD), heptakis-(6-deoxy-6-guanidino)-cyclodextrin (gu$_7$-βCD), heptakis(2,3,6-tri-O-methyl)-β-cyclodextrin or (2-hydroxypropyl)-β-cyclodextrin. Any of the lipids disclosed herein may be used.

The one or more anchors preferably comprise streptavidin, biotin or desthiobiotin and the agent is preferably biotin, desthiobiotin or streptavidin. Both biotin and desthiobiotin bind to streptavidin with a higher affinity than streptavidin binds to the membrane. Biotin has a stronger affinity for streptavidin than desthiobiotin. An anchor comprising streptavidin may therefore be removed from the membrane using biotin or desthiobiotin, depending on the composition of the anchor e.g. as shown in Example 5 and FIG. 7.

The one or more anchors preferably comprise a protein and the agent is preferably an antibody or fragment thereof which specifically binds to the protein. An antibody specifically binds to a protein if it binds to the protein with preferential or high affinity, but does not bind or binds with only low affinity to other or different proteins. An antibody binds with preferential or high affinity if it binds with a Kd of $1 \times 10^{-6}$ M or less, more preferably $1 \times 10^{-7}$ M or less, $5 \times 10^{-8}$ M or less, more preferably $1 \times 10^{-8}$ M or less or more preferably $5 \times 10^{-9}$ M or less. An antibody binds with low affinity if it binds with a Kd of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. Any method may be used to detect binding or specific binding. Methods of quantitatively measuring the binding of an antibody to a protein are well known in the art. The antibody may be a monoclonal antibody or a polyclonal antibody. Suitable fragments of antibodies include, but are not limited to, Fv, F(ab') and F(ab')2 fragments, as well as single chain antibodies. Furthermore, the antibody or fragment thereof may be a chimeric antibody or fragment thereof, a CDR-grafted antibody or fragment thereof or a humanised antibody or fragment thereof.

Step (c) preferably comprises contacting the one or more anchors with an agent which reduces their ability to couple to the membrane. For instance, the agent could interfere with the structure and/or hydrophobicity of the one or more anchors and thereby reduce their ability to couple to the membrane. The one or more anchors preferably comprise cholesterol and the agent is preferably cholesterol dehydrogenase. The one or more anchors preferably comprise a lipid and the agent is preferably a phospholipase. The one or more anchors preferably comprise a protein and the agent is preferably a proteinase or urea. Other combination of suitable anchors and agents will be clear to a person skilled in the art.

Step (c) preferably comprises uncoupling the first analyte from the membrane by separating the first analyte from the one or more anchors. This can be done in any manner. For instance, the linker could be cut in one or more anchors comprising a linker. This embodiment is particularly applicable to one or more anchors which involve linkage via hybridisation. Such anchors are discussed above.

Step (c) more preferably comprises uncoupling the first analyte from the membrane by contacting the first analyte and the one or more anchors with an agent which competes with the first analyte for binding to the one or more anchors. Methods for determining and measuring competitive binding are known in the art. The agent is preferably a polynucleotide which competes with the first analyte for hybridisation to the one or more anchors. For instance, if the first analyte is coupled to the membrane using one or more anchors which involve hybridisation, the analyte can be uncoupled by contacting the one or more anchors with a polynucleotide which also hybridises to the site of hybridisation. The polynucleotide agent is typically added at a concentration that is higher than the concentration of the first analyte and one or more anchors. Alternatively, the polynucleotide agent may hybridise more strongly to the one or more anchors than the first analyte.

Step (c) more preferably comprises (i) contacting the first analyte and the one or more anchors with urea, tris(2-carboxyethyl)phosphine (TCEP), dithiothreitol (DTT), streptavidin or biotin, UV light, an enzyme or a binding agent; (ii) heating the first analyte and one or more anchors; or (iii) altering the pH. Urea, tris(2-carboxyethyl)phosphine (TCEP) or dithiothreitol (DTT) are capable of disrupting anchors and separating the first analyte from the membrane. If an anchor comprises a streptavidin-biotin link, then a streptavidin agent will compete for binding to the biotin. If an anchor comprises a streptavidin-desthiobiotin link, then a biotin agent will compete for binding to the streptavidin. UV light can be used to breakdown photolabile groups. Enzymes and binding agents can be used to cut, breakdown or unravel the anchor. Preferred enzymes include, but are not limited to, an exonuclease, an endonuclease or a helicase. Preferred binding agents include, but are not limited to, an enzyme, an antibody or a fragment thereof or a single-stranded binding protein (SSB). Any of the enzymes discussed below or antibodies discussed above may be used. Heat and pH can be used to disrupt hybridisation and other linkages.

If the first analyte is uncoupled from the membrane by separating the first analyte from the one or more anchors, the one or more anchors will remain in the membrane. Step (d) preferably comprises coupling the second analyte to the membrane using the one or more anchors that were separated from the first analyte. For instance, the second analyte may also be provided with a polynucleotide which hybridises to the one or more anchors that remain in the membrane. Alternatively, step (d) preferably comprises coupling the second analyte to the membrane using separate one or more anchors from the ones separated from the first analyte (i.e. other one or more anchors). The separate one or more anchors may be the same type of anchor used to couple the first analyte to the membrane or may be a different type of anchor. Step (d) preferably comprises coupling the second analyte to the membrane using a different one or more anchors from the ones separated from the first analyte.

In a preferred embodiment, steps (c) and (d) comprise uncoupling the first analyte from the membrane by contacting the membrane with the second analyte such that the second analyte competes with the first analyte for binding to the one or more anchors and replaces the first analyte. For instance, if the first analyte is coupled to the membrane using one or more anchors which involve hybridisation, the analyte can be uncoupled by contacting the one or more anchors with the second analyte attached to a polynucleotide which also hybridises to the sites of hybridisation in the one or more anchors. The second analyte is typically added at a concentration that is higher than the concentration of the first analyte and one or more anchors. Alternatively, the second analyte may hybridise more strongly to the one or more anchors than the first analyte.

Removal or Washing

Although the first analyte is uncoupled from the membrane in step (c), it is not necessarily removed or washed away. If the second analyte can be easily distinguished from the first analyte, there is no need to remove the first analyte.

Between steps (c) and (d), the method preferably further comprises removing at least some of the first sample from the membrane. At least 10% of the first sample may be removed, such as at least 20%, at least 30%, at least 40%, at least 50%, at least 60%, at least 70%, at least 80% or at least 90% of the first sample may be removed. The method more preferably further comprises removing all of the first sample from the membrane. This can be done in any way. For instance, the membrane can be washed with a buffer after the first analyte has been uncoupled. Suitable buffers are discussed below.

Polynucleotide Characterisation

The method of the invention preferably involves measuring one or more characteristics of two or more polynucleotides. The two or more polynucleotides may be different polynucleotides or two instances of the same polynucleotide.

Any number of polynucleotides can be investigated. For instance, the method of the invention may concern determining the presence, absence or one or more characteristics of 3, 4, 5, 6, 7, 8, 9, 10, 20, 30, 50, 100 or more polynucleotides. If three or more polynucleotides are investigated using the method of the invention, the second polynucleotide is also uncoupled from the membrane and the requisite number of steps are added for the third polynucleotide. The same is true for four or more polynucleotides.

The polynucleotides can be naturally occurring or artificial. For instance, the method may be used to verify the sequence of two or more manufactured oligonucleotides. The methods are typically carried out in vitro.

The method may involve measuring two, three, four or five or more characteristics of each polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Step (b) preferably comprises allowing the first polynucleotide to interact with a polynucleotide binding protein which controls the interaction of the first polynucleotide with the detector present in the membrane and/or step (e) preferably comprises allowing the second polynucleotide to interact with a polynucleotide binding protein which controls the interaction of the second polynucleotide with the detector present in the membrane.

More preferably, the method comprises (a) coupling a first polynucleotide in a first sample to a membrane using one or more anchors; (b) contacting the first polynucleotide with a transmembrane pore such that the first polynucleotide moves through the pore; (c) taking one or more measurements as the first polynucleotide moves with respect to the pore wherein the measurements are indicative of one or more characteristics of the first polynucleotide and thereby characterising the first polynucleotide; (d) uncoupling the first polynucleotide from the membrane; (e) coupling a second polynucleotide in a second sample to the membrane using one or more anchors; (f) contacting the second polynucleotide with a transmembrane pore such that the second polynucleotide moves through the pore; and (g) taking one or more measurements as the second polynucleotide moves with respect to the pore wherein the measurements are indicative of one or more characteristics of the second polynucleotide and thereby characterising the second polynucleotide. In this embodiment, step (b) preferably comprises contacting the first polynucleotide with a transmembrane pore and a polynucleotide binding protein such that the protein controls the movement of the first polynucleotide through the pore and/or step (f) preferably comprises contacting the second polynucleotide with a transmembrane pore and a polynucleotide binding protein such that the protein controls the movement of the second polynucleotide through the pore.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17) and variants thereof. Three subunits comprising the sequence shown in SEQ ID NO: 15 or a variant thereof interact to form a trimer exonuclease. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Mhu (SEQ ID NO: 20), TraI Eco (SEQ ID NO: 21), XPD Mbu (SEQ ID NO: 22) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736.

The helicase preferably comprises the sequence shown in SEQ ID NO: 25 (Trwc Cba) or a variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 24 comprises E94C/A360C and then (ΔM1)G1G2 (i.e. deletion of M1 and then addition G1 and G2) or E94C/A360C/C109A/C136A and then (ΔM1)G1G2.

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the first polynucleotide analyte and/or the second polynucleotide analyte with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

A variant of SEQ ID NOs: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Helicase(s) and Molecular Brake(s)

In a preferred embodiment, the method comprises:
(a) providing a first polynucleotide in a first sample with one or more helicases attached to the first polynucleotide and one or more molecular brakes attached to the first polynucleotide;
(b) providing a second polynucleotide in a second sample with one or more helicases attached to the second polynucleotide and one or more molecular brakes attached to the second polynucleotide;
(c) coupling the first polynucleotide in the first sample to a membrane using one or more anchors;
(d) contacting the first polynucleotide with a transmembrane pore and applying a potential across the pore such that the one or more helicases and the one or more molecular brakes are brought together and both control the movement of the first polynucleotide through the pore;
(e) taking one or more measurements as the first polynucleotide moves with respect to the pore wherein the measurements are indicative of one or more characteristics of the first polynucleotide and thereby characterising the first polynucleotide;
(f) uncoupling the first polynucleotide from the membrane;
(g) coupling the second polynucleotide in the second sample to the membrane using one or more anchors;
(h) contacting the second polynucleotide with a transmembrane pore and applying a potential across the pore such that the one or more helicases and the one or more molecular brakes are brought together and both control the movement of the second polynucleotide through the pore; and
(i) taking one or more measurements as the second polynucleotide moves with respect to the pore wherein the measurements are indicative of one or more characteristics of the second polynucleotide and thereby characterising the second polynucleotide.

This type of method is discussed in detail in the International Application PCT/GB2014/052737.

Step (f) (i.e. uncoupling of the first polynucleotide) may be performed before step (g) (i.e. before coupling the second polynucleotide to the membrane). Step (g) may be performed before step (f). If the second polynucleotide is coupled to the membrane before the first polynucleotide is uncoupled, step (f) preferably comprises selectively uncoupling the first polynucleotide from the membrane (i.e. uncoupling the first polynucleotide but not the second polynucleotide from the membrane). A skilled person can design a system in which selective uncoupling is achieved. Steps (f) and (g) may be performed at the same time. This is discussed in more detail below.

The one or more helicases may be any of those discussed above. The one or more molecular brakes may be any compound or molecule which binds to the polynucleotide and slow the movement of the polynucleotide through the pore. The one or more molecular brakes are preferably one or more polynucleotide binding proteins. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase (SEQ ID NO: 8) which act as molecular brakes are disclosed in U.S. Pat. No. 5,576,204. The one or more molecular brakes are preferably derived from a helicase.

Spacers in Polynucleotide Analytes

The one or more helicases may be stalled at one or more spacers as discussed in International Application No. PCT/GB2014/050175 (published as WO 2014/135838). Any configuration of one or more helicases and one or more spacers disclosed in the International Application may be used in this invention.

Double Stranded Polynucleotide

The first polynucleotide analyte and/or the second polynucleotide analyte may be double stranded. If the analyte polynucleotide is double stranded, the method preferably further comprises before the coupling step ligating a hairpin adaptor to one end of the polynucleotide and separating the two strands of the polynucleotide to form a single stranded polynucleotide construct. The single stranded polynucleotide construct may then be allowed to interact with the detector in accordance with the invention. Linking and interrogating both strands on a double stranded construct in this way increases the efficiency and accuracy of characterization. Sequencing using hairpin adaptors is disclosed in International Application Nos. PCT/GB2010/000160 (published as WO 2010/086622) and PCT/GB2012/051786 (published as WO 2013/014451).

Leader Sequence

Before the coupling step, the method preferably comprises attaching to the first and/or second polynucleotide analyte a leader sequence which preferentially threads into the pore. The leader sequence facilitates the method of the invention. The leader sequence is designed to preferentially thread into the transmembrane pore and thereby facilitate the movement of polynucleotide analyte through the pore. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

Double Coupling

The method of the invention may involve double coupling of multiple double stranded polynucleotides. In a preferred embodiment, the invention involves characterising multiple double stranded polynucleotides. The method preferably comprises:

(a) providing a first double stranded polynucleotide in a first sample with a Y adaptor at one end and a hairpin loop adaptor at the other end, wherein the Y adaptor comprises one or more first anchors for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane;

(b) providing a second double stranded polynucleotide in a second sample in a form as defined in step (a);

(c) coupling the first polynucleotide provided in step (a) to a membrane;

(d) contacting the first polynucleotide coupled in step (c) with a transmembrane pore such that at least one strand of the first polynucleotide moves through the pore;

(e) taking one or more measurements as the at least one strand of the first polynucleotide moves with respect to the pore wherein the measurements are indicative of one or more characteristics of the at least one strand of the first polynucleotide and thereby characterising the first polynucleotide;

(f) uncoupling the first polynucleotide from the membrane;

(g) coupling the second polynucleotide provided in step (b) to the membrane;

(h) contacting the second polynucleotide coupled in step (g) with a transmembrane pore such that at least one strand of the second polynucleotide moves through the pore; and (i) taking one or more measurements as the at least one strand of the second polynucleotide moves with respect to the pore wherein the measurements are indicative of one or more characteristics of the at least one strand of the second polynucleotide and thereby characterising the first polynucleotide.

This type of method is discussed in detail in the UK Applications 1406147.7 and 1407815.8 and in the International application being filed concurrently with this application.

The double stranded polynucleotide is provided with a Y adaptor at one end and a hairpin loop adaptor at the other end. The Y adaptor and/or the hairpin loop adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor comprises the one or more first anchors. Anchors are discussed in more detail above.

The Y adaptor preferably comprises a leader sequence which preferentially threads into the pore. Leader sequences are discussed above.

The hairpin adaptor preferably comprises a selectable binding moiety as discussed above. The hairpin adaptor and/or the selectable binding moiety may comprise a region that can be cut, nicked, cleaved or hydrolysed as discussed above.

The Y adaptor and/or the hairpin adaptor may be ligated to the polynucleotide using any method known in the art. One or both of the adaptors may be ligated using a ligase, such as T4 DNA ligase, *E. coli* DNA ligase, Taq DNA ligase, Tma DNA ligase and 9° N DNA ligase. Alternatively, the adaptors may be added to the polynucleotide using the methods of the invention discussed below.

In a preferred embodiment, step a) of the method comprises modifying the double stranded polynucleotide so that it comprises the Y adaptor at one end and the hairpin loop adaptor at the other end. Any manner of modification can be used. The method preferably comprises modifying the double stranded polynucleotide in accordance with the invention. This is discussed in more detail below. The methods of modification and characterisation may be combined in any way.

The strength of coupling (or binding) of the hairpin adaptor to the membrane is greater than the strength of coupling (or binding) of the Y adaptor to the membrane. This can be measured in any way. A suitable method for measuring the strength of coupling (or binding) is disclosed in the Examples of the UK Applications 1406147.7 and 1407815.8 and in the International application which is being filed concurrently.

The strength of coupling (or binding) of the hairpin loop adaptor is preferably at least 1.5 times the strength of coupling (or binding) of the hairpin loop adaptor, such as at least twice, at least three times, at least four times, at least five or at least ten times the strength of coupling (or binding) of the anchor adaptor. The affinity constant (Kd) of the hairpin loop adaptor for the membrane is preferably at least 1.5 times the affinity constant of the Y adaptor, such as at least twice, at least three times, at least four times, at least five or at least ten times the strength of coupling of the Y adaptor.

There are several ways in which the hairpin loop adaptor couples (or binds) more strongly to the membrane than the Y adaptor. For instance, the hairpin loop adaptor may comprise more anchors that than the Y adaptor. For instance, the hairpin loop adaptor may comprise 2, 3 or more second anchors whereas the Y adaptor may comprise one first anchor.

The strength of coupling (or binding) of the one or more second anchors to the membrane may be greater than the strength of coupling (or binding) of the one or more first anchors to the membrane. The strength of coupling (or binding) of the one or more second anchors to the hairpin loop adaptor may be greater than the strength of coupling (or binding) of the one or more first anchors to the Y adaptor. The one or more first anchors and the one or more second anchors may be attached to their respective adaptors via hybridisation and the strength of hybridisation is greater in the one or more second anchors than in the one or more first anchors. Any combination of these embodiments may also be used in the invention. Strength of coupling (or binding) may be measure using known techniques in the art.

The one or more second anchors preferably comprise one or more groups which couples(s) (or bind(s)) to the membrane with a greater strength than the one or more groups in the one or more first anchors which couple(s) (or bind(s)) to the membrane. In preferred embodiments, the hairpin loop adaptor/one or more second anchors couple (or bind) to the membrane using cholesterol and the Y adaptor/one or more first anchors couple (or bind) to the membrane using palmitate. Cholesterol binds to triblock copolymer membranes and lipid membranes more strongly than palmitate. In an alternative embodiment, the hairpin loop adaptor/one or more second anchors couple (or bind) to the membrane using a mono-acyl species, such as palmitate, and the Y adaptor/one or more first anchors couple (or bind) to the membrane using a diacyl species, such as dipalmitoylphosphatidylcholine.

Adding Hairpin Loops and Leader Sequences

Before the coupling step, a double stranded polynucleotide analyte is preferably contacted with a MuA transposase and a population of double stranded MuA substrates, wherein a proportion of the substrates in the population are Y adaptors comprising the leader sequence and wherein a proportion of the substrates in the population are hairpin loop adaptors. The transposase fragments the double stranded polynucleotide analyte and ligates MuA substrates to one or both ends of the fragments. This produces a plurality of modified double stranded polynucleotides comprising the leader sequence at one end and the hairpin loop at the other. The modified double stranded polynucleotides may then be investigated using the method of the invention.

These MuA based methods are disclosed in the International Application No. PCT/GB2014/052505 (published as WO2015022544). They are also discussed in detail in the UK Applications 1406147.7 and 1407815.8 and the International application being filed concurrently with this application (ONT IP 056).

Modified Polynucleotide Analytes

Before characterisation, the first polynucleotide analyte and/or the second polynucleotide analyte may modified by contacting the polynucleotide analyte with a polymerase and a population of free nucleotides under conditions in which the polymerase forms a modified polynucleotide analyte using the polynucleotide analyte as a template, wherein the polymerase replaces one or more of the nucleotide species in the polynucleotide analyte with a different nucleotide species when forming the modified polynucleotide analyte. The modified polynucleotide analyte may then be coupled to the membrane as in step a) and/or d). This type of modification is described in International Application No. PCT/GB2015/050483. Any of the polymerases discussed above may be used. The polymerase is preferably Klenow or 90 North.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 9o North. A primer or a 3' hairpin is typically used as the nucleation point for polymerase extension.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the template polynucleotide analyte with different nucleotide species in the modified polynucleotide analyte, the modified polynucleotide analyte contains k-mers which differ from those in the template polynucleotide analyte. The different k-mers in the modified polynucleotide analyte are capable of producing different current measurements from the k-mers in the template polynucleotide analyte and so the modified polynucleotide analyte provides different information from the template polynucleotide analyte. The additional information from the modified polynucleotide analyte can make it easier to characterise the template polynucleotide analyte. In some instances, the modified polynucleotide analyte itself may be easier to characterise. For instance, the modified polynucleotide may be designed to include k-mers with an increased separation or a clear separation between their current measurements or k-mers which have a decreased noise.

Preferred Embodiment

The invention provides a method of characterising two or more double stranded polynucleotides, comprising
  (a) providing a first double stranded polynucleotide in a first sample with a first Y adaptor at one end and a first hairpin loop adaptor at the other end, wherein the first Y adaptor comprises one or more first helicases and one or more first anchors for coupling the polynucleotide to the membrane, wherein the first hairpin loop adaptor comprises the one or more first molecular brakes and one or more second anchors for coupling the first polynucleotide to the membrane and wherein the strength of coupling of the first hairpin loop adaptor to the membrane is greater than the strength of coupling of the first Y adaptor to the membrane;
  (b) providing a second double stranded polynucleotide in a second sample with a second Y adaptor at one end and a second hairpin loop adaptor at the other end, wherein the second Y adaptor comprises one or more second helicases and one or more third anchors for coupling the polynucleotide to the membrane, wherein the second hairpin loop adaptor comprises one or more second molecular brakes and one or more fourth anchors for coupling the second polynucleotide to the membrane and wherein the strength of coupling of the second hairpin loop adaptor to the membrane is greater than the strength of coupling of the second Y adaptor to the membrane;
  (c) coupling the first polynucleotide in the first sample to a membrane;
  (d) contacting the first polynucleotide with a transmembrane pore and applying a potential across the pore such that the one or more helicases and the one or more molecular brakes are brought together and both control the movement of the first polynucleotide through the pore;
  (e) taking one or more measurements as the first polynucleotide moves with respect to the pore wherein the measurements are indicative of one or more characteristics of the first polynucleotide and thereby characterising the first polynucleotide;

(f) uncoupling the first polynucleotide from the membrane;

(g) coupling the second polynucleotide in the second sample to the membrane;

(h) contacting the second polynucleotide with a transmembrane pore and applying a potential across the pore such that the one or more helicases and the one or more molecular brakes are brought together and both control the movement of the second polynucleotide through the pore; and (i) taking one or more measurements as the second polynucleotide moves with respect to the pore wherein the measurements are indicative of one or more characteristics of the second polynucleotide and thereby characterising the second polynucleotide This combines the methods disclosed in the UK Applications 1406155.0, 1406147.7, 1407815.8 and 1406151.9 and International Application PCT/GB2014/052737 and the International application being co-filed at this time (ONT IP 056). Any of the embodiments disclosed herein and therein may be applied to the preferred embodiment.

Other Characterisation Method

In another embodiment, a first polynucleotide analyte and/or a second polynucleotide analyte is characterised by detecting labelled species that are released as a polymerase incorporates nucleotides into the polynucleotide. The polymerase uses the first and/or second polynucleotide analyte as a template. Each labelled species is specific for each nucleotide. The first and/or second polynucleotide analyte is contacted with a transmembrane pore, a polymerase and labelled nucleotides such that phosphate labelled species are sequentially released when nucleotides are added to the polynucleotide(s) by the polymerase, wherein the phosphate species contain a label specific for each nucleotide. The polymerase may be any of those discussed above. The phosphate labelled species are detected using the pore and thereby characterising the first and/or second polynucleotide analyte. This type of method is disclosed in European Application No. 13187149.3 (published as EP 2682460). Any of the embodiments discussed above equally apply to this method.

Method Involving Cholesterol and Cyclodextrin

The invention also provides a method for uncoupling from a membrane an analyte coupled to the membrane using an anchor comprising cholesterol, comprising contacting the analyte with a cyclodextrin or a derivative thereof and thereby uncoupling the analyte from the membrane. Any of the embodiments discussed above, particularly those concerning the analyte, anchor, cyclodextrin or a derivative thereof and membrane, are equally applicable to this method. The analyte is preferably a polynucleotide. The polynucleotide preferably comprises a leader sequence as defined above. The cholesterol anchor preferably comprises a polynucleotide sequence which is hybridised to the leader sequence. The polynucleotide sequence is preferably covalently attached to the cholesterol in the anchor.

Kits

The present invention also provides a kit for determining the presence, absence or one or more characteristics of two or more analytes in two or more samples comprising (a) a membrane, (b) one or more anchors which are capable of coupling the two or more analytes to the membrane, such as one or more first anchors which are capable of coupling a first analyte to the membrane and one or more second anchors which are capable of coupling a second analyte to the membrane and (c) one or more agents which are capable of uncoupling at least one of, such as both of, the two or more analytes from the membrane. The one or more anchors and one or more agents may be any of those discussed above with reference to the method of the invention.

The kit preferably further comprises a detector, such as a transmembrane pore. Any of the detectors discussed above may be in the kit.

The kit preferably further comprises a hairpin loop and/or a leader sequence which is capable of preferentially threading into a transmembrane pore. The kit preferably further comprises a polynucleotide binding protein. Preferred hairpin loops, leader sequences and polynucleotide binding proteins are discussed above.

Any of the embodiments discussed above with reference to the method of the invention equally apply to the kits. The kit may further comprise the components of a membrane, such as the components of an amphiphilic layer or a triblock copolymer membrane.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

The following Examples illustrate the invention.

EXAMPLES

Example 1

This example shows a control experiment which illustrated that free DNA in solution, which had not been coupled to the membrane, was not prevented from entering the nanopore by the presence of methyl-β-cyclodextrin in the experimental system.

Materials and Methods

Electrical measurements were acquired from single MspA nanopores MS(B1-G75S/G77S/L88N/Q126R)8 MspA (MspA-B2C) (SEQ ID NO: 2 with mutations G75S/G77S/L88N/Q126R) inserted in block co-polymer in buffer (600 mM KCl, 25 mM potassium phosphate, 75 mM potassium ferrocyanide (II), 25 mM potassium ferricyanide (III) pH 8.0) at a temperature of 15° C. After achieving a single pore inserted in the block co-polymer, then buffer (1 mL, 600 mM KCl, 25 mM potassium phosphate, 75 mM potassium ferrocyanide (II), 25 mM potassium ferricyanide (III) pH 8.0) was flowed through the system to remove any excess MspA-B2C nanopores. Two DNA samples (100 nM, 1—SEQ ID NO: 26 and SEQ ID NO: 29 and 2—SEQ ID NO: 27 attached at its 5' end to four iSp18 spacers which are attached at the opposite end to the 3' end of SEQ ID NO: 28) were added to the system and the experiment was run at an applied potential of 120 mV for 30 minutes. The system was then flushed with methyl-β-cyclodextrin (100 μM) and the DNA samples 1 and 2 at a concentration of 100 nM in a total volume of 500 μL and the experiment run at an applied potential of 120 mV for a further 30 minutes. The system was then flushed with two 1 mL flushes of methyl-β-cyclodextrin (100 µM) and the DNA samples 1 and 2 at a concentration of 100 nM.

A similar control experiment to the one described previously was carried out except that for all the steps which had contained methyl-β-cyclodextrin only DNA samples were added and no methyl-β-cyclodextrin was flushed through the system.

Results

The control experiment where only free DNA was added to the system consistently exhibited short spikes in the current trace which corresponded to the DNA translocating through the nanopore under the applied potential. This illustrated that DNA translocation was seen for each flush of the nanopore system with DNA samples 1 and 2.

These controls were undertaken to confirm that the reduction in the number of DNA translocations observed (see Example 4) was due to the methyl-β-cyclodextrin removing the cholesterol from the membrane surface, rather than preventing the strand from entering the pore. The controls tested whether the cyclodextrin could have bound along the length of the DNA, impeding its ability to thread through the pore, and thus preventing the strand from being detected despite the fact that it was still attached to the membrane. In these experiments, free DNA was used, which had no anchor to couple it to the membrane, if the interaction of the cyclodextrin was confined specifically to the cholesterol, the cyclodextrin should have had no effect on the DNA in this case. Any reduction in number of DNA translocations observed would, therefore, have been due to binding of the body of the DNA. No difference in the number of DNA translocations was observed in the presence or absence of cyclodextrin, suggesting that the cyclodextrin present in the system did not bind to the free DNA and prevent its translocation through the nanopore.

Example 2

This example shows a further control experiment which illustrated that when a first sample of coupled DNA was added to the nanopore system followed by a second sample, without flushing the system with a de-coupling agent or buffer with no DNA present, then the number of helicase-controlled DNA movements detected over a defined period remained fairly constant and helicase controlled DNA movements were observed for both samples.

Materials and Methods

The strands used in this study were from a region of the lambda genome, between 45,042 bp and 48,487 bp. Analytes were made by the polymerase PCR method to include hybridisation sites at defined ends of each of the template and template compliment strands as desired. PCR was carried out from lambda genomic DNA.

The DNA template (SEQ ID NO: 31 which corresponds to the sequence of the strand labelled A1which was hybridised to SEQ ID NO: 47 which corresponds to the sequence for the strand labelled A2, see FIG. 1(1)) was made using KAPA HiFi 2× Master mix, lambda DNA (NEB) and primers SEQ ID NO: 32 and SEQ ID NO: 33. Reactions were cycled 20 times and product of the correct size was purified by Gel Filtration on Sephacryl S1000 column and concentrated to 0.25 mg/ml using Millipore Ultracel 15 50 kDa concentrators.

DNA constructs (X and Y) for electrophysiology experiments were made according to the same reaction mix; 2× LongAmp Taq master mix, 300 nM of primers 1 and 2 or 3 and 4, 1.2 ng ul$^{-1}$ DNA template (SEQ ID NO: 31 which corresponds to the sequence for the strand labelled A1which was hybridised to SEQ ID NO: 47 which corresponds to the sequence for the strand labelled A2, see FIG. 1(1)). DNA constructs were all amplified according to the same cycling program; 94° C. for 2 mins, [94° C. for 15 secs, 58° C. for 30 secs, 65° C. for 2 mins]$_{12}$ and 65° C. for 5 mins. DNA constructs were all purified from a 0.8% agarose gel according to manufacturer's instructions (Qiagen Gel Extraction kit) and then SPRI purified (Agencourt AMPure beads) according to manufacturer's instructions.

For DNA construct X=SEQ ID NO: 34 attached at its 3' end to four iSpC3 spacers which are attached at the opposite end to the 5' end of SEQ ID NO: 35; SEQ ID NO: 35 is attached at the 3' end to four iSpC3 spacers which are attached at the opposite end to four 5-nitroindoles which are attached to the 3' end of SEQ ID NO: 39. The primers used to produce construct X are primer 1—SEQ ID NO: 34 attached at the 3' end to four iSpC3 spacers which are attached at the opposite end to the 5' end of SEQ ID NO: 35; SEQ ID NO: 35 is also attached at the 3' end to four iSpC3 spacers which are attached at the opposite end to four 5-nitroindoles which are attached to the 5' end of SEQ ID NO: 36 and primer 2—SEQ ID NO: 37 is attached at the 3' end to four 5-nitroindoles which are attached at the opposite end to the 5' end of SEQ ID NO: 38.

Construct X was then hybridised to SEQ ID NO: 41 and SEQ ID NO: 41 which is attached at the 3' end to six iSp18 spacers which are attached at the opposite end to two thymines and a 3' cholesterol TEG (FIG. 1(2) shows a cartoon representation of construct X). The tethers were annealed at a five-fold excess at room temperature for ten minutes in 25 mM potassium phosphate buffer, 151 mM potassium chloride, pH 8.0.

For DNA construct Y=SEQ ID NO: 34 attached at its 3' end to four iSpC3 spacers which are attached at the opposite end to the 5' end of SEQ ID NO: 37; SEQ ID NO: 37 is attached at the 3' end to four iSpC3 spacers which are attached at the opposite end to four 5-nitroindoles which are attached to the 5' end of SEQ ID NO: 40. The primers used to produce construct Y are primer 3—SEQ ID NO: 34 attached at the 3' end to four iSpC3 spacers which are attached at the opposite end to the 5' end of SEQ ID NO: 37; SEQ ID NO: 37 is attached at the 3' end to four iSpC3 spacers which are attached at the opposite end to four 5-nitroindoles which are attached to the 5' end of SEQ ID NO: 38 and primer 4—SEQ ID NO: 35 is attached at the 3' end to four 5-nitroindoles which are attached at the opposite end to the 5' end of SEQ ID NO: 36.

Construct Y was then hybridised to SEQ ID NO: 30 and SEQ ID NO: 30 which is attached at the 3' end to six iSp18 spacers which are attached at the opposite end to two thymines and a 3' cholesterol TEG (FIG. 1(3) shows a cartoon representation of construct Y). The tethers were annealed at a five-fold excess at room temperature for ten minutes in 25 mM potassium phosphate buffer, 151 mM potassium chloride, pH 8.0.

Prior to setting up the experiment, the DNA constructs X and Y with their appropriate tethers (stock concentration 20 nM, final concentration added to nanopore system 0.1 nM) were separately incubated with reagents as described. Firstly the DNA was pre-incubated at room temperature for five minutes with T4 Dda-E94C/A360C (stock concentration 250 nM, final concentration added to nanopore system 1 nM, SEQ ID NO: 24 with mutations E94C/A360C) in buffer (151 mM KCl, 25 mM phosphate, 2 mM EDTA, pH8.0). After five minutes TMAD (500 µM) was added to the pre-mix and the mixture incubated for a further 5 minutes. Finally, MgCl2 (10 mM final concentration), ATP (2.5 mM final concentration) and buffer (150 mM potassium ferrocyanide (II), 150 mM potassium ferricyanide and 25 mM potassium phosphate pH 8.0) were added to the pre-mix.

Electrical measurements were acquired from single MspA nanopores (MspA-B2C) inserted in block co-polymer in buffer (25 mM potassium phosphate, 150 mM potassium ferrocyanide (II), 150 mM potassium ferricyanide (III), pH 8.0). After achieving a single pore inserted in the block co-polymer, then buffer (2 mL, 25 mM potassium phosphate pH 8.0, 150 mM potassium ferrocyanide (II) and 150 mM potassium ferricyanide (III)) was flowed through the system to remove any excess MspA nanopores. The enzyme (T4 Dda-E94C/A360C, 1 nM final concentration), DNA construct X (0.1 nM final concentration), fuel (MgCl2 10 mM final concentration, ATP 2.5 mM final concentration) pre-mix (150 µL total) was then added to the single nanopore experimental system and the experiment was run at a holding potential of 120 mV for 2 hours and helicase-controlled DNA movement was monitored. After two hours, the experimental protocol was stopped, the potential set to zero and the DNA construct Y/enzyme pre-mix (150 µL total) was then added directly to the system with no de-coupling agents or flushes of buffer included. The experiment was then run for a further 2 hours at a holding potential of 120 mV and helicase controlled DNA movement monitored.

Results and Discussion

DNA contructs X and Y (shown in FIGS. 1 (a) and (b) respectively) were prepared from the same 3.8 kB section of the lambda phage genome. Adaptors were attached to give an overhanging "leader" at one end of the duplex, which allowed capture and threading by the pore as well as providing an enzyme binding site. The other end was left blunt so only the strand with the leader on was captured and sequenced. The two samples had the adaptor ligated to opposite ends, such that the leader was joined to strand A1 (shown in FIG. 1(2)) in DNA construct X and to strand A2 (shown in FIG. 1(3)) in DNA construct Y. This meant that DNA constructs X and Y gave detectable strand movements with sequences that mapped only to distinct regions of the lambda genome. These movements were easily distinguished, so provided a convenient way of identifying two different test samples; however any other samples with different sequences could have been used just as well.

Helicase controlled DNA movement was observed for both DNA constructs X and Y, with T4 Dda-E94C/A360C. Figure two shows the experimental time course with the percentage of time the nanopores were present in their unblocked state (shown as light grey) compared to when a helicase DNA movement was occurring and the nanopores were partially blocked by the DNA strand (shown as black). For the first 2100 seconds no DNA was present in the system, therefore, the nanopores were in an unblocked state. DNA construct X was added at 2400 seconds and helicase controlled DNA movements were occurring through the nanopore around 80% of the time. DNA construct Y was then flowed into the nanopore system at 7200 seconds and again helicase controlled DNA movement through the nanopore was observed for approximately 80% of the time.

Upon the addition of construct X, the helicase controlled DNA movements observed were all identified as corresponding to this construct. When construct Y was flowed into the system helicase controlled DNA movements corresponding to Y were detected as well as a significant number of movements which corresponded to construct X. Experimental data showed that the rate of helicase controlled DNA movements detected remained fairly constant throughout the experiment and that by adding construct Y to the system, with no additional flushing or de-coupling agents, helicase controlled DNA movements were detected for both samples.

Example 3

This example illustrates that when coupled DNA construct X was added to the nanopore system it was not possible to remove the sample simply by flushing the system with a large volume of buffer.

Materials and Methods

DNA constructs X and Y were prepared as described in Example 2. The DNA constructs were pre-incubated with enzyme as described in Example 2 producing the construct X and construct Y pre-mixes.

The nanopore experimental system was set up as described in Example 2. DNA construct X/enzyme pre-mix (300 µL total) was added to the experimental system and the experiment run at a holding potential of 120 mV for two hours and helicase controlled DNA movement was monitored. After two hours, the experimental protocol was stopped, the potential set to zero and buffer (10 mL of 150 mM potassium ferrocyanide (II), 150 mM potassium ferricyanide (III), 25 mM potassium phosphate pH 8.0) was flowed through the nanopore system in order to try and remove coupled DNA construct X. After the buffer flush, the experiment was run with no additional DNA added to the system at a holding potential of 120 mV for two hours and helicase controlled DNA movement was monitored. Finally, DNA construct Y/enzyme pre-mix (300 µL total) was added to the experimental system and the experiment run at a holding potential of 120 mV for two hours and helicase controlled DNA movement was monitored.

Results and Discussion

Figure 3:
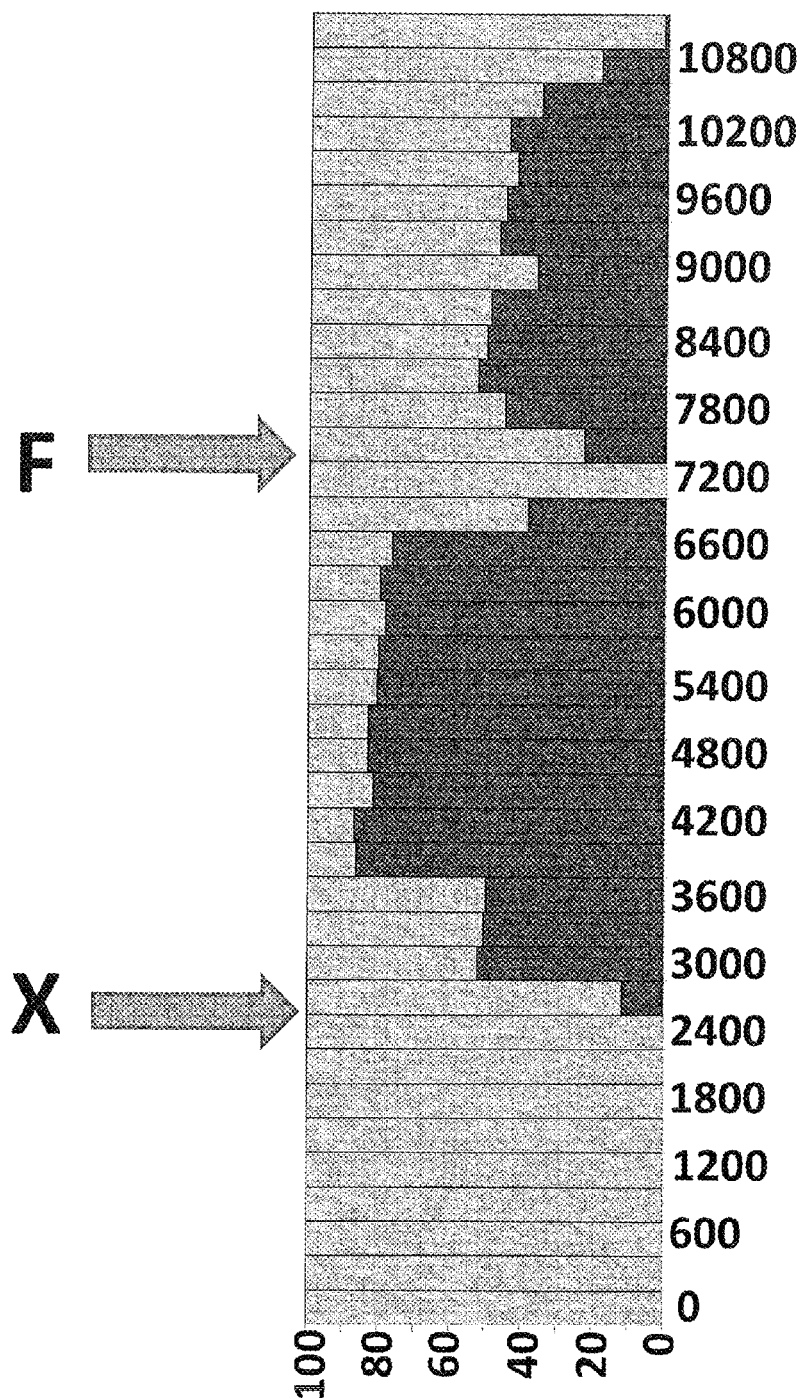
FIG. 3 shows part of the experimental time course (x-axis label=time (s), y-axis label=percentage (%)) with the percentage of time the nanopores are present in their unblocked state (shown as light grey) compared to when a helicase DNA movement was occurring and the nanopores were partially blocked by the DNA strand (shown as black). DNA construct X was added at 2700 seconds as indicated by the arrow labelled X. The buffer flush (10 mL) was at 7500 seconds as indicated by the arrow labelled F.

Helicase controlled DNA movement was observed for both DNA constructs X and Y, with T4 Dda-E94C/A360C. FIG. 3 shows part of the experimental time course with the percentage of time the nanopores were present in their unblocked state (shown as light grey) compared to when a helicase DNA movement was occurring and the nanopores were partially blocked by the DNA strand (shown as black). For the first 2400 seconds no DNA was present in the system, therefore, the nanopores were in an unblocked state. DNA construct X was added at 2700 seconds and helicase controlled DNA movements were occurring through the nanopore around 80% of the time. Buffer (10 mL) was flowed across the system, at 7500 seconds and then the percentage of time the nanopore was partially blocked owing to helicase controlled DNA movement was then monitored. After flushing with buffer, helicase controlled DNA movements were occurring through the nanopore around 50% of the time. This indicated that the amount of coupled DNA construct X present in the system had been reduced by the buffer flush, however, a large number of helicase controlled DNA movements were still detected. Upon the addition of DNA construct Y, helicase controlled DNA movements corresponding to Y were detected as well as a significant number of helicase controlled DNA movements which corresponded to construct X which was still present in the system.

Example 4

This example illustrates how methyl-β-cyclodextrin was used to decouple DNA, which was coupled to the membrane using a cholesterol TEG, from the membrane. A solution of methyl-β-cyclodextrin was added to the nanopore system for 1, 10 and 30 mins and the number of helicase-controlled DNA movements detected over a defined period was monitored after each incubation. This experiment illustrated that even using an incubation period of only one minute significant decoupling of the DNA from the membrane was detected.

Materials and Methods

DNA constructs X and Y were prepared as described in Example 2. The DNA constructs were pre-incubated with enzyme as described in Example 2 producing the construct X and construct Y pre-mixes.

The nanopore experimental system was set up as described in Example 2. DNA construct X/enzyme pre-mix (150 µL total) was added to the experimental system and the experiment run at a holding potential of 120 mV for two hours and helicase controlled DNA movement was monitored. After two hours, the experimental protocol was stopped, the potential set to zero and methyl-β-cyclodextrin (150 µL of 100 µM) was flowed onto the nanopore system and incubated for 1, 10 or 30 minutes in order to try and remove coupled DNA construct X. After the appropriate incubation period, buffer (150 µL, 150 mM potassium ferrocyanide (II), 150 mM potassium ferricyanide (III), 25 mM potassium phosphate, pH 8.0) was flushed through the system to remove any de-coupled DNA and excess methyl-β-cyclodextrin. After the buffer flush, the experiment was run with no additional DNA added to the system at a holding potential of 120 mV for two hours and helicase controlled DNA movement was monitored. Finally, DNA construct Y/enzyme pre-mix (150 µL total) was added to the experimental system and the experiment run at a holding potential of 120 mV for two hours and helicase controlled DNA movement was monitored. The same de-coupling procedure was then repeated for DNA construct Y.

Results and Discussion

Figure 4:
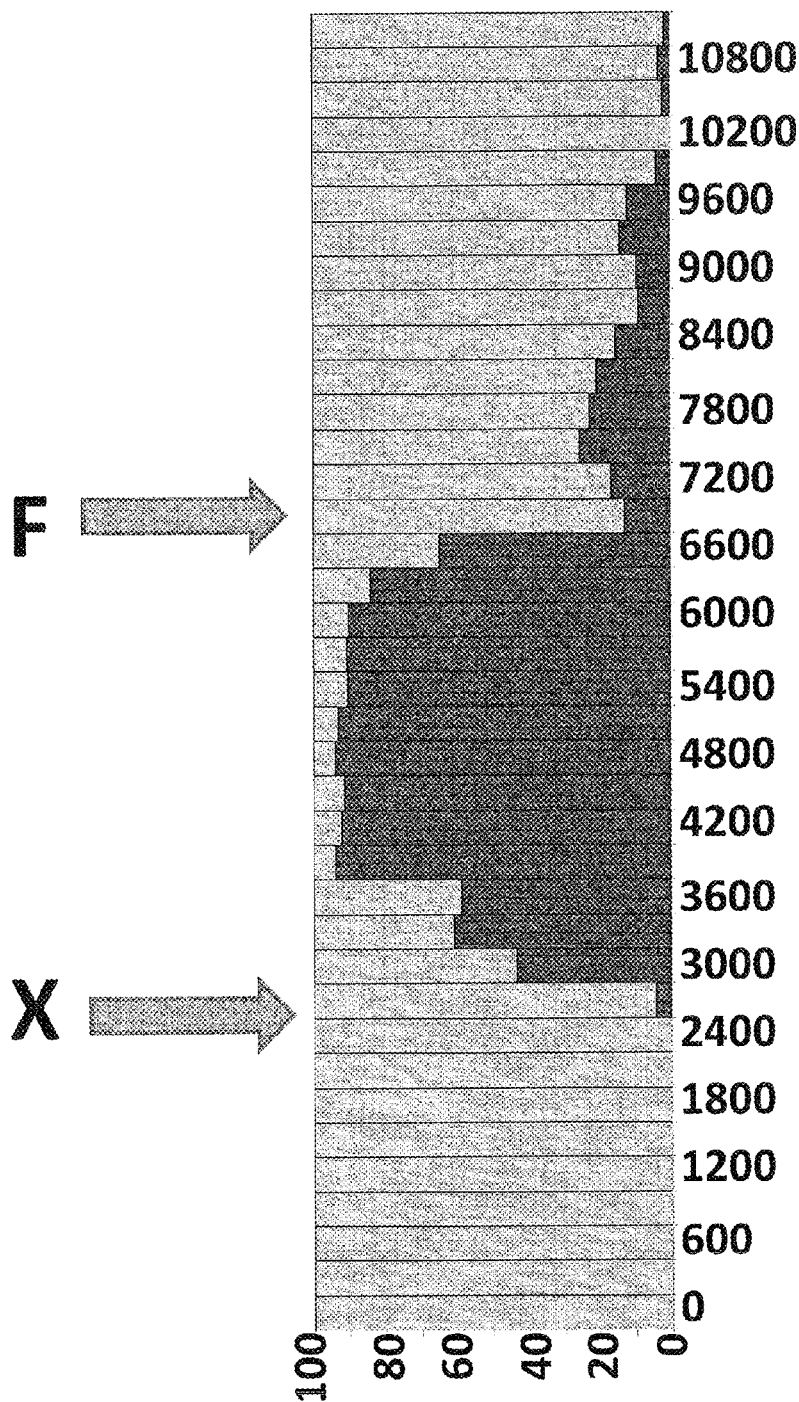
FIG. 4 shows part of the experimental time course (x-axis label=time (s), y-axis label=percentage (%)) with the percentage of time the nanopores are present in their unblocked state (shown as light grey) compared to when a helicase DNA movement was occurring and the nanopores were partially blocked by the DNA strand (shown as black). DNA construct X was added at 2700 seconds as indicated by the arrow labelled X. The 1 min methyl-β-cyclodextrin incubation and then flush (100 μM, 150 μL) was at 6900 seconds as indicated by the arrow labelled F.
Figure 5:
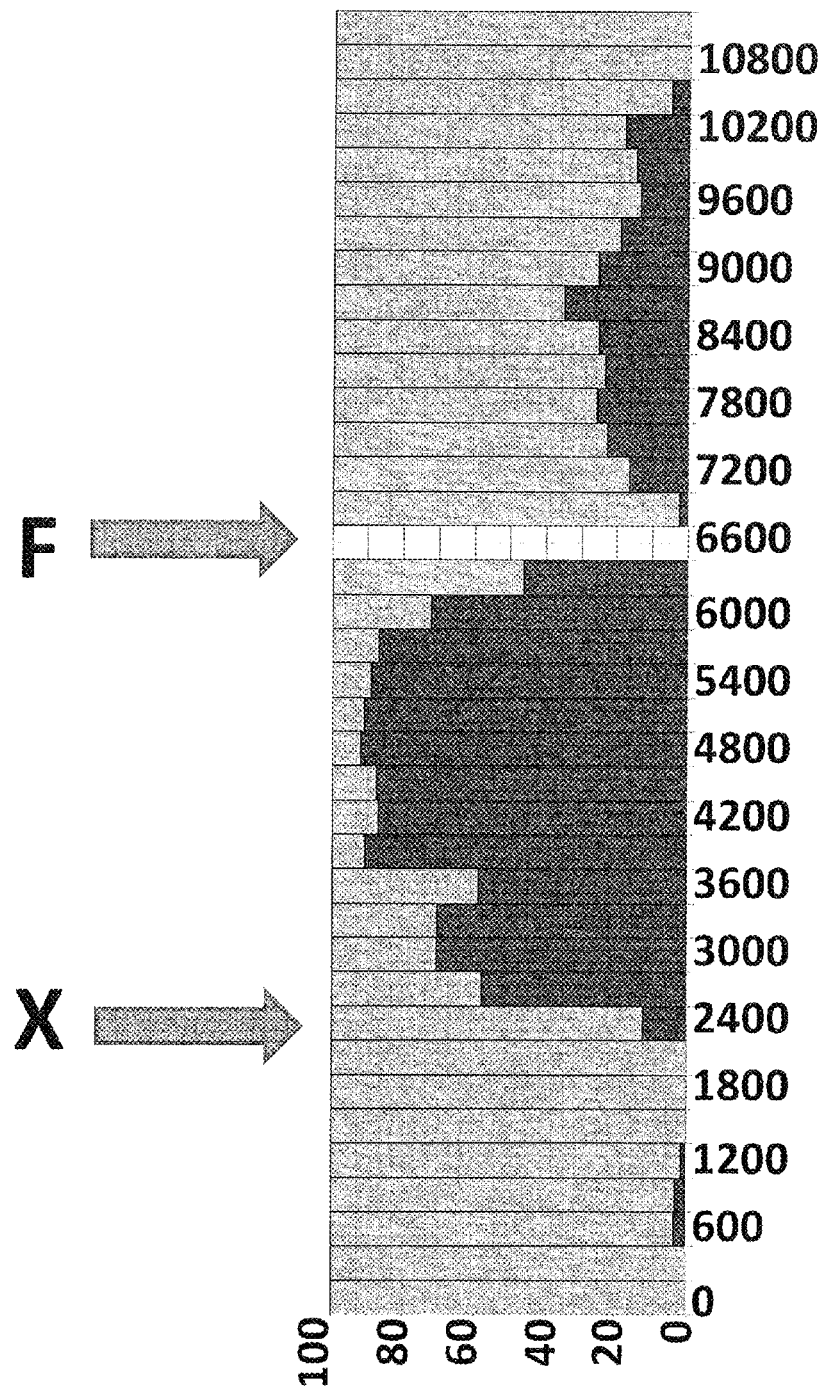
FIG. 5 shows part of the experimental time course (x-axis label=time (s), y-axis label=percentage (%)) with the percentage of time the nanopores are present in their unblocked state (shown as light grey) compared to when a helicase DNA movement was occurring and the nanopores were partially blocked by the DNA strand (shown as black). DNA construct X was added at 2400 seconds as indicated by the arrow labelled X. The 10 min methyl-β-cyclodextrin incubation and then flush (100 μM, 150 μL) was between 6600 and 6900 seconds as indicated by the arrow labelled F and shown as white boxes.
Figure 6:
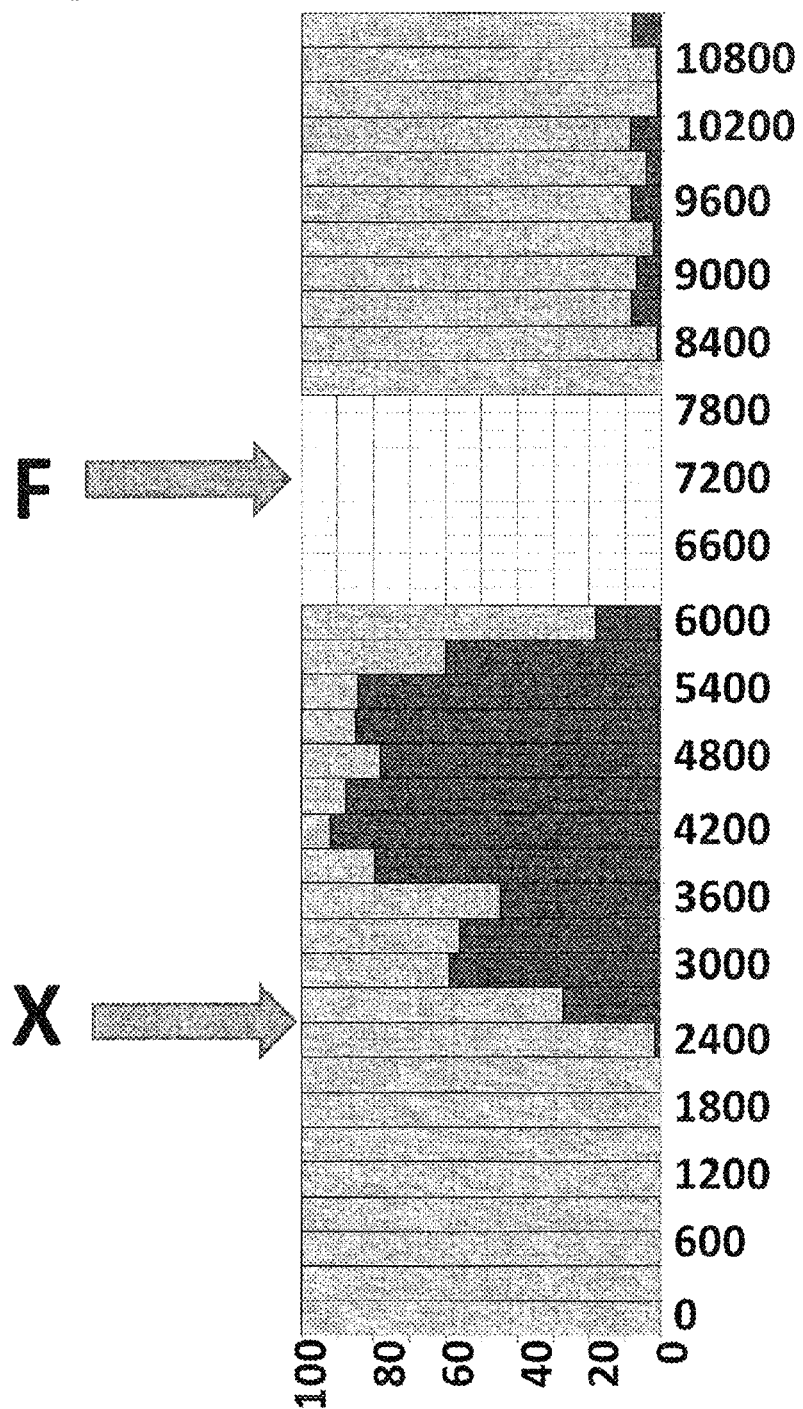
FIG. 6 shows part of the experimental time course (x-axis label=time (s), y-axis label=percentage (%)) with the percentage of time the nanopores are present in their unblocked state (shown as light grey) compared to when a helicase DNA movement was occurring and the nanopores were partially blocked by the DNA strand (shown as black). DNA construct X was added at 2400 seconds as indicated by the arrow labelled X. The 30 min methyl-β-cyclodextrin incubation and then flush (100 μM, 150 μL) was between 6300 and 8100 seconds as indicated by the arrow labelled F and shown as white boxes.

Helicase controlled DNA movement was observed for both DNA constructs X and Y, with T4 Dda-E94C/A360C. FIGS. 4, 5 and 6 show part of the experimental time course with the percentage of time the nanopores were present in their unblocked state (shown as light grey) compared to when a helicase DNA movement was occurring and the nanopores were partially blocked by the DNA strand (shown as black). FIGS. 4, 5 and 6 correspond to incubation periods of 1, 10 and 30 minutes with methyl-β-cyclodextrin respectively. For all three experiments, prior to addition of DNA, little or no helicase controlled DNA movements were observed. Upon the addition of construct X helicase controlled DNA movements were occurring through the nanopore around 80% of the time. After the addition of methyl-β-cyclodextrin for various incubation periods and the corresponding buffer flush, the percentage of time the nanopore was partially blocked owing to helicase controlled DNA movement was drastically reduced to around 20% and for the 30 minute incubation to less than 10%. This indicated that methyl-β-cyclodextrin successfully decoupled DNA, which had been coupled to a membrane using cholesterol, from the membrane. The methyl-β-cyclodextrin decoupled significantly more coupled DNA than flushing with buffer.

Upon the addition of DNA construct Y to the system, helicase controlled DNA movements which corresponded to construct Y were identified. A small proportion of movements were identified as corresponding to construct X, however, the proportion of events identified as X was significantly reduced in comparison to experiments where either construct X was not flushed from the system (see Example 2) or where tethered construct X was treated with 10 mL of buffer in an attempt to remove it from the system (see Example 3). The methyl-β-cyclodextrin decoupling process was repeated for construct Y and it was also shown that it was possible to successfully decouple construct Y from the membrane using this method.

Example 5

Figure 7:
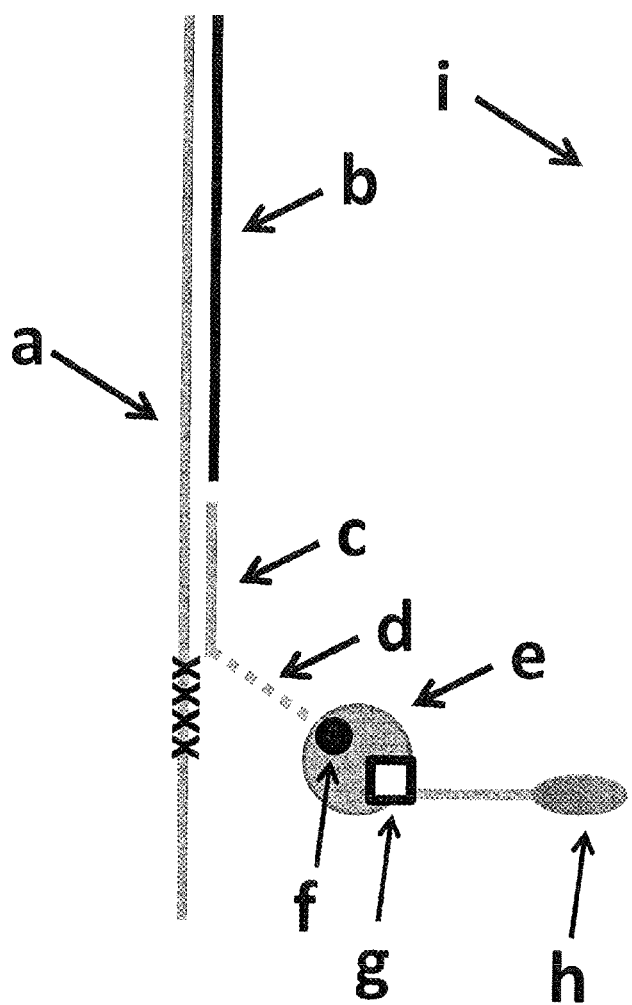
FIG. 7 shows how the DNA construct used in Example 5 was tethered to the membrane (labelled i). The strand of DNA which translocated through the nanopore is labelled a (SEQ ID NO: 42 attached at its 3' end to four iSpC3 spacers (labelled as crosses) which are attached at the opposite end to the 5' end of SEQ ID NO: 43). It was hybridised to two strands labelled b and c (SEQ ID NO: 44 and 45 respectively). SEQ ID NO: 45 was attached by its 3' end to six iSp18 spacers (labelled d and shown as a dotted line) which were attached at the opposite end to two thymines and a biotin group (labelled f). The biotin group was bound to streptavidin (labelled e) which also bound desthiobiotin (labelled g). Desthiobiotin was attached to the 5' end of SEQ ID NO: 46 which had a 3' cholesterol TEG (labelled h) at the opposite end.

This example illustrates how DNA, which has had a biotin-tether hybridised onto it and has been pre-incubated with streptavidin, has been coupled to the membrane by the streptavidin binding a 5' desthiobiotin of an extender (which also has a cholesterol at the 3' end) (see FIG. 7 for cartoon representation). This DNA construct can then be decoupled from the membrane by flushing the system, with free biotin. As biotin has a stronger binding affinity for streptavidin than desthiobiotin when the biotin was added to the system it out competed the desthiobiotin, which ensured efficient removal of the strand. This left the extenders coupled to the bilayer and available for coupling of a second DNA construct to the membrane.

Materials and Methods

The DNA construct used in Example 5 is shown in FIG. 7. The DNA construct was prepared by hybridising SEQ ID NO: 45 (50 nM, which has six iSp18 spacers attached to its 3' end which are attached at the opposite end to two thymines and a 3'biotin TEG) to the DNA strand which was made up of SEQ ID NO: 42 which is attached at its 3' end to four iSpC3 spacers which are attached at the opposite end to the 5' end of SEQ ID NO: 43 (50 nM) at 50° C. for ten minutes and then slow cooled. Streptavidin (final concentration 50 nM) was added to the DNA mixture (final concentration 25 nM) and incubated at room temperature for 10 minutes. This complex will be referred to as DNA construct P.

The nanopore experimental system was set up as described in Example 2. A control experiment was run, with no DNA added to the system for 15 minutes at an applied potential of 120 mV. The desthiobiotin extender (SEQ ID NO: 46 which has a desthiobiotin attached at the 5' end and a cholesterol TEG attached at the 3' end) was then added to the nanopore system and the experiment run for 15 mins allowing it to couple to the membrane. DNA construct P was added to the experimental system (25 nM) and the experiment run at an applied potential of 120 mV for 30 minutes. Free biotin (50 µM) was then added to the system and the experiment run for a further 30 minutes. After the biotin incubation, buffer was flowed through the system (1 mL, 625 mM KCl, 100 mM HEPES, pH8) to remove any excess biotin and de-coupled DNA.

Results and Discussion

Figure 8:
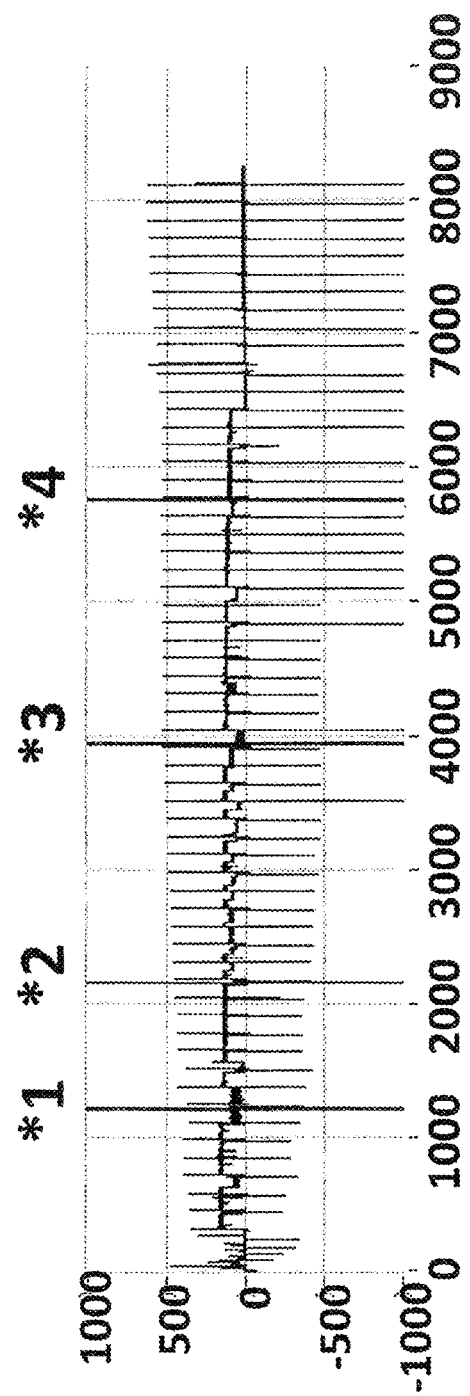
FIG. 8 shows the current trace (y-axis label=Current (pA), x-axis label=Time (s)) of the experiment described in Example 5. The trace shows the coupling steps and the removal of the coupled DNA using free biotin. *1 label corresponds to the addition of the desthiobiotin extender, *2 corresponds to the addition of DNA construct P, *3 corresponds to the addition of free biotin and *4 corresponds to the addition of the buffer flush.
Figure 9:
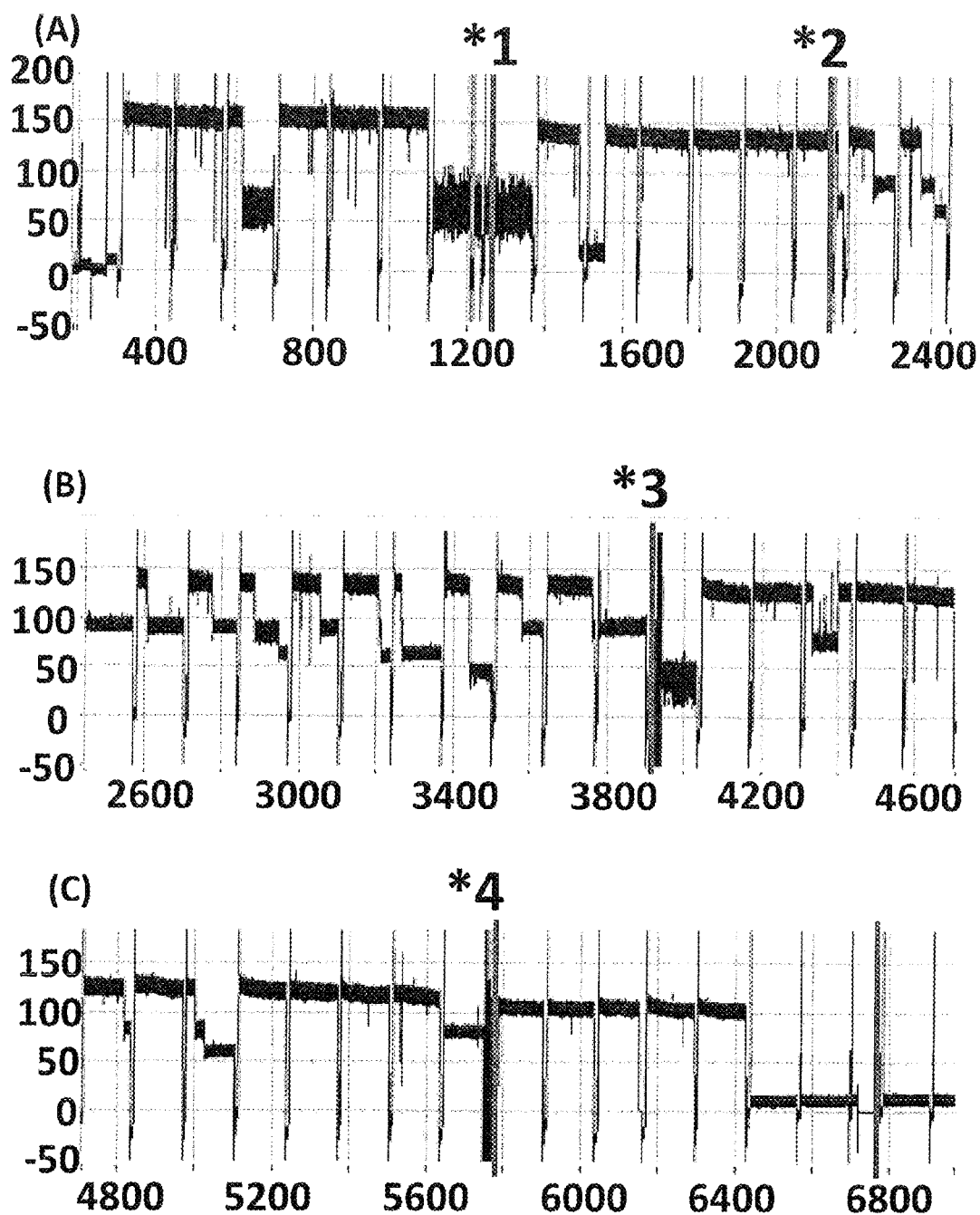
FIG. 9 shows three zoomed in regions of the current trace (all three traces have the following axes labels—y-axis label=Current (pA), x-axis label=Time (s)) shown in FIG. 8. Traces A, B and C are consecutive snap shots of part of the trace shown in FIG. 8. *1 label corresponds to the addition of the desthiobiotin extender, *2 corresponds to the addition of DNA construct P, *3 corresponds to the addition of free biotin and *4 corresponds to the addition of the buffer flush.

This experiment illustrates another method for de-coupling DNA constructs from a membrane. FIG. 8 shows the current trace of the full experiment described above. FIG. 9 shows several continuous snap shots of the experimental steps described previously. FIG. 9(A) initially shows that the nanopore was open and exhibited a couple of blocks when no DNA was present in the system. *1 marks the point in the experiment when the desthiobiotin extended was added to the system, current blocks corresponding to this short fragment were not observed. *2 marks the point where DNA construct P was added to the system. The addition of DNA resulted in DNA current blocks which were consistently between 70 and 100 pA (see FIG. 9A (last portion of the trace and 9B the first portion of the trace). *3 marks the point where biotin (50 µM) was added to the system. It was clear that upon addition of biotin there was a drastic reduction in the number of DNA current blocks observed. Finally, *4 corresponds to the buffer flush step where the DNA and biotin were removed from the system. This experiment illustrated that by flushing biotin into the system DNA construct P could be de-coupled from the membrane. As biotin has a stronger binding affinity for streptavidin than desthiobiotin when the biotin was added to the system it out competed the desthiobiotin, which ensured efficient removal of the strand. The biotin also bound to the other free binding sites on the streptavidin and the whole-streptavidin DNA complex was removed from the system. This left the extenders coupled to the bilayer and available for coupling of a second DNA construct to the membrane.

Example 6

This example illustrates how (2-hydroxypropyl)-β-cyclodextrin was used to decouple DNA, which was coupled to the membrane using a cholesterol TEG, from the membrane. Various different concentrations of (2-hydroxypropyl)-β-cyclodextrin were added to the nanopore system and the % change in the number of helicase controlled DNA movements that were detected per nanopore over a defined period was monitored. This experiment illustrated that concentrations as low as 20 mM (2-hydroxypropyl)-β-cyclodextrin resulted in a reduction in the number of helicase controlled DNA movements detected per nanopore, after incubation (see Table 2).

Materials and Methods

DNA construct X was prepared as described in Example 2. The DNA construct was pre-incubated with enzyme as described in Example 2 producing the construct X pre-mix.

The nanopore experimental system was set up as described in Example 2. DNA construct X/enzyme pre-mix (150 µL total) was added to the experimental system and the experiment run at a holding potential of 140 mV for two hours and helicase controlled DNA movement was monitored. After two hours, the experimental protocol was stopped, the potential set to zero and (2-hydroxypropyl)-β-cyclodextrin (150 µL of either 20 mM, 50 mM, 100 mM or 200 mM in 500 mM KCl, 25 mM K Phosphate pH8) was flowed onto the nanopore system and incubated for 10 minutes in order to try to remove coupled DNA construct X. After the incubation period, buffer (150 µL, 500 mM KCl, 25 mM K Phosphate pH8) was flushed through the system to remove any de-coupled DNA and excess (2-hydroxypropyl)-β-cyclodextrin. After the buffer flush, buffer (containing fuel) was added to the system (150 uL of 500 mM KCl, 25 mM K Phosphate 2 mM ATP, 2 mM MgCl2 pH8) with no additional DNA at a holding potential of 140 mV for two hours and helicase controlled DNA movement was monitored.

Results and Discussion

Helicase controlled DNA movement was observed for DNA construct X, with T4 Dda-E94C/A360C. Table 2 below shows the average % change in the number of helicase controlled DNA movements that were detected per nanopore, after the system had been incubated with (2-hydroxypropyl)-β-cyclodextrin at various concentrations. For all experiments, prior to addition of DNA, few or no helicase controlled DNA movements were observed. Upon the addition of construct X, helicase controlled DNA movements were occurring through the nanopore. After the addition of (2-hydroxypropyl)-β-cyclodextrin at various concentrations and the corresponding buffer flush, the average percentage change in the number of helicase controlled DNA movements that were detected per nanopore was at least 50% and was as much as 90% when incubated at 200 mM concentration. This indicated that (2-hydroxypropyl)-β-cyclodextrin successfully decoupled DNA, which had been coupled to a membrane using cholesterol, from the membrane.

TABLE 2

| Concentration | Reduction in the number of helicase controlled DNA movements detected (Average % change per nanopore) | |
|---|---|---|
| | Experiment 1 | Experiment 2 |
| 20 mM | −53.73 | −52.39 |
| 50 mM | −59.23 | −79.10 |
| 100 mM | −84.06 | −83.38 |
| 200 mM | −90.90 | −96.20 |

The invention claimed is:

1. A method for determining the presence, absence or one or more characteristics of two or more analytes in two or more samples, comprising:
   (a) coupling a first analyte in a first sample to a membrane using one or more anchors;
   (b) allowing the first analyte to interact with a nanopore present in the membrane and thereby determining the presence, absence or one or more characteristics of the first analyte;
   (c) uncoupling the first analyte of the first sample from the membrane;
   (d) after step (c), coupling a second analyte in a second sample to the membrane using one or more anchors, under conditions in which the first analyte of the first sample does not recouple to the membrane; and
   (e) allowing the second analyte of the second sample to interact with a nanopore in the membrane and thereby determining the presence, absence or one or more characteristics of the second analyte.

2. A method according to claim 1, wherein the one or more anchors comprise a polypeptide anchor and/or a hydrophobic anchor.

3. A method according to claim 2, wherein the hydrophobic anchor comprises a lipid, fatty acid, sterol, carbon nanotube or amino acid.

4. A method according to claim 1, wherein step (c) comprises uncoupling the first analyte of the first sample from the membrane by removing the one or more anchors from the membrane.

5. A method according to claim 4, wherein step (c) comprises contacting the one or more anchors with an agent which has a higher affinity for the one or more anchors than the anchors have for the membrane.

6. A method according to claim 5, wherein (i) the one or more anchors comprises cholesterol and the agent is a cyclodextrin or a derivative thereof or a lipid; (ii) the one or more anchors comprises streptavidin, biotin or desthiobiotin and the agent is biotin, desthiobiotin or streptavidin; or (iii) the one or more anchors comprises a protein and the agent is an antibody or fragment thereof which specifically binds to the protein.

7. A method according to claim 1, wherein step (c) comprises contacting the one or more anchors with an agent which reduces their ability to couple to the membrane.

8. A method according to claim 7, wherein (i) the one or more anchors comprises cholesterol and the agent is cholesterol dehydrogenase; (ii) the one or more anchors comprises a lipid and the agent is a phospholipase; or (iii) the one or more anchors comprises a protein and the agent is a proteinase or urea.

9. A method according to claim 1, wherein step (c) comprises uncoupling the first analyte of the first sample from the membrane by separating the first analyte from the one or more anchors.

10. A method according to claim 1, wherein step (c) comprises uncoupling the first analyte of the first sample from the membrane by contacting the first analyte and the one or more anchors with an agent which competes with the first analyte for binding to the one or more anchors.

11. A method according to claim 10, wherein the agent is a polynucleotide which competes with the first analyte of the first sample for hybridisation to the one or more anchors.

12. A method according to claim 9, wherein step (c) comprises (i) contacting the first analyte of the first sample and the one or more anchors with urea, tris(2-carboxyethyl) phosphine (TCEP), dithiothreitol (DTT), streptavidin or biotin, UV light, an enzyme or a binding agent; (ii) heating the first analyte and one or more anchors; or (iii) altering the pH.

13. A method according to claim 9, wherein step (d) comprises coupling the second analyte of the second sample to the membrane using the one or more anchors that were separated from the first analyte of the first sample.

14. A method according to claim 1, wherein between steps (c) and (d) the method comprises removing at least some of the first sample from the membrane.

15. A method according to claim 1, wherein the first analyte of the first sample and the second analyte of the second sample are polynucleotides and wherein the method is for identifying or estimating the sequence of the first polynucleotide of the first sample and/or the second polynucleotide of the second sample.

\* \* \* \* \*

SEQUENCE LISTING

```
<160> NUMBER OF SEQ ID NOS: 47

<210> SEQ ID NO 1
<211> LENGTH: 558
<212> TYPE: DNA
<213> ORGANISM: Artificial Sequence
<220> FEATURE:
<223> OTHER INFORMATION: Mycobacterium smegmatis porin A mutant
      (D90N/D91N/D93N/D118R/D134R/E193K)

<400> SEQUENCE: 1
atgggtctgg ataatgaact gagcctggtg gacggtcaag atcgtaccct gacggtgcaa        60
caatgggata cctttctgaa tggcgttttt ccgctggatc gtaatcgcct gacccgtgaa       120
tggtttcatt ccggtcgcgc aaaatatatc gtcgcaggcc cgggtgctga cgaattcgaa       180
ggcacgctgg aactgggtta tcagattggc tttccgtggt cactgggcgt tggtatcaac       240
ttctcgtaca ccacgccgaa tattctgatc aacaatggta acattaccgc accgccgttt       300
ggcctgaaca gcgtgattac gccgaacctg tttccgggtg ttagcatctc tgcccgtctg       360
ggcaatggtc cgggcattca agaagtggca acctttagtg tgcgcgtttc cggcgctaaa       420
```

-continued

```
ggcggtgtcg cggtgtctaa cgcccacggt accgttacgg gcgcggccgg cggtgtcctg    480
ctgcgtccgt tcgcgcgcct gattgcctct accggcgaca gcgttacgac ctatggcgaa    540
ccgtggaata tgaactaa                                                   558
```

<210> SEQ ID NO 2
<211> LENGTH: 184
<212> TYPE: PRT
<213> ORGANISM: Artificial Sequence
<220> FEATURE:
<223> OTHER INFORMATION: Mycobacterium smegmatis porin A mutant
       (D90N/D91N/D93N/D118R/D134R/E139K)

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
                100                 105                 110

Val Ser Ile Ser Ala Arg Leu Gly Asn Gly Pro Gly Ile Gln Glu Val
            115                 120                 125

Ala Thr Phe Ser Val Arg Val Ser Gly Ala Lys Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
                180
```

<210> SEQ ID NO 3
<211> LENGTH: 885
<212> TYPE: DNA
<213> ORGANISM: Artificial Sequence
<220> FEATURE:
<223> OTHER INFORMATION: alpha-hemolysin mutant (E111N/K147N)

<400> SEQUENCE: 3

```
atggcagatt ctgatattaa tattaaaacc ggtactacag atattggaag caatactaca     60
gtaaaaacag gtgatttagt cacttatgat aaagaaaatg gcatgcacaa aaaagtattt    120
tatagtttta tcgatgataa aaatcacaat aaaaaactgc tagttattag aacaaaaggt    180
accattgctg tcaatatag agtttatagc gaagaaggtg ctaacaaaag tggtttagcc    240
tggccttcag cctttaaggt acagttgcaa ctacctgata tgaagtagc tcaaatatct    300 gattactatc caagaaattc gattgataca aaaaactata tgagtacttt aacttatgga    360
ttcaacggta tgttactggt tgatgataca ggaaaaattg gcggcctta tggtgcaaat    420 gtttcgattg gtcatacact gaactatgtt caacctgatt tcaaaacaat tttagagagc    480
```

```
ccaactgata aaaaagtagg ctggaaagtg atatttaaca atatggtgaa tcaaaattgg      540
ggaccatacg atcgagattc ttggaacccg gtatatggca atcaactttt catgaaaact      600
agaaatggtt ctatgaaagc agcagataac ttccttgatc ctaacaaagc aagttctcta      660
ttatcttcag ggttttcacc agacttcgct acagttatta ctatggatag aaaagcatcc      720
aaacaacaaa caaatataga tgtaatatac gaacgagttc gtgatgatta ccaattgcat      780
tggacttcaa caaattggaa aggtaccaat actaaagata aatggacaga tcgttcttca      840
gaaagatata aaatcgattg ggaaaaagaa gaaatgacaa attaa                     885

<210> SEQ ID NO 4
<211> LENGTH: 293
<212> TYPE: PRT
<213> ORGANISM: Artificial Sequence
<220> FEATURE:
<223> OTHER INFORMATION: alpha-hemolysin mutant (E111N/K147N)

<400> SEQUENCE: 4

Ala Asp Ser Asp Ile Asn Ile Lys Thr Gly Thr Thr Asp Ile Gly Ser
1               5                  10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285
```

Glu Glu Met Thr Asn
    290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

```
Ala Thr Phe Ser Val Asp Val Ser Gly Pro Ala Gly Gly Val Ala Val
        130                 135                 140
Ser Asn Ala His Gly Thr Val Thr Gly Ala Ala Gly Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
            180
```

<210> SEQ ID NO 7
<211> LENGTH: 183
<212> TYPE: PRT
<213> ORGANISM: Mycobacterium smegmatis

<400> SEQUENCE: 7

```
Val Asp Asn Gln Leu Ser Val Val Asp Gly Gln Gly Arg Thr Leu Thr
1               5                   10                  15
Val Gln Gln Ala Glu Thr Phe Leu Asn Gly Val Phe Pro Leu Asp Arg
                20                  25                  30
Asn Arg Leu Thr Arg Glu Trp Phe His Ser Gly Arg Ala Thr Tyr His
            35                  40                  45
Val Ala Gly Pro Gly Ala Asp Glu Phe Glu Gly Thr Leu Glu Leu Gly
    50                  55                  60
Tyr Gln Val Gly Phe Pro Trp Ser Leu Gly Val Gly Ile Asn Phe Ser
65                  70                  75                  80
Tyr Thr Thr Pro Asn Ile Leu Ile Asp Gly Gly Asp Ile Thr Gln Pro
                85                  90                  95
Pro Phe Gly Leu Asp Thr Ile Ile Thr Pro Asn Leu Phe Pro Gly Val
            100                 105                 110
Ser Ile Ser Ala Asp Leu Gly Asn Gly Pro Gly Ile Gln Glu Val Ala
        115                 120                 125
Thr Phe Ser Val Asp Val Lys Gly Ala Lys Gly Ala Val Ala Val Ser
    130                 135                 140
Asn Ala His Gly Thr Val Thr Gly Ala Ala Gly Gly Val Leu Leu Arg
145                 150                 155                 160
Pro Phe Ala Arg Leu Ile Ala Ser Thr Gly Asp Ser Val Thr Thr Tyr
                165                 170                 175
Gly Glu Pro Trp Asn Met Asn
            180
```

<210> SEQ ID NO 8
<211> LENGTH: 1830
<212> TYPE: DNA
<213> ORGANISM: Bacillus subtilis phage phi29

<400> SEQUENCE: 8

```
atgaaacaca tgccgcgtaa aatgtatagc tgcgcgtttg aaaccacgac caaagtggaa      60
gattgtcgcg tttgggccta tggctacatg aacatcgaag atcattctga atacaaaatc    120
ggtaacagtc tggatgaatt tatggcatgg gtgctgaaag ttcaggcgga tctgtacttc    180
cacaacctga aatttgatgg cgcattcatt atcaactggc tggaacgtaa tggctttaaa    240
tggagcgcgg atggtctgcc gaacacgtat aataccatta tctctcgtat gggccagtgg    300
tatatgattg atatctgcct gggctacaaa ggtaaacgca aaattcatac cgtgatctat    360
gatagcctga aaaaactgcc gtttcgggta agaaaattg cgaaagattt caaactgacg    420
gttctgaaag gcgatattga ttatcacaaa gaacgtccgg ttggttacaa aatcacccg    480
```

-continued

```
gaagaatacg catacatcaa aaacgatatc cagatcatcg cagaagcgct gctgattcag    540
tttaaacagg gcctggatcg catgaccgcg ggcagtgata gcctgaaagg tttcaaagat    600
atcatcacga ccaaaaaatt caaaaaagtg ttcccgacgc tgagcctggg tctggataaa    660
gaagttcgtt atgcctaccg cggcggtttt acctggctga cgatcgtttc aaagaaaaa     720 gaaattggcg agggtatggt gtttgatgtt aatagtctgt atccggcaca gatgtacagc    780
cgcctgctgc gtatggcga accgatcgtg ttcgagggta aatatgtttg ggatgaagat     840
tacccgctgc atattcagca catccgttgt gaatttgaac tgaaagaagg ctatattccg    900
accattcaga tcaaacgtag tcgcttctat aagggtaacg aatacctgaa agctctggc     960 ggtgaaatcg cggatctgtg gctgagtaac gtggatctgg aactgatgaa agaacactac   1020
gatctgtaca cgttgaata catcagcggc ctgaaattta aagccacgac cggtctgttc    1080
aaagatttca tcgataaatg gacctacatc aaaacgacct ctgaaggcgc gattaaacag   1140
ctggccaaac tgatgctgaa cagcctgtat ggcaaattcg cctctaatcc ggatgtgacc   1200
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccggatgtg attaaagata tcgttgatcc gaaaaaactg   1440
ggttattggg cccacgaaag tacgtttaaa cgtgcaaaat acctgcgcca gaaaacctac   1500
atccaggata tctacatgaa agaagtggat ggcaaactgg ttgaaggttc tccggatgat   1560
tacaccgata tcaaattcag tgtgaaatgc gccggcatga cggataaaat caaaaaagaa   1620
gtgaccttcg aaaacttcaa agttggtttc agccgcaaaa tgaaaccgaa accggtgcag   1680
gttccgggcg gtgtggttct ggtggatgat acgtttacca ttaaatctgg cggtagtgcg   1740
tggagccatc cgcagttcga aaaggcggt ggctctggtg gcggttctgg cggtagtgcc    1800
tggagccacc cgcagtttga aaataataa                                     1830
```

<210> SEQ ID NO 9
<211> LENGTH: 608
<212> TYPE: PRT
<213> ORGANISM: Bacillus subtilis phage phi29

<400> SEQUENCE: 9

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125
```

-continued

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln

```
                    545                 550                 555                 560
Val Pro Gly Gly Val Val Leu Val Asp Asp Thr Phe Thr Ile Lys Ser
                565                 570                 575
Gly Gly Ser Ala Trp Ser His Pro Gln Phe Glu Lys Gly Gly Ser
                580                 585                 590
Gly Gly Gly Ser Gly Gly Ser Ala Trp Ser His Pro Gln Phe Glu Lys
            595                 600                 605
```

<210> SEQ ID NO 10
<211> LENGTH: 1390
<212> TYPE: DNA
<213> ORGANISM: Escherichia coli

<400> SEQUENCE: 10

```
atgatgaacg atggcaaaca gcagagcacc ttcctgtttc atgattatga aaccttcggt     60
acccatccgg ccctggatcg tccggcgcag tttgcggcca ttcgcaccga tagcgaattc    120
aatgtgattg cgaaccggaa agtgttttat gcaaaccggc cgatgattaa tctgccgcag    180
ccgggtgcgg tgctgattac cggtattacc ccgcaggaag cgcgcgcgaa aggtgaaaac    240
gaagcggcgt ttgccgcgcg cattcatagc ctgtttaccg tgccgaaaac ctgcattctg    300
ggctataaca atgtgcgctt cgatgatgaa gttacccgta atatctttta tcgtaacttt    360
tatgatccgt atgcgtggag ctggcagcat gataacagcc gttgggatct gctggatgtg    420
atgcgcgcgt gctatgcgct cgcccggaa ggcattaatt ggccggaaaa cgatgatggc    480
ctgccgagct ttcgtctgga acatctgacc aaagccaacg gcattgaaca tagcaatgcc    540
catgatgcga tggccgatgt ttatgcgacc attgcgatgg cgaaactggt taaaacccgt    600
cagccgcgcc tgtttgatta tctgtttacc caccgtaaca acacaaaact gatggcgctg    660
attgatgttc gcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg ggcgataatg ccgccgtgcc ggtgaaactg    900
gttcacatta caaatgccc ggtgctggcc caggcgaaca ccctgcgccc ggaagatgcg    960
gatcgtctgg gtattaatcg ccagcattgt ctggataatc tgaaaatcct gcgtgaaaac   1020
ccgcaggtgc gtgaaaaagt ggtggcgatc ttcgcggaag cggaaccgtt caccccgagc   1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc                                                          1390
```

<210> SEQ ID NO 11
<211> LENGTH: 485
<212> TYPE: PRT
<213> ORGANISM: Escherichia coli

<400> SEQUENCE: 11

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
```

```
                    20                  25                  30
Ala Ile Arg Thr Asp Ser Glu Phe Asn Val Ile Gly Glu Pro Glu Val
                35                  40                  45
Phe Tyr Cys Lys Pro Ala Asp Asp Tyr Leu Pro Gln Pro Gly Ala Val
        50                  55                  60
Leu Ile Thr Gly Ile Thr Pro Gln Glu Ala Arg Ala Lys Gly Glu Asn
 65                  70                  75                  80
Glu Ala Ala Phe Ala Ala Arg Ile His Ser Leu Phe Thr Val Pro Lys
                85                  90                  95
Thr Cys Ile Leu Gly Tyr Asn Asn Val Arg Phe Asp Asp Glu Val Thr
                100                 105                 110
Arg Asn Ile Phe Tyr Arg Asn Phe Tyr Asp Pro Tyr Ala Trp Ser Trp
                115                 120                 125
Gln His Asp Asn Ser Arg Trp Asp Leu Leu Asp Val Met Arg Ala Cys
                130                 135                 140
Tyr Ala Leu Arg Pro Glu Gly Ile Asn Trp Pro Glu Asn Asp Asp Gly
145                 150                 155                 160
Leu Pro Ser Phe Arg Leu Glu His Leu Thr Lys Ala Asn Gly Ile Glu
                165                 170                 175
His Ser Asn Ala His Asp Ala Met Ala Asp Val Tyr Ala Thr Ile Ala
                180                 185                 190
Met Ala Lys Leu Val Lys Thr Arg Gln Pro Arg Leu Phe Asp Tyr Leu
                195                 200                 205
Phe Thr His Arg Asn Lys His Lys Leu Met Ala Leu Ile Asp Val Pro
                210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
                260                 265                 270
Glu Leu Asp Ser Asp Thr Leu Arg Glu Arg Leu Tyr Thr Ala Lys Thr
                275                 280                 285
Asp Leu Gly Asp Asn Ala Ala Val Pro Val Lys Leu Val His Ile Asn
                290                 295                 300
Lys Cys Pro Val Leu Ala Gln Ala Asn Thr Leu Arg Pro Glu Asp Ala
305                 310                 315                 320
Asp Arg Leu Gly Ile Asn Arg Gln His Cys Leu Asp Asn Leu Lys Ile
                325                 330                 335
Leu Arg Glu Asn Pro Gln Val Arg Glu Lys Val Val Ala Ile Phe Ala
                340                 345                 350
Glu Ala Glu Pro Phe Thr Pro Ser Asp Asn Val Asp Ala Gln Leu Tyr
                355                 360                 365
Asn Gly Phe Phe Ser Asp Ala Asp Arg Ala Ala Met Lys Ile Val Leu
                370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
                420                 425                 430
Gln Val Phe Thr Pro Glu Phe Leu Gln Gly Tyr Ala Asp Glu Leu Gln
                435                 440                 445
```

Met Leu Val Gln Gln Tyr Ala Asp Asp Lys Glu Lys Val Ala Leu Leu
    450                 455                 460
Lys Ala Leu Trp Gln Tyr Ala Glu Glu Ile Val Ser Gly Ser Gly His
465                 470                 475                 480
His His His His His
            485

<210> SEQ ID NO 12
<211> LENGTH: 804
<212> TYPE: DNA
<213> ORGANISM: Escherichia coli

<400> SEQUENCE: 12
atgaaatttg tctcttttaa tatcaacggc ctgcgcgcca gacctcacca gcttgaagcc     60
atcgtcgaaa agcaccaacc ggatgtgatt ggcctgcagg agacaaaagt tcatgacgat    120
atgtttccgc tcgaagaggt ggcgaagctc ggctacaacg tgttttatca cgggcagaaa    180
ggccattatg gcgtggcgct gctgaccaaa gagacgccga ttgccgtgcg tcgcggcttt    240
cccggtgacg acgaagaggc gcagcggcgg attattatgg cggaaatccc ctcactgctg    300
ggtaatgtca ccgtgatcaa cggttacttc ccgcagggtg aaagccgcga ccatccgata    360
aaattcccgg caaaagcgca gttttatcag aatctgcaaa actacctgga aaccgaactc    420
aaacgtgata atccggtact gattatgggc gatatgaata tcagccctac agatctggat    480
atcggcattg gcgaagaaaa ccgtaagcgc tggctgcgta ccggtaaatg ctctttcctg    540
ccggaagagc gcgaatggat ggacaggctg atgagctggg ggttggtcga taccttccgc    600
catgcgaatc cgcaaacagc agatcgtttc tcatggtttg attaccgctc aaaaggtttt    660
gacgataacc gtggtctgcg catcgacctg ctgctcgcca gccaaccgct ggcagaatgt    720
tgcgtagaaa ccggcatcga ctatgaaatc cgcagcatgg aaaaaccgtc cgatcacgcc    780
cccgtctggg cgaccttccg ccgc                                          804

<210> SEQ ID NO 13
<211> LENGTH: 268
<212> TYPE: PRT
<213> ORGANISM: Escherichia coli

<400> SEQUENCE: 13

Met Lys Phe Val Ser Phe Asn Ile Asn Gly Leu Arg Ala Arg Pro His
1               5                   10                  15
Gln Leu Glu Ala Ile Val Glu Lys His Gln Pro Asp Val Ile Gly Leu
            20                  25                  30
Gln Glu Thr Lys Val His Asp Asp Met Phe Pro Leu Glu Glu Val Ala
        35                  40                  45
Lys Leu Gly Tyr Asn Val Phe Tyr His Gly Gln Lys Gly His Tyr Gly
    50                  55                  60
Val Ala Leu Leu Thr Lys Glu Thr Pro Ile Ala Val Arg Arg Gly Phe
65                  70                  75                  80
Pro Gly Asp Asp Glu Glu Ala Gln Arg Arg Ile Ile Met Ala Glu Ile
            85                  90                  95
Pro Ser Leu Leu Gly Asn Val Thr Val Ile Asn Gly Tyr Phe Pro Gln
            100                 105                 110
Gly Glu Ser Arg Asp His Pro Ile Lys Phe Pro Ala Lys Ala Gln Phe
        115                 120                 125
Tyr Gln Asn Leu Gln Asn Tyr Leu Glu Thr Glu Leu Lys Arg Asp Asn

| | | 130 | | | 135 | | | 140 | | | |
|---|---|---|---|---|---|---|---|---|---|---|---|
| Pro | Val | Leu | Ile | Met | Gly | Asp | Met | Asn | Ile | Ser | |
| 145 | | | | 150 | | | | 155 | | | |

Pro Thr Asp Leu Asp
160

Ile Gly Ile Gly Glu Glu Asn Arg Lys Arg Trp Leu Arg Thr Gly Lys
          165                   170                   175

Cys Ser Phe Leu Pro Glu Glu Arg Glu Trp Met Asp Arg Leu Met Ser
          180                   185                   190

Trp Gly Leu Val Asp Thr Phe Arg His Ala Asn Pro Gln Thr Ala Asp
      195                  200                   205

Arg Phe Ser Trp Phe Asp Tyr Arg Ser Lys Gly Phe Asp Asp Asn Arg
    210                  215                  220

Gly Leu Arg Ile Asp Leu Leu Leu Ala Ser Gln Pro Leu Ala Glu Cys
225                   230                   235                   240

Cys Val Glu Thr Gly Ile Asp Tyr Glu Ile Arg Ser Met Glu Lys Pro
          245                   250                   255

Ser Asp His Ala Pro Val Trp Ala Thr Phe Arg Arg
          260                   265

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat cgtgttcac      120
ggcgactatg atgcggatgg cctgaccggc accgcgatcc tggttcgtgg tctggccgcc     180
ctgggtgcga tgttcatcc gtttatcccg caccgcctgg aagaaggcta tggtgtcctg      240
atggaacgcg tcccggaaca tctggaagcc tcggacctgt ttctgaccgt tgactgcggc     300
attaccaacc atgcggaact gcgcgaactg ctggaaaatg cgtggaagt cattgttacc      360
gatcatcata cgccgggcaa aacgccgccg ccgggtctgg tcgtgcatcc ggcgctgacg     420
ccggatctga agaaaaaacc gaccggcgca ggcgtggcgt ttctgctgct gtgggcactg     480
catgaacgcc tgggcctgcc gccgccgctg aatacgcgg acctggcagc cgttggcacc     540
attgccgacg ttgccccgct gtggggttgg aatcgtgcac tggtgaaaga aggtctggca     600
cgcatcccgg cttcatcttg ggtgggcctg cgtctgctgg ctgaagccgt gggctatacc     660
ggcaaagcgg tcgaagtcgc tttccgcatc gcgccgcgca tcaatgcggc ttcccgcctg     720
ggcgaagcgg aaaaagccct gcgcctgctg ctgacggatg atgcggcaga gctcaggcg      780
ctggtcggcg aactgcaccg tctgaacgcc gtcgtcaga ccctgaaga agcgatgctg       840
cgcaaactgc tgccgcaggc cgacccggaa gcgaaagcca tcgttctgct ggacccggaa     900
ggccatccgg tgttatggg tattgtggcc tctcgcatcc tggaagcgac cctgcgcccg     960
gtctttctgt ggcccagggg caaaggcacc gtgcgttcgc tggctccgat ttccgccgtc    1020
gaagcactgc gcagcgcgga agatctgctg ctgcgttatg gtggtcataa agaagcggcg    1080
ggtttcgcaa tggatgaagc gctgtttccg gcgttcaaag cacgcgttga agcgtatgcc    1140
gcacgtttcc cggatccggt tcgtgaagtg gcactgctgg atctgctgcc ggaaccgggc    1200
ctgctgccgc aggtgttccg tgaactggca ctgctggaac cgtatggtga aggtaacccg    1260
gaaccgctgt tcctg                                                     1275
```

```
<210> SEQ ID NO 15
<211> LENGTH: 425
<212> TYPE: PRT
<213> ORGANISM: Thermus thermophilus

<400> SEQUENCE: 15

Met Phe Arg Arg Lys Glu Asp Leu Asp Pro Pro Leu Ala Leu Leu Pro
1               5                   10                  15

Leu Lys Gly Leu Arg Glu Ala Ala Leu Leu Glu Glu Ala Leu Arg
            20                  25                  30

Gln Gly Lys Arg Ile Arg Val His Gly Asp Tyr Asp Ala Asp Gly Leu
            35                  40                  45

Thr Gly Thr Ala Ile Leu Val Arg Gly Leu Ala Ala Leu Gly Ala Asp
        50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380
```

```
Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
            405                 410                 415

Glu Gly Asn Pro Glu Pro Leu Phe Leu
        420                 425
```

<210> SEQ ID NO 16
<211> LENGTH: 738
<212> TYPE: DNA
<213> ORGANISM: Bacteriophage lambda

<400> SEQUENCE: 16

```
tccggaagcg gctctggtag tggttctggc atgacaccgg acattatcct gcagcgtacc    60
gggatcgatg tgagagctgt cgaacagggg gatgatgcgt ggcacaaatt acggctcggc   120
gtcatcaccg cttcagaagt tcacaacgtg atagcaaaac cccgctccgg aaagaagtgg   180
cctgacatga aaatgtccta cttccacacc ctgcttgctg aggtttgcac cggtgtggct   240
ccggaagtta acgctaaagc actggcctgg ggaaaacagt acgagaacga cgccagaacc   300
ctgtttgaat tcacttccgg cgtgaatgtt actgaatccc cgatcatcta tcgcgacgaa   360
agtatgcgta ccgcctgctc tcccgatggt ttatgcagtg acggcaacgg ccttgaactg   420
aaatgcccgt ttacctcccg ggatttcatg aagttccggc tcggtggttt cgaggccata   480
aagtcagctt acatggccca ggtgcagtac agcatgtggg tgacgcgaaa aaatgcctgg   540
tactttgcca actatgaccc gcgtatgaag cgtgaaggcc tgcattatgt cgtgattgag   600
cgggatgaaa agtacatggc gagttttgac gagatcgtgc cggagttcat cgaaaaaatg   660
gacgaggcac tggctgaaat tggttttgta tttggggagc aatggcgatc tggctctggt   720
tccggcagcg gttccgga                                                738
```

<210> SEQ ID NO 17
<211> LENGTH: 226
<212> TYPE: PRT
<213> ORGANISM: Bacteriophage lambda

<400> SEQUENCE: 17

```
Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
```

```
                145                 150                 155                 160
Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
                180                 185                 190

Glu Lys Tyr Met Ala Ser Phe Asp Glu Ile Val Pro Glu Phe Ile Glu
                195                 200                 205

Lys Met Asp Glu Ala Leu Ala Glu Ile Gly Phe Val Phe Gly Glu Gln
                210                 215                 220

Trp Arg
225

<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
                20                  25                  30

Glu Met Gly Leu Leu Glu Lys Lys Asn Leu Leu Ala Ala Ile Pro Thr
            35                  40                  45

Ala Ser Gly Lys Thr Leu Leu Ala Glu Leu Ala Met Ile Lys Ala Ile
        50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
                100                 105                 110

Val Asn Asp Ile Ile Val Ala Thr Ser Glu Lys Thr Asp Ser Leu Leu
            115                 120                 125

Arg Asn Gly Thr Ser Trp Met Asp Glu Ile Thr Thr Val Val Val Asp
        130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
                180                 185                 190

Ala Ala Leu Val Leu Ser Glu Trp Arg Pro Thr Asp Leu His Glu Gly
            195                 200                 205

Val Leu Phe Gly Asp Ala Ile Asn Phe Pro Gly Ser Gln Lys Lys Ile
        210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
                260                 265                 270

Asn Asp Ile Met Ile Lys Leu Ala Gly Ile Ala Glu Glu Val Glu Ser
            275                 280                 285
```

```
Thr Gly Glu Thr Asp Thr Ala Ile Val Leu Ala Asn Cys Ile Arg Lys
    290             295                 300

Gly Val Ala Phe His His Ala Gly Leu Asn Ser Asn His Arg Lys Leu
305             310              315                 320

Val Glu Asn Gly Phe Arg Gln Asn Leu Ile Lys Val Ile Ser Ser Thr
                325             330                 335

Pro Thr Leu Ala Ala Gly Leu Asn Leu Pro Ala Arg Arg Val Ile Ile
            340             345             350

Arg Ser Tyr Arg Arg Phe Asp Ser Asn Phe Gly Met Gln Pro Ile Pro
    355             360             365

Val Leu Glu Tyr Lys Gln Met Ala Gly Arg Ala Gly Arg Pro His Leu
    370             375             380

Asp Pro Tyr Gly Glu Ser Val Leu Leu Ala Lys Thr Tyr Asp Glu Phe
385             390             395                 400

Ala Gln Leu Met Glu Asn Tyr Val Glu Ala Asp Ala Glu Asp Ile Trp
            405             410             415

Ser Lys Leu Gly Thr Glu Asn Ala Leu Arg Thr His Val Leu Ser Thr
            420             425             430

Ile Val Asn Gly Phe Ala Ser Thr Arg Gln Glu Leu Phe Asp Phe Phe
        435             440             445

Gly Ala Thr Phe Phe Ala Tyr Gln Gln Asp Lys Trp Met Leu Glu Glu
    450             455             460

Val Ile Asn Asp Cys Leu Glu Phe Leu Ile Asp Lys Ala Met Val Ser
465             470             475                 480

Glu Thr Glu Asp Ile Glu Asp Ala Ser Lys Leu Phe Leu Arg Gly Thr
            485             490             495

Arg Leu Gly Ser Leu Val Ser Met Leu Tyr Ile Asp Pro Leu Ser Gly
        500             505             510

Ser Lys Ile Val Asp Gly Phe Lys Asp Ile Gly Lys Ser Thr Gly Gly
    515             520             525

Asn Met Gly Ser Leu Glu Asp Asp Lys Gly Asp Asp Ile Thr Val Thr
    530             535             540

Asp Met Thr Leu Leu His Leu Val Cys Ser Thr Pro Asp Met Arg Gln
545             550             555                 560

Leu Tyr Leu Arg Asn Thr Asp Tyr Thr Ile Val Asn Glu Tyr Ile Val
            565             570             575

Ala His Ser Asp Glu Phe His Glu Ile Pro Asp Lys Leu Lys Glu Thr
        580             585             590

Asp Tyr Glu Trp Phe Met Gly Glu Val Lys Thr Ala Met Leu Leu Glu
    595             600             605

Glu Trp Val Thr Glu Val Ser Ala Glu Asp Ile Thr Arg His Phe Asn
    610             615             620

Val Gly Glu Gly Asp Ile His Ala Leu Ala Asp Thr Ser Glu Trp Leu
625             630             635                 640

Met His Ala Ala Lys Leu Ala Glu Leu Leu Gly Val Glu Tyr Ser
            645             650             655

Ser His Ala Tyr Ser Leu Glu Lys Arg Ile Arg Tyr Gly Ser Gly Leu
        660             665             670

Asp Leu Met Glu Leu Val Gly Ile Arg Gly Val Gly Arg Val Arg Ala
    675             680             685

Arg Lys Leu Tyr Asn Ala Gly Phe Val Ser Val Ala Lys Leu Lys Gly
    690             695             700

Ala Asp Ile Ser Val Leu Ser Lys Leu Val Gly Pro Lys Val Ala Tyr
```

```
                705                 710                 715                 720
Asn Ile Leu Ser Gly Ile Gly Val Arg Val Asn Asp Lys His Phe Asn
                    725                 730                 735

Ser Ala Pro Ile Ser Ser Asn Thr Leu Asp Thr Leu Leu Asp Lys Asn
                    740                 745                 750

Gln Lys Thr Phe Asn Asp Phe Gln
                    755                 760

<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
                20                  25                  30

Lys Ala Gly Leu Thr Asp Gly Lys Ser Val Leu Val Ser Ala Pro Thr
            35                  40                  45

Ala Ser Gly Lys Thr Leu Ile Ala Ala Ile Ala Met Ile Ser His Leu
        50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Ile Pro Leu
                85                  90                  95

Gly Arg Pro Val Arg Val Gly Val Ser Thr Gly Asp Phe Glu Lys Ala
                100                 105                 110

Gly Arg Ser Leu Gly Asn Asn Asp Ile Leu Val Leu Thr Asn Glu Arg
            115                 120                 125

Met Asp Ser Leu Ile Arg Arg Pro Asp Trp Met Asp Glu Val Gly
        130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
305                 310                 315                 320
```

-continued

Gln Asp Cys Arg Ser Val Glu Glu Phe Arg Ser Gly Arg Ile
            325                 330                 335

Arg Leu Leu Ala Ser Thr Pro Thr Leu Ala Ala Gly Val Asn Leu Pro
        340                 345                 350

Ala Arg Arg Val Val Ile Ser Ser Val Met Arg Tyr Asn Ser Ser Ser
    355                 360                 365

Gly Met Ser Glu Pro Ile Ser Ile Leu Glu Tyr Lys Gln Leu Cys Gly
370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Glu Ser Gly Asp Val His Arg Met Val
        595                 600                 605

Glu Ser Ser Gly Trp Leu Leu Arg Cys Ile Trp Glu Ile Ser Lys His
    610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
        675                 680                 685

Glu Gly Ile Gly Ala Thr Leu Ala Asn Asn Ile Lys Ser Gln Leu Arg
    690                 695                 700

Lys Gly Gly
705

<210> SEQ ID NO 20
<211> LENGTH: 720
<212> TYPE: PRT

<213> ORGANISM: Thermococcus gammatolerans

<400> SEQUENCE: 20

```
Met Lys Val Asp Glu Leu Pro Val Asp Glu Arg Leu Lys Ala Val Leu
1               5                   10                  15
Lys Glu Arg Gly Ile Glu Glu Leu Tyr Pro Pro Gln Ala Glu Ala Leu
            20                  25                  30
Lys Ser Gly Ala Leu Glu Gly Arg Asn Leu Val Leu Ala Ile Pro Thr
        35                  40                  45
Ala Ser Gly Lys Thr Leu Val Ser Glu Ile Val Met Val Asn Lys Leu
    50                  55                  60
Ile Gln Glu Gly Gly Lys Ala Val Tyr Leu Val Pro Leu Lys Ala Leu
65                  70                  75                  80
Ala Glu Glu Lys Tyr Arg Glu Phe Lys Glu Trp Glu Lys Leu Gly Leu
                85                  90                  95
Lys Val Ala Ala Thr Gly Asp Tyr Asp Ser Thr Asp Asp Trp Leu
            100                 105                 110
Gly Arg Tyr Asp Ile Ile Val Ala Thr Ala Glu Lys Phe Asp Ser Leu
        115                 120                 125
Leu Arg His Gly Ala Arg Trp Ile Asn Asp Val Lys Leu Val Val Ala
    130                 135                 140
Asp Glu Val His Leu Ile Gly Ser Tyr Asp Arg Gly Ala Thr Leu Glu
145                 150                 155                 160
Met Ile Leu Thr His Met Leu Gly Arg Ala Gln Ile Leu Ala Leu Ser
                165                 170                 175
Ala Thr Val Gly Asn Ala Glu Glu Leu Ala Glu Trp Leu Asp Ala Ser
            180                 185                 190
Leu Val Val Ser Asp Trp Arg Pro Val Gln Leu Arg Arg Gly Val Phe
        195                 200                 205
His Leu Gly Thr Leu Ile Trp Glu Asp Gly Lys Val Glu Ser Tyr Pro
    210                 215                 220
Glu Asn Trp Tyr Ser Leu Val Val Asp Ala Val Lys Arg Gly Lys Gly
225                 230                 235                 240
Ala Leu Val Phe Val Asn Thr Arg Arg Ser Ala Glu Lys Glu Ala Leu
                245                 250                 255
Ala Leu Ser Lys Leu Val Ser Ser His Leu Thr Lys Pro Glu Lys Arg
            260                 265                 270
Ala Leu Glu Ser Leu Ala Ser Gln Leu Glu Asp Asn Pro Thr Ser Glu
        275                 280                 285
Lys Leu Lys Arg Ala Leu Arg Gly Gly Val Ala Phe His His Ala Gly
    290                 295                 300
Leu Ser Arg Val Glu Arg Thr Leu Ile Glu Asp Ala Phe Arg Glu Gly
305                 310                 315                 320
Leu Ile Lys Val Ile Thr Ala Thr Pro Thr Leu Ser Ala Gly Val Asn
                325                 330                 335
Leu Pro Ser Phe Arg Val Ile Ile Arg Asp Thr Lys Arg Tyr Ala Gly
            340                 345                 350
Phe Gly Trp Thr Asp Ile Pro Val Leu Glu Ile Gln Gln Met Met Gly
        355                 360                 365
Arg Ala Gly Arg Pro Arg Tyr Asp Lys Tyr Gly Glu Ala Ile Ile Val
    370                 375                 380
Ala Arg Thr Asp Glu Pro Gly Lys Leu Met Glu Arg Tyr Ile Arg Gly
385                 390                 395                 400
```

```
Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
    450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Glu Met Glu Asp Tyr Leu Asp Leu Ala Tyr
    530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Leu Glu Leu Ala Asp Trp Leu
        595                 600                 605

Met Tyr Ser Leu Ile Glu Leu Tyr Lys Leu Phe Glu Pro Lys Glu Glu
    610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
        675                 680                 685

Lys Ile Leu Asp Gly Ile Tyr Arg His Leu Gly Ile Glu Lys Arg Val
    690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60
```

```
Ala Ala Gly Gly Lys Cys Leu Tyr Ile Val Pro Leu Arg Ala Leu Ala
 65                  70                  75                  80

Ser Glu Lys Tyr Asp Glu Phe Ser Lys Lys Gly Val Ile Arg Val Gly
                 85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
                245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
        275                 280                 285

Asn Val Leu Ala Asp Cys Val Glu Arg Gly Ala Ala Phe His His Ala
    290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
    370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480
```

```
Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
            515                 520                 525

Arg Leu Tyr Leu Lys Ala Asp Thr Gln Leu Leu Arg Thr Phe Leu
            530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
            595                 600                 605

Leu His Gly Thr Glu Arg Leu Val Ser Val Glu Met Pro Glu Met Ser
            610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
            675                 680                 685

Gln Val Ile Asp Glu Ile Thr Gly Val Lys Arg Ser Gly Ile His Ser
            690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
            755                 760                 765

Ser Glu Lys Glu Asn Ser Ser Asp Lys Thr Glu Glu Ile Pro Asp
770                 775                 780

Thr Gln Lys Ile Arg Gly Gln Ser Ser Trp Glu Asp Phe Gly Cys
785                 790                 795

<210> SEQ ID NO 22
<211> LENGTH: 1756
<212> TYPE: PRT
<213> ORGANISM: Escherichia coli

<400> SEQUENCE: 22

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
            35                  40                  45

Lys Asp Val Phe Thr Arg Leu Leu Glu Gly Arg Leu Pro Asp Gly Ala
        50                  55                  60
```

```
Asp Leu Ser Arg Met Gln Asp Gly Ser Asn Lys His Arg Pro Gly Tyr
 65                  70                  75                  80

Asp Leu Thr Phe Ser Ala Pro Lys Ser Val Ser Met Met Ala Met Leu
             85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
            115                 120                 125

Gly Gln Ser Glu Thr Val Leu Thr Gly Asn Leu Val Met Ala Leu Phe
130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
            195                 200                 205

Glu Ala Leu Gly Tyr Glu Thr Glu Val Val Gly Lys His Gly Met Trp
210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
            275                 280                 285

Arg Ala Tyr Arg Asp Ala Ala Asp Gln Arg Thr Glu Ile Arg Thr Gln
290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
            355                 360                 365

Gln Leu Ile Pro Leu Asp Arg Glu Lys Gly Leu Phe Thr Ser Gly Ile
370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
            435                 440                 445

Val Ala Glu Leu Val Met Met Ala Arg Glu Gln Gly Arg Glu Val Gln
            450                 455                 460

Ile Ile Ala Ala Asp Arg Arg Ser Gln Met Asn Leu Lys Gln Asp Glu
465                 470                 475                 480
```

-continued

```
Arg Leu Ser Gly Glu Leu Ile Thr Gly Arg Gln Leu Leu Glu Gly
                485                 490                 495
Met Ala Phe Thr Pro Gly Ser Thr Val Ile Val Asp Gln Gly Glu Lys
            500                 505                 510
Leu Ser Leu Lys Glu Thr Leu Thr Leu Leu Asp Gly Ala Ala Arg His
        515                 520                 525
Asn Val Gln Val Leu Ile Thr Asp Ser Gly Gln Arg Thr Gly Thr Gly
    530                 535                 540
Ser Ala Leu Met Ala Met Lys Asp Ala Gly Val Asn Thr Tyr Arg Trp
545                 550                 555                 560
Gln Gly Gly Glu Gln Arg Pro Ala Thr Ile Ile Ser Glu Pro Asp Arg
                565                 570                 575
Asn Val Arg Tyr Ala Arg Leu Ala Gly Asp Phe Ala Ala Ser Val Lys
            580                 585                 590
Ala Gly Glu Glu Ser Val Ala Gln Val Ser Gly Val Arg Glu Gln Ala
        595                 600                 605
Ile Leu Thr Gln Ala Ile Arg Ser Glu Leu Lys Thr Gln Gly Val Leu
    610                 615                 620
Gly His Pro Glu Val Thr Met Thr Ala Leu Ser Pro Val Trp Leu Asp
625                 630                 635                 640
Ser Arg Ser Arg Tyr Leu Arg Asp Met Tyr Arg Pro Gly Met Val Met
                645                 650                 655
Glu Gln Trp Asn Pro Glu Thr Arg Ser His Asp Arg Tyr Val Ile Asp
            660                 665                 670
Arg Val Thr Ala Gln Ser His Ser Leu Thr Leu Arg Asp Ala Gln Gly
        675                 680                 685
Glu Thr Gln Val Val Arg Ile Ser Ser Leu Asp Ser Ser Trp Ser Leu
    690                 695                 700
Phe Arg Pro Glu Lys Met Pro Val Ala Asp Gly Glu Arg Leu Arg Val
705                 710                 715                 720
Thr Gly Lys Ile Pro Gly Leu Arg Val Ser Gly Gly Asp Arg Leu Gln
                725                 730                 735
Val Ala Ser Val Ser Glu Asp Ala Met Thr Val Val Pro Gly Arg
            740                 745                 750
Ala Glu Pro Ala Ser Leu Pro Val Ser Asp Ser Pro Phe Thr Ala Leu
        755                 760                 765
Lys Leu Glu Asn Gly Trp Val Glu Thr Pro Gly His Ser Val Ser Asp
    770                 775                 780
Ser Ala Thr Val Phe Ala Ser Val Thr Gln Met Ala Met Asp Asn Ala
785                 790                 795                 800
Thr Leu Asn Gly Leu Ala Arg Ser Gly Arg Asp Val Arg Leu Tyr Ser
                805                 810                 815
Ser Leu Asp Glu Thr Arg Thr Ala Glu Lys Leu Ala Arg His Pro Ser
            820                 825                 830
Phe Thr Val Val Ser Glu Gln Ile Lys Ala Arg Ala Gly Glu Thr Leu
        835                 840                 845
Leu Glu Thr Ala Ile Ser Leu Gln Lys Ala Gly Leu His Thr Pro Ala
    850                 855                 860
Gln Gln Ala Ile His Leu Ala Leu Pro Val Leu Glu Ser Lys Asn Leu
865                 870                 875                 880
Ala Phe Ser Met Val Asp Leu Leu Thr Glu Ala Lys Ser Phe Ala Ala
                885                 890                 895
Glu Gly Thr Gly Phe Thr Glu Leu Gly Gly Glu Ile Asn Ala Gln Ile
```

```
                900             905             910
Lys Arg Gly Asp Leu Leu Tyr Val Asp Val Ala Lys Gly Tyr Gly Thr
            915             920             925
Gly Leu Leu Val Ser Arg Ala Ser Tyr Glu Ala Glu Lys Ser Ile Leu
        930             935             940
Arg His Ile Leu Glu Gly Lys Glu Ala Val Thr Pro Leu Met Glu Arg
945             950             955             960
Val Pro Gly Glu Leu Met Glu Thr Leu Thr Ser Gly Gln Arg Ala Ala
                965             970             975
Thr Arg Met Ile Leu Glu Thr Ser Asp Arg Phe Thr Val Val Gln Gly
            980             985             990
Tyr Ala Gly Val Gly Lys Thr Thr Gln Phe Arg Ala Val Met Ser Ala
        995             1000            1005
Val Asn Met Leu Pro Ala Ser Glu Arg Pro Arg Val Val Gly Leu
    1010            1015            1020
Gly Pro Thr His Arg Ala Val Gly Glu Met Arg Ser Ala Gly Val
    1025            1030            1035
Asp Ala Gln Thr Leu Ala Ser Phe Leu His Asp Thr Gln Leu Gln
    1040            1045            1050
Gln Arg Ser Gly Glu Thr Pro Asp Phe Ser Asn Thr Leu Phe Leu
    1055            1060            1065
Leu Asp Glu Ser Ser Met Val Gly Asn Thr Glu Met Ala Arg Ala
    1070            1075            1080
Tyr Ala Leu Ile Ala Ala Gly Gly Gly Arg Ala Val Ala Ser Gly
    1085            1090            1095
Asp Thr Asp Gln Leu Gln Ala Ile Ala Pro Gly Gln Ser Phe Arg
    1100            1105            1110
Leu Gln Gln Thr Arg Ser Ala Ala Asp Val Val Ile Met Lys Glu
    1115            1120            1125
Ile Val Arg Gln Thr Pro Glu Leu Arg Glu Ala Val Tyr Ser Leu
    1130            1135            1140
Ile Asn Arg Asp Val Glu Arg Ala Leu Ser Gly Leu Glu Ser Val
    1145            1150            1155
Lys Pro Ser Gln Val Pro Arg Leu Glu Gly Ala Trp Ala Pro Glu
    1160            1165            1170
His Ser Val Thr Glu Phe Ser His Ser Gln Glu Ala Lys Leu Ala
    1175            1180            1185
Glu Ala Gln Gln Lys Ala Met Leu Lys Gly Glu Ala Phe Pro Asp
    1190            1195            1200
Ile Pro Met Thr Leu Tyr Glu Ala Ile Val Arg Asp Tyr Thr Gly
    1205            1210            1215
Arg Thr Pro Glu Ala Arg Glu Gln Thr Leu Ile Val Thr His Leu
    1220            1225            1230
Asn Glu Asp Arg Arg Val Leu Asn Ser Met Ile His Asp Ala Arg
    1235            1240            1245
Glu Lys Ala Gly Glu Leu Gly Lys Glu Gln Val Met Val Pro Val
    1250            1255            1260
Leu Asn Thr Ala Asn Ile Arg Asp Gly Glu Leu Arg Arg Leu Ser
    1265            1270            1275
Thr Trp Glu Lys Asn Pro Asp Ala Leu Ala Leu Val Asp Asn Val
    1280            1285            1290
Tyr His Arg Ile Ala Gly Ile Ser Lys Asp Asp Gly Leu Ile Thr
    1295            1300            1305
```

```
Leu Gln Asp Ala Glu Gly Asn Thr Arg Leu Ile Ser Pro Arg Glu
    1310                1315                1320

Ala Val Ala Glu Gly Val Thr Leu Tyr Thr Pro Asp Lys Ile Arg
    1325                1330                1335

Val Gly Thr Gly Asp Arg Met Arg Phe Thr Lys Ser Asp Arg Glu
    1340                1345                1350

Arg Gly Tyr Val Ala Asn Ser Val Trp Thr Val Thr Ala Val Ser
    1355                1360                1365

Gly Asp Ser Val Thr Leu Ser Asp Gly Gln Gln Thr Arg Val Ile
    1370                1375                1380

Arg Pro Gly Gln Glu Arg Ala Glu Gln His Ile Asp Leu Ala Tyr
    1385                1390                1395

Ala Ile Thr Ala His Gly Ala Gln Gly Ala Ser Glu Thr Phe Ala
    1400                1405                1410

Ile Ala Leu Glu Gly Thr Glu Gly Asn Arg Lys Leu Met Ala Gly
    1415                1420                1425

Phe Glu Ser Ala Tyr Val Ala Leu Ser Arg Met Lys Gln His Val
    1430                1435                1440

Gln Val Tyr Thr Asp Asn Arg Gln Gly Trp Thr Asp Ala Ile Asn
    1445                1450                1455

Asn Ala Val Gln Lys Gly Thr Ala His Asp Val Leu Glu Pro Lys
    1460                1465                1470

Pro Asp Arg Glu Val Met Asn Ala Gln Arg Leu Phe Ser Thr Ala
    1475                1480                1485

Arg Glu Leu Arg Asp Val Ala Gly Arg Ala Val Leu Arg Gln
    1490                1495                1500

Ala Gly Leu Ala Gly Gly Asp Ser Pro Ala Arg Phe Ile Ala Pro
    1505                1510                1515

Gly Arg Lys Tyr Pro Gln Pro Tyr Val Ala Leu Pro Ala Phe Asp
    1520                1525                1530

Arg Asn Gly Lys Ser Ala Gly Ile Trp Leu Asn Pro Leu Thr Thr
    1535                1540                1545

Asp Asp Gly Asn Gly Leu Arg Gly Phe Ser Gly Glu Gly Arg Val
    1550                1555                1560

Lys Gly Ser Gly Asp Ala Gln Phe Val Ala Leu Gln Gly Ser Arg
    1565                1570                1575

Asn Gly Glu Ser Leu Leu Ala Asp Asn Met Gln Asp Gly Val Arg
    1580                1585                1590

Ile Ala Arg Asp Asn Pro Asp Ser Gly Val Val Val Arg Ile Ala
    1595                1600                1605

Gly Glu Gly Arg Pro Trp Asn Pro Gly Ala Ile Thr Gly Gly Arg
    1610                1615                1620

Val Trp Gly Asp Ile Pro Asn Ser Val Gln Pro Gly Ala Gly
    1625                1630                1635

Asn Gly Glu Pro Val Thr Ala Glu Val Leu Ala Gln Arg Gln Ala
    1640                1645                1650

Glu Glu Ala Ile Arg Arg Glu Thr Glu Arg Arg Ala Asp Glu Ile
    1655                1660                1665

Val Arg Lys Met Ala Glu Asn Lys Pro Asp Leu Pro Asp Gly Lys
    1670                1675                1680

Thr Glu Leu Ala Val Arg Asp Ile Ala Gly Gln Glu Arg Asp Arg
    1685                1690                1695
```

```
Ser Ala Ile Ser Glu Arg Glu Thr Ala Leu Pro Glu Ser Val Leu
1700                1705                1710

Arg Glu Ser Gln Arg Glu Arg Glu Ala Val Arg Glu Val Ala Arg
1715                1720                1725

Glu Asn Leu Leu Gln Glu Arg Leu Gln Gln Met Glu Arg Asp Met
1730                1735                1740

Val Arg Asp Leu Gln Lys Glu Lys Thr Leu Gly Gly Asp
1745                1750                1755

<210> SEQ ID NO 23
<211> LENGTH: 726
<212> TYPE: PRT
<213> ORGANISM: Methanococcoides burtonii

<400> SEQUENCE: 23

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
                100                 105                 110

Cys Ser Val Lys Arg Glu Asn Thr Phe Glu Leu Met Glu Thr Glu Arg
            115                 120                 125

Glu Ile Tyr Leu Lys Arg Gln Glu Leu Asn Ser Ala Arg Asp Ser Tyr
        130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
                180                 185                 190

Arg Glu Trp Leu Tyr Lys Glu Val Arg Ser Pro Glu Glu Ile Asn Asp
            195                 200                 205

His Ala Ile Lys Asp Gly Met Cys Gly Tyr Glu Leu Val Lys Arg Glu
        210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
                260                 265                 270

Arg Ser His Ser Ser Leu Ser Leu Thr Glu His Ser Ile Glu Lys Ala
            275                 280                 285

Ile Thr Glu Leu Glu Ala Asn Leu Asp Leu Leu Ala Asp Asp Asn Ile
        290                 295                 300

His Asn Leu Phe Asn Ile Phe Leu Glu Val Ile Ser Asp Thr Tyr Asn
305                 310                 315                 320
```

```
Ser Arg Phe Lys Phe Gly Glu Arg Glu Arg Val Arg Lys Asn Trp Tyr
            325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
            355                 360                 365

Gln Ile Leu Leu Ser Glu Ala Ser Glu Leu Gly Ala Lys Leu Asp Glu
            370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
                420                 425                 430

Asn Asp Glu Ile Tyr Gly Arg Val Glu Leu Phe Thr Cys Ile Pro Lys
                435                 440                 445

Asn Val Thr Glu Pro Leu Phe Asn Ser Leu Phe Ser Val Ile Leu Met
            450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
                500                 505                 510

Arg Asp Asp Arg His Val Thr Glu Leu Leu Glu Gln Val Leu Leu Asp
                515                 520                 525

Ser Ile Glu Asn Ser Lys Gly Asn Val Ile Leu Phe Phe Gln Ser Ala
            530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
                580                 585                 590

Tyr Leu Trp Gly Thr Leu Ser Glu Gly Ile Asp Tyr Arg Asp Gly Arg
            595                 600                 605

Gly Arg Thr Val Ile Ile Ile Gly Val Gly Tyr Pro Ala Leu Asn Asp
            610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
                660                 665                 670

Ile Leu Leu Asp Gly Arg Phe Leu Thr Asp Ser Lys Lys Arg Phe Gly
                675                 680                 685

Lys Phe Ser Val Phe Glu Val Phe Pro Pro Ala Glu Arg Ser Glu Phe
            690                 695                 700

Val Asp Val Asp Pro Glu Lys Val Lys Tyr Ser Leu Met Asn Phe Phe
705                 710                 715                 720

Met Asp Asn Asp Glu Gln
            725
```

<210> SEQ ID NO 24
<211> LENGTH: 439
<212> TYPE: PRT
<213> ORGANISM: Enterobacteria phage T4

<400> SEQUENCE: 24

Met Thr Phe Asp Asp Leu Thr Glu Gly Gln Lys Asn Ala Phe Asn Ile
1               5                   10                  15

Val Met Lys Ala Ile Lys Glu Lys Lys His Val Thr Ile Asn Gly
        20                  25                  30

Pro Ala Gly Thr Gly Lys Thr Thr Leu Thr Lys Phe Ile Ile Glu Ala
            35                  40                  45

Leu Ile Ser Thr Gly Glu Thr Gly Ile Ile Leu Ala Ala Pro Thr His
        50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ser Ser Asp Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

```
Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
            405                 410                 415

Asp Val Glu Leu Ala Gln Gln Leu Leu Tyr Val Gly Val Thr Arg Gly
            420                 425                 430

Arg Tyr Asp Val Phe Tyr Val
        435

<210> SEQ ID NO 25
<211> LENGTH: 970
<212> TYPE: PRT
<213> ORGANISM: Clostridium botulinum

<400> SEQUENCE: 25

Met Leu Ser Val Ala Asn Val Arg Ser Pro Ser Ala Ala Ser Tyr
1               5                   10                  15

Phe Ala Ser Asp Asn Tyr Tyr Ala Ser Asp Ala Asp Arg Ser Gly
            20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
            130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
            275                 280                 285

Ala Arg Thr Lys Ala Leu Gly Gln Gly Met Glu Ala Thr Arg Ile Gly
290                 295                 300

Ser Leu Val Glu Arg Gly Arg Ala Trp Leu Ser Arg Phe Ala Ala His
```

-continued

```
            305                 310                 315                 320
Val Arg Gly Asp Pro Ala Asp Pro Leu Val Pro Ser Val Leu Lys
                325                 330                 335
Gln Asp Arg Gln Thr Ile Ala Ala Gln Ala Val Ala Ser Ala Val
                340                 345                 350
Arg His Leu Ser Gln Arg Glu Ala Ala Phe Glu Arg Thr Ala Leu Tyr
                355                 360                 365
Lys Ala Ala Leu Asp Phe Gly Leu Pro Thr Thr Ile Ala Asp Val Glu
    370                 375                 380
Lys Arg Thr Arg Ala Leu Val Arg Ser Gly Asp Leu Ile Ala Gly Lys
385                 390                 395                 400
Gly Glu His Lys Gly Trp Leu Ala Ser Arg Asp Ala Val Val Thr Glu
                    405                 410                 415
Gln Arg Ile Leu Ser Glu Val Ala Ala Gly Lys Gly Asp Ser Ser Pro
                420                 425                 430
Ala Ile Thr Pro Gln Lys Ala Ala Ala Ser Val Gln Ala Ala Ala Leu
                435                 440                 445
Thr Gly Gln Gly Phe Arg Leu Asn Glu Gly Gln Leu Ala Ala Ala Arg
    450                 455                 460
Leu Ile Leu Ile Ser Lys Asp Arg Thr Ile Ala Val Gln Gly Ile Ala
465                 470                 475                 480
Gly Ala Gly Lys Ser Ser Val Leu Lys Pro Val Ala Glu Val Leu Arg
                485                 490                 495
Asp Glu Gly His Pro Val Ile Gly Leu Ala Ile Gln Asn Thr Leu Val
                500                 505                 510
Gln Met Leu Glu Arg Asp Thr Gly Ile Gly Ser Gln Thr Leu Ala Arg
                515                 520                 525
Phe Leu Gly Gly Trp Asn Lys Leu Leu Asp Asp Pro Gly Asn Val Ala
    530                 535                 540
Leu Arg Ala Glu Ala Gln Ala Ser Leu Lys Asp His Val Leu Val Leu
545                 550                 555                 560
Asp Glu Ala Ser Met Val Ser Asn Glu Asp Lys Glu Lys Leu Val Arg
                565                 570                 575
Leu Ala Asn Leu Ala Gly Val His Arg Leu Val Leu Ile Gly Asp Arg
                580                 585                 590
Lys Gln Leu Gly Ala Val Asp Ala Gly Lys Pro Phe Ala Leu Leu Gln
                595                 600                 605
Arg Ala Gly Ile Ala Arg Ala Glu Met Ala Thr Asn Leu Arg Ala Arg
    610                 615                 620
Asp Pro Val Val Arg Glu Ala Gln Ala Ala Gln Ala Gly Asp Val
625                 630                 635                 640
Arg Lys Ala Leu Arg His Leu Lys Ser His Thr Val Glu Ala Arg Gly
                645                 650                 655
Asp Gly Ala Gln Val Ala Ala Glu Thr Trp Leu Ala Leu Asp Lys Glu
                660                 665                 670
Thr Arg Ala Arg Thr Ser Ile Tyr Ala Ser Gly Arg Ala Ile Arg Ser
    675                 680                 685
Ala Val Asn Ala Ala Val Gln Gln Gly Leu Leu Ala Ser Arg Glu Ile
    690                 695                 700
Gly Pro Ala Lys Met Lys Leu Glu Val Leu Asp Arg Val Asn Thr Thr
705                 710                 715                 720
Arg Glu Glu Leu Arg His Leu Pro Ala Tyr Arg Ala Gly Arg Val Leu
                725                 730                 735
```

```
Glu Val Ser Arg Lys Gln Gln Ala Leu Gly Leu Phe Ile Gly Glu Tyr
            740                 745                 750
Arg Val Ile Gly Gln Asp Arg Lys Gly Lys Leu Val Glu Val Glu Asp
        755                 760                 765
Lys Arg Gly Lys Arg Phe Arg Phe Asp Pro Ala Arg Ile Arg Ala Gly
770                 775                 780
Lys Gly Asp Asp Asn Leu Thr Leu Leu Glu Pro Arg Lys Leu Glu Ile
785                 790                 795                 800
His Glu Gly Asp Arg Ile Arg Trp Thr Arg Asn Asp His Arg Arg Gly
                805                 810                 815
Leu Phe Asn Ala Asp Gln Ala Arg Val Val Glu Ile Ala Asn Gly Lys
            820                 825                 830
Val Thr Phe Glu Thr Ser Lys Gly Asp Leu Val Glu Leu Lys Lys Asp
        835                 840                 845
Asp Pro Met Leu Lys Arg Ile Asp Leu Ala Tyr Ala Leu Asn Val His
850                 855                 860
Met Ala Gln Gly Leu Thr Ser Asp Arg Gly Ile Ala Val Met Asp Ser
865                 870                 875                 880
Arg Glu Arg Asn Leu Ser Asn Gln Lys Thr Phe Leu Val Thr Val Thr
                885                 890                 895
Arg Leu Arg Asp His Leu Thr Leu Val Val Asp Ser Ala Asp Lys Leu
            900                 905                 910
Gly Ala Ala Val Ala Arg Asn Lys Gly Glu Lys Ala Ser Ala Ile Glu
        915                 920                 925
Val Thr Gly Ser Val Lys Pro Thr Ala Thr Lys Gly Ser Gly Val Asp
930                 935                 940
Gln Pro Lys Ser Val Glu Ala Asn Lys Ala Glu Lys Glu Leu Thr Arg
945                 950                 955                 960
Ser Lys Ser Lys Thr Leu Asp Phe Gly Ile
                965                 970

<210> SEQ ID NO 26
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 26
tttttttttt cttttttttc tttttttggtt ggttgttggt tgg                    43

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
tttttttttt cttttttttt                                               20

<210> SEQ ID NO 28
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 28
```
ggttggttgt tggttgg                                                  17

<210> SEQ ID NO 29
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 29
ttaatgctaa tcgtgatagg ggt                                           23

<210> SEQ ID NO 30
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 30
gttctactaa accgtgtcaa tcagtgtc                                      28

<210> SEQ ID NO 31
<211> LENGTH: 3560
<212> TYPE: DNA
<213> ORGANISM: Artificial Sequence
<220> FEATURE:
<223> OTHER INFORMATION: Synthetic Polynucleotide

<400> SEQUENCE: 31
gccatcagat tgtgtttgtt agtcgctttt ttttttggga atttttttt tggaattttt      60 tttttgcgct aacaacctcc tgccgttttg cccgtgcata tcggtcacga acaaatctga    120
ttactaaaca cagtagcctg gatttgttct atcagtaatc gaccttattc ctaattaaat    180
agagcaaatc cccttattgg gggtaagaca tgaagatgcc agaaaaacat gacctgttgg    240
ccgccattct cgcggcaaag gaacaaggca tcggggcaat ccttgcgttt gcaatggcgt    300
accttcgcgg cagatataat ggcggtgcgt ttacaaaaac agtaatcgac gcaacgatgt    360
gcgccattat cgcctagttc attcgtgacc ttctcgactt cgccggacta agtagcaatc    420
tcgcttatat aacgagcgtg tttatcggct acatcggtac tgactcgatt ggttcgctta    480
tcaaacgctt cgctgctaaa aaagccggag tagaagatgg tagaaatcaa taatcaacgt    540
aaggcgttcc tcgatatgct ggcgtggtcg gagggaactg ataacggacg tcagaaaacc    600
agaaatcatg gttatgacgt cattgtaggc ggagagctat ttactgatta ctccgatcac    660
cctcgcaaac ttgtcacgct aaacccaaaa ctcaaatcaa caggcgccgg acgctaccag    720
cttctttccc gttggtggga tgcctaccgc aagcagcttg gcctgaaaga cttctctccg    780
aaaagtcagg acgctgtggc attgcagcag attaaggagc gtggcgcttt acctatgatt    840
gatcgtggtg atatccgtca ggcaatcgac cgttgcagca atatctgggc ttcactgccg    900
ggcgctggtt atggtcagtt cgagcataag gctgacagcc tgattgcaaa attcaaagaa    960
gcgggcggaa cggtcagaga gattgatgta tgagcagagt caccgcgatt atctccgctc   1020
tggttatctg catcatcgtc tgcctgtcat gggctgttaa tcattaccgt gataacgcca   1080
ttacctacaa agcccagcgc gacaaaaatg ccagagaact gaagctggcg aacgcggcaa   1140
ttactgacat gcagatgcgt cagcgtgatg ttgctgcgct cgatgcaaaa tacacgaagg   1200
agttagctga tgctaaagct gaaaatgatg ctctgcgtga tgatgttgcc gctggtcgtc   1260

-continued

```
gtcggttgca catcaaagca gtctgtcagt cagtgcgtga agccaccacc gcctccggcg    1320
tggataatgc agcctccccc cgactggcag acaccgctga acgggattat ttcaccctca    1380
gagagaggct gatcactatg caaaaacaac tggaaggaac ccagaagtat attaatgagc    1440
agtgcagata gagttgccca tatcgatggg caactcatgc aattattgtg agcaatacac    1500
acgcgcttcc agcggagtat aaatgcctaa agtaataaaa ccgagcaatc catttacgaa    1560
tgtttgctgg gtttctgttt taacaacatt ttctgcgccg ccacaaattt tggctgcatc    1620
gacagttttc ttctgcccaa ttccagaaac gaagaaatga tgggtgatgg tttcctttgg    1680
tgctactgct gccggtttgt tttgaacagt aaacgtctgt tgagcacatc ctgtaataag    1740
cagggccagc gcagtagcga gtagcatttt tttcatggtg ttattcccga tgcttttga    1800 agttcgcaga atcgtatgtg tagaaaatta acaaaccct aaacaatgag ttgaaatttc     1860
atattgttaa tatttattaa tgtatgtcag gtgcgatgaa tcgtcattgt attcccggat    1920
taactatgtc cacagccctg acggggaact tctctgcggg agtgtccggg ataattaaa     1980 acgatgcaca cagggtttag cgcgtacacg tattgcatta tgccaacgcc ccggtgctga    2040
cacggaagaa accggacgtt atgatttagc gtggaaagat ttgtgtagtg ttctgaatgc    2100
tctcagtaaa tagtaatgaa ttatcaaagg tatagtaata tcttttatgt tcatggatat    2160
ttgtaaccca tcggaaaact cctgctttag caagattttc cctgtattgc tgaaatgtga    2220
tttctcttga tttcaaccta tcataggacg tttctataag atgcgtgttt cttgagaatt    2280
taacatttac aaccttttta agtccttttta ttaacacggt gttatcgttt tctaacacga    2340
tgtgaatatt atctgtggct agatagtaaa tataatgtga gacgttgtga cgttttagtt    2400
cagaataaaa caattcacag tctaaatctt ttcgcacttg atcgaatatt tcttaaaaa    2460 tggcaacctg agccattggt aaaaccttcc atgtgatacg agggcgcgta gtttgcatta    2520
tcgtttttat cgtttcaatc tggtctgacc tccttgtgtt ttgttgatga tttatgtcaa    2580
atattaggaa tgttttcact taatagtatt ggttgcgtaa caaagtgcgg tcctgctggc    2640
attctggagg gaaatacaac cgacagatgt atgtaaggcc aacgtgctca atcttcata    2700 cagaaagatt tgaagtaata ttttaaccgc tagatgaaga gcaagcgcat ggagcgacaa    2760
aatgaataaa gaacaatctg ctgatgatcc ctccgtggat ctgattcgtg taaaaaatat    2820
gcttaatagc accatttcta tgagttaccc tgatgttgta attgcatgta tagaacataa    2880
ggtgtctctg gaagcattca gagcaattga ggcagcgttg gtgaagcacg ataataatat    2940
gaaggattat tccctggtgg ttgactgatc accataactg ctaatcattc aaactattta    3000
gtctgtgaca gagccaacac gcagtctgtc actgtcagga aagtggtaaa actgcaactc    3060
aattactgca atgccctcgt aattaagtga atttacaata tcgtcctgtt cggagggaag    3120
aacgcgggat gttcattctt catcactttt aattgatgta tatgctctct tttctgacgt    3180
tagtctccga cggcaggctt caatgaccca ggctgagaaa ttcccggacc ttttttgctc    3240
aagagcgatg ttaatttgtt caatcatttg gttaggaaag cggatgttgc gggttgttgt    3300
tctgcgggtt ctgttcttcg ttgacatgag gttgccccgt attcagtgtc gctgatttgt    3360
attgtctgaa gttgttttta cgttaagttg atgcagatca attaatacga tacctgcgtc    3420
ataattgatt atttgacgtg gtttgatggc ctccacgcac gttgtgatat gtagatgata    3480
atcattatca ctttacgggt cctttccggt gaaaaaaag gtaccaaaaa aacatcgtc     3540 gtgagtagtg aaccgtaagc                                               3560
```

```
<210> SEQ ID NO 32
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 32
gccatcagat tgtgtttgtt agtcgctttt ttttttgga atttttttt tggaatttt      60 tttttgcgct aacaacctcc tgccg                                         85

<210> SEQ ID NO 33
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 33
gcttacggtt cactactcac gacgatgttt ttttggtac cttttttttc accggaaagg    60
acccgtaaag tg                                                       72

<210> SEQ ID NO 34
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 34
tttttttttt tttttttttt tttttttttt tttttttttt tttttt                  46

<210> SEQ ID NO 35
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 35
ggttgtttct gttggtgctg atattgc                                       27

<210> SEQ ID NO 36
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 36
gccatcagat tgtgtttgtt agtcgct                                       27

<210> SEQ ID NO 37
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 37
acactgattg acacggttta gtagaac                                       27

<210> SEQ ID NO 38
<211> LENGTH: 27
<212> TYPE: DNA
```

<213> ORGANISM: Artificial Sequence
<220> FEATURE:
<223> OTHER INFORMATION: Synthetic Polynucleotide

<400> SEQUENCE: 38

```
gcttacggtt cactactcac gacgatg                                        27
```

<210> SEQ ID NO 39
<211> LENGTH: 3587
<212> TYPE: DNA
<213> ORGANISM: Artificial Sequence
<220> FEATURE:
<223> OTHER INFORMATION: Synthetic Polynucleotide

<400> SEQUENCE: 39

```
gccatcagat tgtgtttgtt agtcgctgcc atcagattgt gtttgttagt cgctttttt      60
ttttggaatt ttttttttgg aattttttt ttgcgctaac aacctcctgc cgttttgccc    120
gtgcatatcg gtcacgaaca aatctgatta ctaaacacag tagcctggat ttgttctatc   180
agtaatcgac cttattccta attaaataga gcaaatcccc ttattggggg taagacatga   240
agatgccaga aaacatgac ctgttggccg ccattctcgc ggcaaaggaa caaggcatcg    300
gggcaatcct tgcgtttgca atggcgtacc ttcgcggcag atataatggc ggtgcgttta   360
caaaaacagt aatcgacgca acgatgtgcg ccattatcgc ctagttcatt cgtgaccttc   420
tcgacttcgc cggactaagt agcaatctcg cttatataac gagcgtgttt atcggctaca   480
tcggtactga ctcgattggt tcgcttatca aacgcttcgc tgctaaaaaa gccggagtag   540
aagatggtag aaatcaataa tcaacgtaag gcgttcctcg atatgctggc gtggtcggag   600
ggaactgata acggacgtca gaaaaccaga atcatggtt atgacgtcat tgtaggcgga   660
gagctattta ctgattactc cgatcaccct cgcaaacttg tcacgctaaa cccaaaactc   720
aaatcaacag gcgccggacg ctaccagctt cttcccgtt ggtgggatgc ctaccgcaag   780
cagcttggcc tgaaagactt ctctccgaaa agtcaggacg ctgtggcatt gcagcagatt   840
aaggagcgtg gcgctttacc tatgattgat cgtggtgata ccgtcaggc aatcgaccgt   900
tgcagcaata tctgggcttc actgccgggc gctggttatg gtcagttcga gcataaggct   960
gacagcctga ttgcaaaatt caaagaagcg ggcggaacgg tcagagagat tgatgtatga  1020
gcagagtcac cgcgattatc tccgctctgg ttatctgcat catcgtctgc ctgtcatggg  1080
ctgttaatca ttaccgtgat aacgccatta cctacaaagc ccagcgcgac aaaaatgcca  1140
gagaactgaa gctggcgaac gcggcaatta ctgacatgca gatgcgtcag cgtgatgttg  1200
ctgcgctcga tgcaaaatac acgaaggagt tagctgatgc taaagctgaa atgatgctc   1260
tgcgtgatga tgttgccgct ggtcgtcgtc ggttgcacat caaagcagtc tgtcagtcag  1320
tgcgtgaagc caccaccgcc tccggcgtgg ataatgcagc tccccccga ctggcagaca  1380
ccgctgaacg ggattatttc accctcagag agaggctgat cactatgcaa aaacaactgg  1440
aaggaaccca gaagtatatt aatgagcagt gcagatagag ttgcccatat cgatgggcaa  1500
ctcatgcaat tattgtgagc aatacacacg cgcttccagc ggagtataaa tgcctaaagt  1560
aataaaaccg agcaatccat ttacgaatgt ttgctgggtt tctgttttaa caacattttc  1620
tgcgccgcca caaatttggg ctgcatcgac agttttcttc tgcccaattc cagaaacgaa  1680
gaaatgatgg gtgatggttt cctttggtgc tactgctgcc ggtttgtttt gaacagtaaa  1740
cgtctgttga gcacatcctg taataagcag ggccagcgca gtagcgagta gcatttttt   1800
catggtgtta ttcccgatgc ttttttgaagt tcgcagaatc gtatgtgtag aaaattaaac  1860
```

```
aaaccctaaa caatgagttg aaatttcata ttgttaatat ttattaatgt atgtcaggtg     1920
cgatgaatcg tcattgtatt cccggattaa ctatgtccac agccctgacg gggaacttct     1980
ctgcgggagt gtccgggaat aattaaaacg atgcacacag ggtttagcgc gtacacgtat     2040
tgcattatgc caacgccccg gtgctgacac ggaagaaacc ggacgttatg atttagcgtg     2100
gaaagatttg tgtagtgttc tgaatgctct cagtaaatag taatgaatta tcaaaggtat     2160
agtaatatct tttatgttca tggatatttg taacccatcg gaaaactcct gctttagcaa     2220
gattttccct gtattgctga aatgtgattt ctcttgattt caacctatca taggacgttt     2280
ctataagatg cgtgtttctt gagaatttaa catttacaac cttttaagt ccttttatta      2340 acacggtgtt atcgttttct aacacgatgt gaatattatc tgtggctaga tagtaaatat     2400
aatgtgagac gttgtgacgt tttagttcag aataaaacaa ttcacagtct aaatcttttc     2460
gcacttgatc gaatatttct ttaaaaatgg caacctgagc cattggtaaa accttccatg     2520
tgatacgagg gcgcgtagtt tgcattatcg ttttatcgt ttcaatctgg tctgacctcc      2580
ttgtgttttg ttgatgattt atgtcaaata ttaggaatgt tttcacttaa tagtattggt     2640
tgcgtaacaa agtgcggtcc tgctggcatt ctggagggaa atacaaccga cagatgtatg     2700
taaggccaac gtgctcaaat cttcatacag aaagatttga agtaatattt taaccgctag     2760
atgaagagca agcgcatgga gcgacaaaat gaataaagaa caatctgctg atgatccctc     2820
cgtggatctg attcgtgtaa aaaatatgct taatagcacc atttctatga gttaccctga     2880
tgttgtaatt gcatgtatag aacataaggt gtctctggaa gcattcagag caattgaggc     2940
agcgttggtg aagcacgata ataatatgaa ggattattcc ctggtggttg actgatcacc     3000
ataactgcta atcattcaaa ctatttagtc tgtgacagag ccaacacgca gtctgtcact     3060
gtcaggaaag tggtaaaact gcaactcaat tactgcaatg ccctcgtaat taagtgaatt     3120
tacaatatcg tcctgttcgg agggaagaac gcgggatgtt cattcttcat cactttttaat   3180 tgatgtatat gctctctttt ctgacgttag tctccgacgg caggcttcaa tgacccaggc     3240
tgagaaattc ccggacccctt tttgctcaag agcgatgtta atttgttcaa tcatttggtt   3300
aggaaagcgg atgttgcggg ttgttgttct gcgggttctg ttcttcgttg acatgaggtt    3360
gccccgtatt cagtgtcgct gatttgtatt gtctgaagtt gttttttacgt taagttgatg   3420 cagatcaatt aatacgatac ctgcgtcata attgattatt tgacgtggtt tgatggcctc    3480
cacgcacgtt gtgatatgta gatgataatc attatcactt tacgggtcct ttccggtgaa    3540
aaaaaaggta ccaaaaaaaa catcgtcgtg agtagtgaac cgtaagc                  3587
```

<210> SEQ ID NO 40
<211> LENGTH: 3560
<212> TYPE: DNA
<213> ORGANISM: Artificial Sequence
<220> FEATURE:
<223> OTHER INFORMATION: Synthetic Polynucleotide

<400> SEQUENCE: 40

```
gcttacggtt cactactcac gacgatgttt tttttggtac cttttttttc accggaaagg      60
acccgtaaag tgataatgat tatcatctac atatcacaac gtgcgtggag gccatcaaac     120
cacgtcaaat aatcaattat gacgcaggta tcgtattaat tgatctgcat caacttaacg     180
taaaaacaac ttcagacaat acaaatcagc gacactgaat acggggcaac ctcatgtcaa     240
cgaagaacag aacccgcaga acaacaaccc gcaacatccg ctttcctaac caaatgattg     300
```

```
aacaaattaa catcgctctt gagcaaaaag gtccgggaa tttctcagcc tgggtcattg    360
aagcctgccg tcggagacta acgtcagaaa agagagcata tacatcaatt aaaagtgatg    420
aagaatgaac atcccgcgtt cttccctccg aacaggacga tattgtaaat tcacttaatt    480
acgagggcat tgcagtaatt gagttgcagt tttaccactt tcctgacagt gacagactgc    540
gtgttggctc tgtcacagac taaatagttt gaatgattag cagttatggt gatcagtcaa    600
ccaccaggga ataatccttc atattattat cgtgcttcac caacgctgcc tcaattgctc    660
tgaatgcttc cagagacacc ttatgttcta tacatgcaat tacaacatca gggtaactca    720
tagaaatggt gctattaagc atatttttta cacgaatcag atccacggag ggatcatcag    780
cagattgttc tttattcatt ttgtcgctcc atgcgcttgc tcttcatcta gcggttaaaa    840
tattacttca aatctttctg tatgaagatt tgagcacgtt ggccttacat acatctgtcg    900
gttgtatttc cctccagaat gccagcagga ccgcactttg ttacgcaacc aatactatta    960
agtgaaaaca ttcctaatat ttgacataaa tcatcaacaa acacaagga ggtcagacca    1020 gattgaaacg ataaaaacga taatgcaaac tacgcgccct cgtatcacat ggaaggtttt    1080
accaatggct caggttgcca tttttaaaga aatattcgat caagtgcgaa aagatttaga    1140
ctgtgaattg ttttattctg aactaaaacg tcacaacgtc tcacattata tttactatct    1200
agccacagat aatattcaca tcgtgttaga aaacgataac accgtgttaa taaaaggact    1260
taaaaaggtt gtaaatgtta aattctcaag aaacacgcat cttatagaaa cgtcctatga    1320
taggttgaaa tcaagagaaa tcacatttca gcaatacagg gaaaatcttg ctaaagcagg    1380
agttttccga tggttacaa atatccatga acataaaaga tattactata cctttgataa    1440
ttcattacta tttactgaga gcattcagaa cactacacaa atctttccac gctaaatcat    1500
aacgtccggt ttcttccgtg tcagcaccgg ggcgttggca taatgcaata cgtgtacgcg    1560
ctaaaccctg tgtgcatcgt tttaattatt cccggacact cccgcagaga agttccccgt    1620
cagggctgtg gacatagtta atccgggaat acaatgacga ttcatcgcac ctgacataca    1680
ttaataaata ttaacaatat gaaatttcaa ctcattgttt agggtttgtt taattttcta    1740
cacatacgat tctgcgaact tcaaaaagca tcgggaataa caccatgaaa aaatgctac    1800 tcgctactgc gctggccctg cttattacag gatgtgctca acagacgttt actgttcaaa    1860
acaaaccggc agcagtagca ccaaaggaaa ccatcaccca tcatttcttc gtttctggaa    1920
ttgggcagaa gaaaactgtc gatgcagcca aaatttgtgg cggcgcagaa aatgttgtta    1980
aaacagaaac ccagcaaaca ttcgtaaatg gattgctcgg ttttattact ttaggcattt    2040
atactccgct ggaagcgcgt gtgtattgct cacaataatt gcatgagttg cccatcgata    2100
tgggcaactc tatctgcact gctcattaat atacttctgg gttccttcca gttgtttttg    2160
catagtgatc agcctctctc tgagggtgaa ataatcccgt tcagcggtgt ctgccagtcg    2220
gggggaggct gcattatcca cgccggaggc ggtggtggct tcacgcactg actgacagac    2280
tgctttgatg tgcaaccgac gacgaccagc ggcaacatca tcacgcagag catcattttc    2340
agctttagca tcagctaact ccttcgtgta ttttgcatcg agcgcagcaa catcacgctg    2400
acgcatctgc atgtcagtaa ttgccgcgtt cgccagcttc agttctctgg cattttttgtc    2460 gcgctgggct ttgtaggtaa tggcgttatc acggtaatga ttaacagccc atgacaggca    2520
gacgatgatg cagataacca gagcggagat aatcgcggtg actctgctca tacatcaatc    2580
tctctgaccg ttccgcccgc ttctttgaat tttgcaatca ggctgtcagc cttatgctcg    2640
aactgaccat aaccagcgcc cggcagtgaa gcccagatat tgctgcaacg gtcgattgcc    2700
```

```
tgacggatat caccacgatc aatcataggt aaagcgccac gctccttaat ctgctgcaat    2760
gccacagcgt cctgactttt cggagagaag tctttcaggc caagctgctt gcggtaggca    2820
tcccaccaac gggaaagaag ctggtagcgt ccggcgcctg ttgatttgag ttttgggttt    2880
agcgtgacaa gtttgcgagg gtgatcggag taatcagtaa atagctctcc gcctacaatg    2940
acgtcataac catgatttct ggttttctga cgtccgttat cagttccctc cgaccacgcc    3000
agcatatcga ggaacgcctt acgttgatta ttgatttcta ccatcttcta ctccggcttt    3060
tttagcagcg aagcgtttga taagcgaacc aatcgagtca gtaccgatgt agccgataaa    3120
cacgctcgtt atataagcga gattgctact tagtccggcg aagtcgagaa ggtcacgaat    3180
gaactaggcg ataatggcgc acatcgttgc gtcgattact gttttttgtaa acgcaccgcc    3240 attatatctg ccgcgaaggt acgccattgc aaacgcaagg attgcccccga tgccttgttc    3300 ctttgccgcg agaatggcgg ccaacaggtc atgttttttct ggcatcttca tgtcttaccc    3360
ccaataaggg gatttgctct atttaattag gaataaggtc gattactgat agaacaaatc    3420
caggctactg tgtttagtaa tcagatttgt tcgtgaccga tatgcacggg caaaacggca    3480
ggaggttgtt agcgcaaaaa aaaaattcca aaaaaaaaat tccaaaaaaa aaaagcgact    3540
aacaaacaca atctgatggc                                              3560

<210> SEQ ID NO 41
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 41
gcaatatcag caccaacaga aacaacctt                                       29

<210> SEQ ID NO 42
<211> LENGTH: 103
<212> TYPE: DNA
<213> ORGANISM: Artificial Sequence
<220> FEATURE:
<223> OTHER INFORMATION: Synthetic Polynucleotide

<400> SEQUENCE: 42
tttttttttt tttttttttt tttttttttt tttttttttt tttttttttt tttttttttt      60
tttttttttt ttttttggtt gtttctgttg gtgctgatat tgc                      103

<210> SEQ ID NO 43
<211> LENGTH: 606
<212> TYPE: DNA
<213> ORGANISM: Artificial Sequence
<220> FEATURE:
<223> OTHER INFORMATION: Synthetic Polynucleotide

<400> SEQUENCE: 43
gccatcagat tgtgtttgtt agtcgctttt tttttttgga attttttttt tggaattttt      60
tttttgacgc tcagtaatgt gacgatagct gaaaactgta cgataaacgg tacgctgagg     120
gcggaaaaaa tcgtcgggga cattgtaaag gcggcgagcg cggcttttcc gcgccagcgt     180
gaaagcagtg tggactggcc gtcaggtacc cgtactgtca ccgtgaccga tgaccatcct     240
tttgatcgcc agatagtggt gcttccgctg acgtttcgcg gaagtaagcg tactgtcagc     300
ggcaggacaa cgtattcgat gtgttatctg aaagtactga tgaacggtgc ggtgatttat     360
```

```
gatggcgcgg cgaacgaggc ggtacaggtg ttctcccgta ttgttgacat gccagcgggt    420
cggggaaacg tgatcctgac gttcacgctt acgtccacac ggcattcggc agatattccg    480
ccgtatacgt ttgccagcga tgtgcaggtt atggtgatta agaaacaggc gctgggcatc    540
agcgtggtct gagtgtgaaa aaaaggtac caaaaaaaac atcgtcgtga gtagtgaacc    600
gtaagc                                                               606
```

<210> SEQ ID NO 44
<211> LENGTH: 606
<212> TYPE: DNA
<213> ORGANISM: Artificial Sequence
<220> FEATURE:
<223> OTHER INFORMATION: Synthetic Polynucleotide

<400> SEQUENCE: 44

```
gcttacggtt cactactcac gacgatgttt tttttggtac ctttttttc acactcagac    60 cacgctgatg cccagcgcct gtttcttaat caccataacc tgcacatcgc tggcaaacgt   120
atacggcgga atatctgccg aatgccgtgt ggacgtaagc gtgaacgtca ggatcacgtt   180
tccccgaccc gctggcatgt caacaatacg ggagaacacc tgtaccgcct cgttcgccgc   240
gccatcataa atcaccgcac cgttcatcag tactttcaga taacacatcg aatacgttgt   300
cctgccgctg acagtacgct tacttccgcg aaacgtcagc ggaagcacca ctatctggcg   360
atcaaaagga tggtcatcgg tcacggtgac agtacgggta cctgacgcc agtccacact   420 gctttcacgc tggcgcggaa aagccgcgct cgccgccttt acaatgtccc cgacgatttt   480
ttccgccctc agcgtaccgt ttatcgtaca gttttcagct atcgtcacat tactgagcgt   540
caaaaaaaaa attccaaaaa aaaaattcca aaaaaaaaaa gcgactaaca aacacaatct   600
gatggc                                                               606
```

<210> SEQ ID NO 45
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 45

```
gcaatatcag caccaacaga aacaacct                                       28
```

<210> SEQ ID NO 46
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 46

```
tttttttttt                                                           10
```

<210> SEQ ID NO 47
<211> LENGTH: 3560
<212> TYPE: DNA
<213> ORGANISM: Artificial Sequence
<220> FEATURE:
<223> OTHER INFORMATION: Synthetic Polynucleotide

<400> SEQUENCE: 47

```
gcttacggtt cactactcac gacgatgttt tttttggtac ctttttttc accggaaagg    60 acccgtaaag tgataatgat tatcatctac atatcacaac gtgcgtggag gccatcaaac   120
```

```
cacgtcaaat aatcaattat gacgcaggta tcgtattaat tgatctgcat caacttaacg      180
taaaaacaac ttcagacaat acaaatcagc gacactgaat acggggcaac ctcatgtcaa      240
cgaagaacag aacccgcaga acaacaaccc gcaacatccg ctttcctaac caaatgattg      300
aacaaattaa catcgctctt gagcaaaaag ggtccgggaa tttctcagcc tgggtcattg      360
aagcctgccg tcggagacta acgtcagaaa agagagcata tacatcaatt aaaagtgatg      420
aagaatgaac atcccgcgtt cttccctccg aacaggacga tattgtaaat tcacttaatt      480
acgagggcat tgcagtaatt gagttgcagt tttaccactt tcctgacagt gacagactgc      540
gtgttggctc tgtcacagac taaatagttt gaatgattag cagttatggt gatcagtcaa      600
ccaccaggga ataatccttc atattattat cgtgcttcac caacgctgcc tcaattgctc      660
tgaatgcttc cagagacacc ttatgttcta tacatgcaat tacaacatca gggtaactca      720
tagaaatggt gctattaagc atatttttta cacgaatcag atccacggag ggatcatcag      780
cagattgttc tttattcatt ttgtcgctcc atgcgcttgc tcttcatcta gcggttaaaa      840
tattacttca aatctttctg tatgaagatt tgagcacgtt ggccttacat acatctgtcg      900
gttgtatttc cctccagaat gccagcagga ccgcactttg ttacgcaacc aatactatta      960
agtgaaaaca ttcctaatat ttgacataaa tcatcaacaa aacacaagga ggtcagacca     1020
gattgaaacg ataaaaacga taatgcaaac tacgcgccct cgtatcacat ggaaggtttt     1080
accaatggct caggttgcca tttttaaaga aatattcgat caagtgcgaa aagatttaga     1140
ctgtgaattg ttttattctg aactaaaacg tcacaacgtc tcacattata tttactatct     1200
agccacagat aatattcaca tcgtgttaga aaacgataac accgtgttaa taaaaggact     1260
taaaaaggtt gtaaatgtta aattctcaag aaacacgcat cttatagaaa cgtcctatga     1320
taggttgaaa tcaagagaaa tcacatttca gcaatacagg gaaaatcttg ctaaagcagg     1380
agttttccga tgggttacaa atatccatga acataaaaga tattactata cctttgataa     1440
ttcattacta tttactgaga gcattcagaa cactacacaa atctttccac gctaaatcat     1500
aacgtccggt ttcttccgtg tcagcaccgg ggcgttggca taatgcaata cgtgtacgcg     1560
ctaaaccctg tgtgcatcgt tttaattatt cccggacact cccgcagaga agttccccgt     1620
cagggctgtg gacatagtta atccgggaat acaatgacga ttcatcgcac ctgacataca     1680
ttaataaata ttaacaatat gaaatttcaa ctcattgttt agggtttgtt taattttcta     1740
cacatacgat tctgcgaact tcaaaaagca tcgggaataa caccatgaaa aaaatgctac     1800
tcgctactgc gctggccctg cttattacag gatgtgctca acagacgttt actgttcaaa     1860
acaaaccggc agcagtagca ccaaaggaaa ccatcaccca tcatttcttc gtttctggaa     1920
ttgggcagaa gaaaactgtc gatgcagcca aaatttgtgg cggcgcagaa atgttgtta      1980 aaacagaaac ccagcaaaca ttcgtaaatg gattgctcgg ttttattact ttaggcattt     2040
atactccgct ggaagcgcgt gtgtattgct cacaataatt gcatgagttg cccatcgata     2100
tgggcaactc tatctgcact gctcattaat atacttctgg gttccttcca gttgtttttg     2160
catagtgatc agcctctctc tgagggtgaa ataatcccgt tcagcggtgt ctgccagtcg     2220
gggggaggct gcattatcca cgccggaggc ggtggtggct tcacgcactg actgacagac     2280
tgctttgatg tgcaaccgac gacgaccagc ggcaacatca tcacgcagag catcattttc     2340
agctttagca tcagctaact ccttcgtgta ttttgcatcg agcgcagcaa catcacgctg     2400
acgcatctgc atgtcagtaa ttgccgcgtt cgccagcttc agttctctgg catttttgtc     2460
```

```
gcgctgggct ttgtaggtaa tggcgttatc acggtaatga ttaacagccc atgacaggca    2520
gacgatgatg cagataacca gagcggagat aatcgcggtg actctgctca tacatcaatc    2580
tctctgaccg ttccgcccgc ttctttgaat tttgcaatca ggctgtcagc cttatgctcg    2640
aactgaccat aaccagcgcc cggcagtgaa gcccagatat tgctgcaacg gtcgattgcc    2700
tgacggatat caccacgatc aatcataggt aaagcgccac gctccttaat ctgctgcaat    2760
gccacagcgt cctgactttt cggagagaag tctttcaggc caagctgctt gcggtaggca    2820
tcccaccaac gggaaagaag ctggtagcgt ccggcgcctg ttgatttgag ttttgggttt    2880
agcgtgacaa gtttgcgagg gtgatcggag taatcagtaa atagctctcc gcctacaatg    2940
acgtcataac catgatttct ggttttctga cgtccgttat cagttccctc cgaccacgcc    3000
agcatatcga ggaacgcctt acgttgatta ttgatttcta ccatcttcta ctccggcttt    3060
tttagcagcg aagcgtttga taagcgaacc aatcgagtca gtaccgatgt agccgataaa    3120
cacgctcgtt atataagcga gattgctact tagtccggcg aagtcgagaa ggtcacgaat    3180
gaactaggcg ataatggcgc acatcgttgc gtcgattact gttttgtaa acgcaccgcc    3240 attatatctg ccgcgaaggt acgccattgc aaacgcaagg attgccccga tgccttgttc    3300
ctttgccgcg agaatggcgg ccaacaggtc atgtttttct ggcatcttca tgtcttaccc    3360
ccaataaggg gatttgctct atttaattag gaataaggtc gattactgat agaacaaatc    3420
caggctactg tgtttagtaa tcagatttgt tcgtgaccga tatgcacggg caaaacggca    3480
ggaggttgtt agcgcaaaaa aaaaattcca aaaaaaaat tccaaaaaaa aaaagcgact    3540
aacaaacaca atctgatggc                                              3560
```